US011834653B2

(12) United States Patent
Elledge et al.

(10) Patent No.: US 11,834,653 B2
(45) Date of Patent: Dec. 5, 2023

(54) METHODS AND COMPOSITIONS FOR IDENTIFYING EPITOPES

(71) Applicant: The Brigham and Women's Hospital, Inc., Boston, MA (US)

(72) Inventors: Stephen Elledge, Brookline, MA (US); Tomasz Kula, Brookline, MA (US); Mohammad Haj Dezfulian, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 882 days.

(21) Appl. No.: 16/619,859

(22) PCT Filed: Jun. 8, 2018

(86) PCT No.: PCT/US2018/036663
§ 371 (c)(1),
(2) Date: Dec. 5, 2019

(87) PCT Pub. No.: WO2018/227091
PCT Pub. Date: Dec. 13, 2018

(65) Prior Publication Data
US 2020/0102553 A1   Apr. 2, 2020

Related U.S. Application Data

(60) Provisional application No. 62/516,977, filed on Jun. 8, 2017.

(51) Int. Cl.
C12N 15/10    (2006.01)
C12N 5/0783   (2010.01)
C12N 5/09     (2010.01)
C40B 20/04    (2006.01)
C40B 40/02    (2006.01)
G01N 33/50    (2006.01)

(52) U.S. Cl.
CPC ....... *C12N 15/1037* (2013.01); *C12N 5/0636* (2013.01); *C12N 5/0693* (2013.01); *C40B 20/04* (2013.01); *C40B 40/02* (2013.01); *G01N 33/5047* (2013.01); *C12N 2529/10* (2013.01); *G01N 2333/96436* (2013.01)

(58) Field of Classification Search
CPC .............. C12N 15/1037; C12N 5/0636; C12N 5/0693; G01N 2333/96436
See application file for complete search history.

(56) References Cited

U.S. PATENT DOCUMENTS

| | | | |
|---|---|---|---|
| 7,927,871 B2 | 4/2011 | Packard et al. | |
| 9,518,084 B2 | 12/2016 | Pardon et al. | |
| 2003/0147810 A1 | 8/2003 | Ross et al. | |
| 2003/0211548 A1 | 11/2003 | Packard et al. | |
| 2004/0244071 A1* | 12/2004 | Chambron | C12N 15/63 |
| | | | 800/278 |
| 2007/0184493 A1* | 8/2007 | Packard | G01N 33/5055 |
| | | | 530/324 |
| 2009/0092582 A1* | 4/2009 | Bogin | A61P 3/10 |
| | | | 435/69.51 |
| 2009/0298089 A1* | 12/2009 | Rossner | C12N 15/1055 |
| | | | 435/7.1 |
| 2016/0264665 A1 | 9/2016 | Lim et al. | |
| 2018/0052176 A1 | 2/2018 | Holt et al. | |

FOREIGN PATENT DOCUMENTS

| | | | |
|---|---|---|---|
| CN | 101563104 A | 10/2009 | |
| EP | 1873251 A1 | 1/2008 | |
| WO | WO 2015/143558 | 10/2015 | |
| WO | WO-2015143558 A1 * | 10/2015 | ......... C12N 15/1037 |
| WO | WO 2017/053902 | 3/2017 | |

OTHER PUBLICATIONS

EP Extended Search Report in European Appln. No. 18812782.3, dated Feb. 16, 2021, 10 pages.
Kula et al., "T-Scan: a genome-wide method for the systematic discovery of T cell epitopes," Cell, Aug. 8, 2019, 178(4):1016-28.
Liesche et al., "Single-fluorescent protein reporters allow parallel quantification of natural killer cell-mediated granzyme and caspase activities in single target cells," Frontiers in Immunology, Aug. 8, 2018, 9:1840.
Packard et al., "Granzyme B activity in target cells detects attack by cytotoxic lymphocytes," The Journal of Immunology, Sep. 15, 2007, 179(6):3812-20.
Vrazo et al., "Live cell evaluation of granzyme delivery and death receptor signaling in tumor cells targeted by human natural killer cells," Blood, The Journal of the American Society of Hematology, Aug. 20, 2015, 126(8):e1-0.
AU Office Action in Australian Appln. No. 2018279728, dated Jul. 22, 2022, 5 pages.
Cameron et al., "Identification of a Titin-derived HLA-A1-presented peptide as a cross-reactive target for engineered MAGE A3-directed T cells," Science Translational Medicine, Aug. 7, 2013, 5(197):197ra103-, 12 pages.
Casciola-Rosen et al., "Mouse and human granzyme B have distinct tetrapeptide specificities and abilities to recruit the bid pathway," Journal of Biological Chemistry, Feb. 16, 2007, 282(7):4545-52.
Chen et al., "Design, synthesis, and biological evaluation of isoquinoline-1, 3, 4-trione derivatives as potent caspase-3 inhibitors," Journal of Medicinal Chemistry, Mar. 9, 2006, 49(5):1613-23.

(Continued)

*Primary Examiner* — Sahana S Kaup
(74) *Attorney, Agent, or Firm* — Fish & Richardson P.C.

(57) ABSTRACT

Described herein, in one aspect, are antigen presenting cells (APCs) comprising an exogenous nucleic acid encoding one or more candidate antigens, wherein the one or more candidate antigens are expressed and presented with MHC class I or MC class II molecules; a molecular reporter of Granzyme B (GzB) activity; and c) an exogenous inhibitor of caspase-activated deoxyribonuclease (CAD)-mediated DNA degradation, a CAD knockout, or a caspase knockout (e.g., caspase 3 knockout). Described herein, in another aspect, is a system for detection of recognized antigen presentation by an antigen presenting cell to a cytotoxic lymphocyte or NK cell.

22 Claims, 28 Drawing Sheets

Specification includes a Sequence Listing.

(56) References Cited

OTHER PUBLICATIONS

Choi et al., "Imaging burst kinetics and spatial coordination during serial killing by single natural killer cells," Proceedings of the National Academy of Sciences, Apr. 16, 2013, 110(16):6488-93.
Chowdhury et al., "Death by a thousand cuts: granzyme pathways of programmed cell death," Annual,. Review of Immunology, Apr. 23, 2008, 26:389-420.
Chu et al., "N-benzylisatin sulfonamide analogues as potent caspase-3 inhibitors: synthesis, in vitro activity, and molecular modeling studies," Journal of Medicinal Chemistry, Dec. 1, 2005, 48(24):7637-47.
Enari et al., "A caspase-activated DNase that degrades DNA during apoptosis, and its inhibitor ICAD," Nature, Jan. 1998, 391(6662):43-50.
Ghorashian et al., "CD8 T cell tolerance to a tumor-associated self-antigen is reversed by CD4 T cells engineered to express the same T cell receptor," The Journal of Immunology, Feb. 1, 2015, 194(3):1080-9.
Han et al., "Selective, reversible caspase-3 inhibitor is neuroprotective and reveals distinct pathways of cell death after neonatal hypoxic-ischemic brain injury," Journal of Biological Chemistry, Aug. 16, 2002, 277(33):30128-36.
Kamiyama et al., "Versatile protein tagging in cells with split fluorescent protein," Nature Communications, Mar. 18, 2016, 7(1):1-9.
Kolowos et al., "Biased TCR repertoire in HIV-1-infected patients due to clonal expansion of HIV-1-reverse transcriptase-specific CTL clones," The Journal of Immunology, Jun. 15, 1999, 162(12):7525-33.
Nilsson et al., "Short cytoplasmic sequences serve as retention signals for transmembrane proteins in the endoplasmic reticulum," Cell, Aug. 25, 1989, 58(4):707-18.
PCT International Preliminary Report on Patentability in International Appln. No. PCT/US2018/036663, dated Dec. 10, 2019, 9 pages.
PCT International Search Report and Written Opinion of International Appln. No. PCT/US2018/036663, dated Dec. 13, 2018, 13 pages.
Rininsland et al., "Granzyme B ELISPOT assay for ex vivo measurements of T cell immunity," Journal of Immunological Methods, Jun. 23, 2000, 240(1-2):143-55.
Sakahira et al., "Cleavage of CAD inhibitor in CAD activation and DNA degradation during apoptosis," Nature, Jan. 1998, 391(6662):96-9.
Sakahira et al., "Enzymatic active site of caspase-activated DNase (CAD) and its inhibition by inhibitor of CAD," Archives of Biochemistry and Biophysics, Apr. 1, 2001, 388(1):91-9.
Schub et al., "CMV-specific TCR-transgenic T cells for immunotherapy. The Journal of Immunology," Nov. 15, 2009, 183(10):6819-30.
Sekaly, "The failed HIV Merck vaccine study: a step back or a launching point for future vaccine development?," The Journal of Experimental Medicine, Jan. 21, 2008, 205(1):7-12.
Tang et al., "Cleavage of DFF-45/ICAD by multiple caspases is essential for its function during apoptosis," Journal of Biological Chemistry, Oct. 30, 1998, 273(44):28549-52.
To et al., "Rationally designed fluorogenic protease reporter visualizes spatiotemporal dynamics of apoptosis in vivo," Proceedings of the National Academy of Sciences, Mar. 17, 2015, 112(11):3338-43.
Uchida et al., "HIV, but not murine leukemia virus, vectors mediate high efficiency gene transfer into freshly isolated G0/G1 human hematopoietic stem cells," Proceedings of the National Academy of Sciences, Sep. 29, 1998, 95(20):11939-44.
Wolf et al., "Caspase-3 is the primary activator of apoptotic DNA fragmentation via DNA fragmentation factor-45/inhibitor of caspase-activated DNase inactivation," Journal of Biological Chemistry, Oct. 22, 1999, 274(43):30651-6.
Xu et al., "Comprehensive serological profiling of human populations using a synthetic human virome," Science, Jun. 5, 2015, 348(6239):aaa0698, 11 pages.
Yik et al., "Cutting edge: single-chain trimers of MHC class I molecules form stable structures that potently stimulate antigen-specific T cells and B cells," The Journal of Immunology, Apr. 1, 2002, 168(7):3145-9.
Yu et al., "An improved monomeric infrared fluorescent protein for neuronal and tumour brain imaging," Nature Communications, May 15, 2014 May, 5(1):1-7.
JP Japanese Office Action in Japanese Appln. No. 2019-567577, dated Apr. 5, 2022, 8 pages (with English translation).
JP Japanese Office Action in Japanese Appln. No. 2019-567577, dated Oct. 4, 2022, 6 pages (with English translation).
CN Office Action in Chinese Appln. No. 201880051295.1, dated Feb. 1, 2023, 17 pages (with English translation).

* cited by examiner

|  | Modified CD8 T cells | | |
|---|---|---|---|
|  | Ob1A.12 TCR | Control IV9 TCR | No TCR |
| Wild Type MBP | 17.2 | 0.9 | 0.4 |
| Mutant MBP #1 (EE) | 0.9 | 0.8 | 0.6 |
| Mutant MBP #2 (AA) | 0.9 | 0.5 | 0.6 |
| Reporter alone | 0.8 | 0.3 | 0.2 |
FIG. 10
FIG. 11
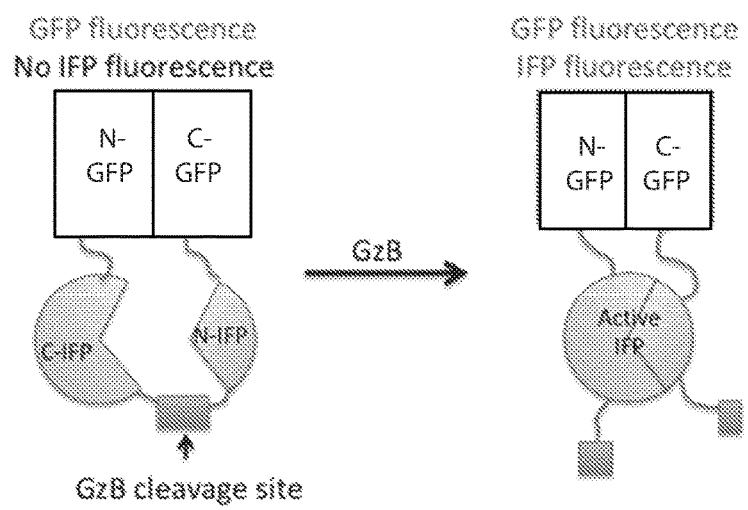
FIG. 12

FIG. 13

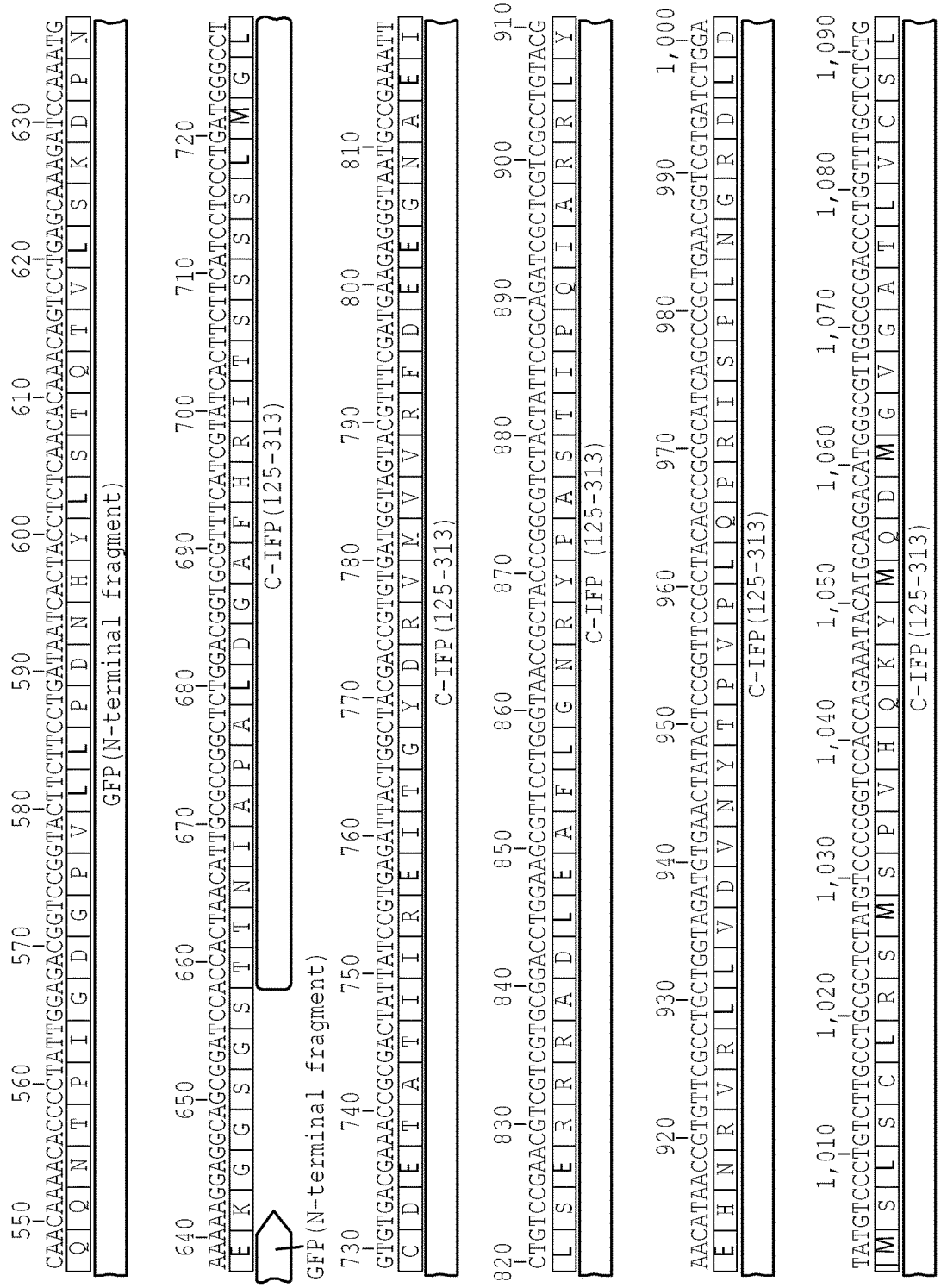
FIG. 13, continued

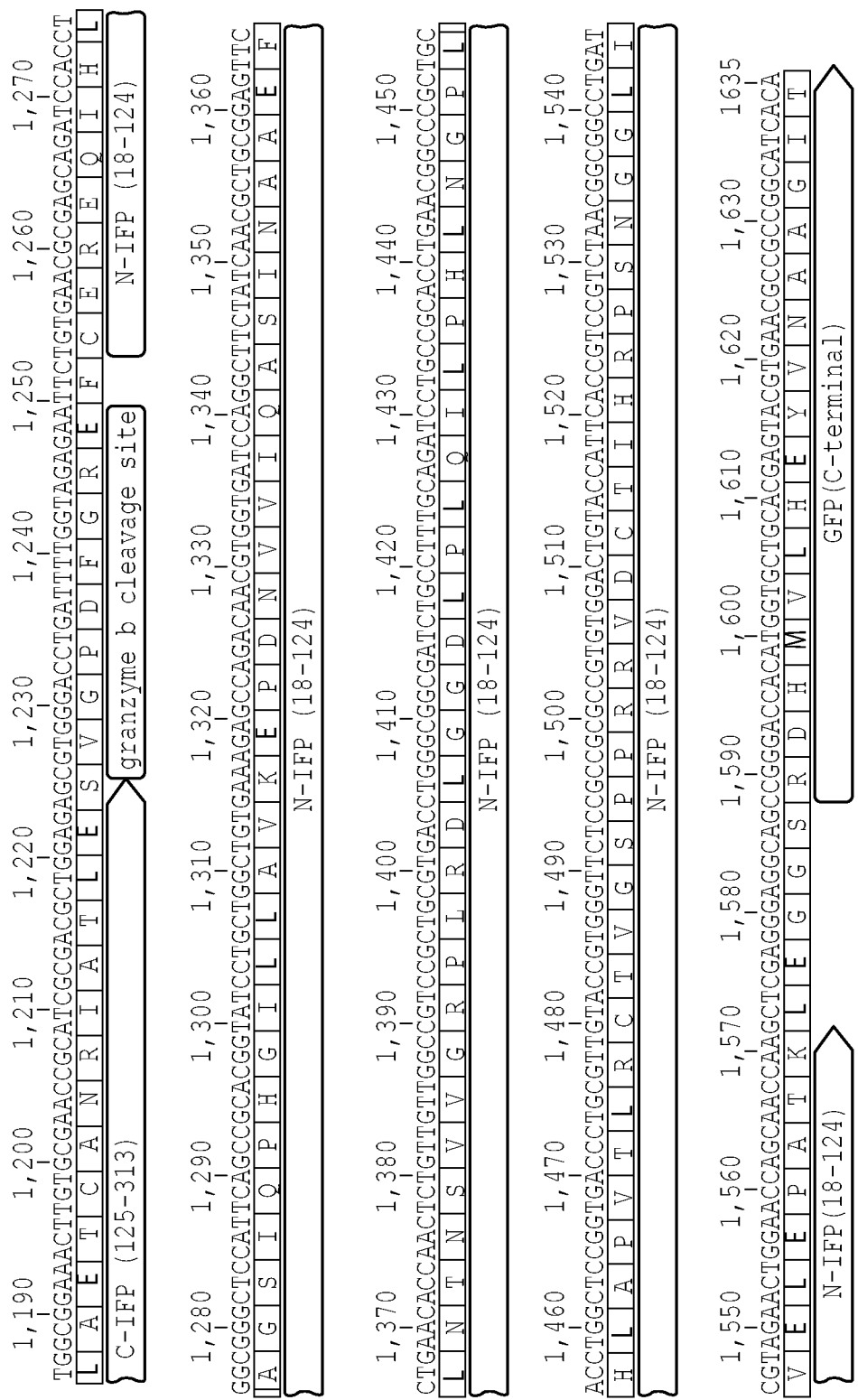
FIG. 13, continued

FIG. 15, continued

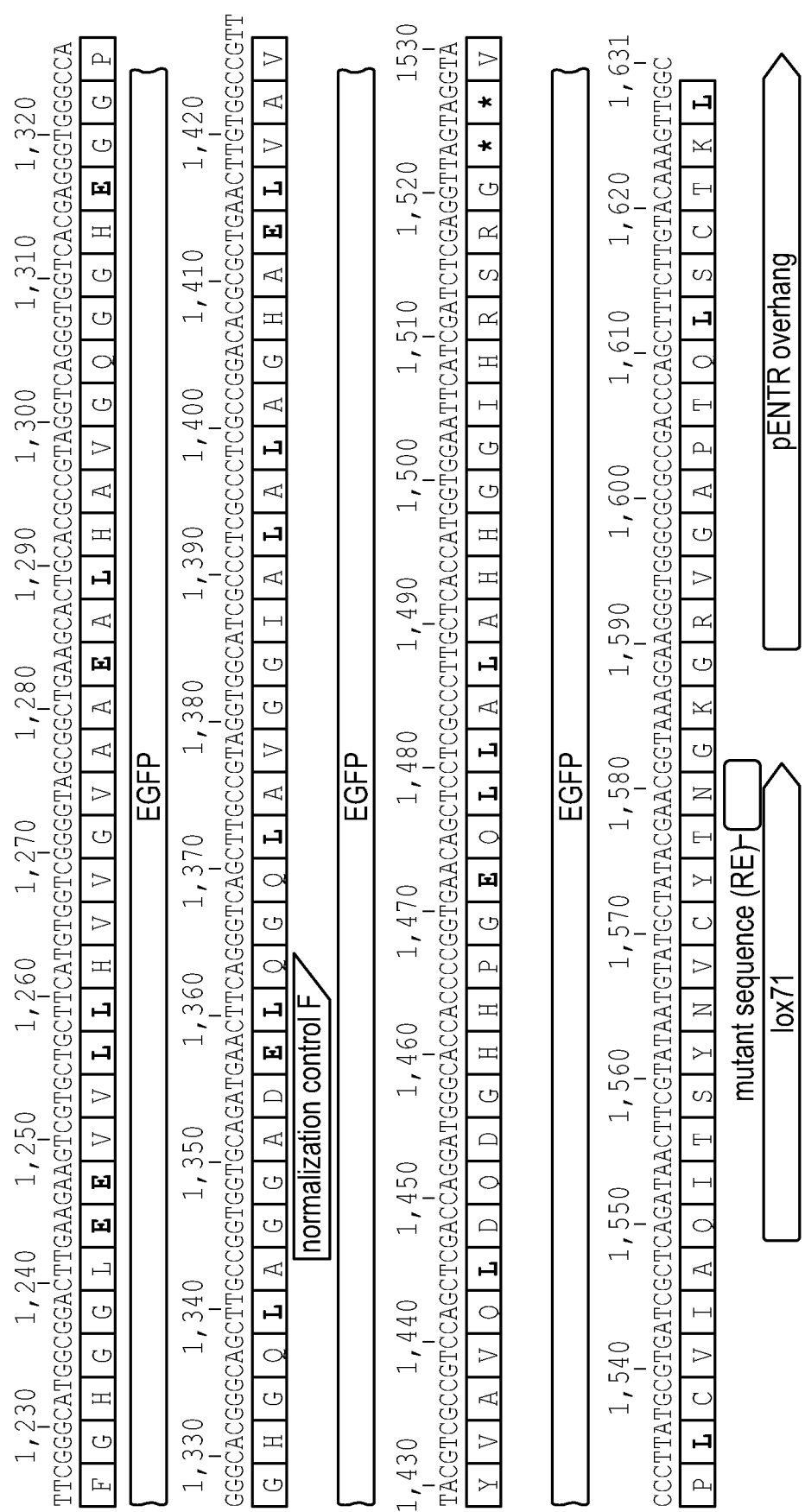
FIG. 15, continued

FIG. 20

SEQUENCE LISTING

<160> NUMBER OF SEQ ID NOS: 32

<210> SEQ ID NO 1
<211> LENGTH: 4
<212> TYPE: PRT
<213> ORGANISM: Artificial Sequence
<220> FEATURE:
<223> OTHER INFORMATION: GzB cleavage site

<400> SEQUENCE: 1

Val Gly Pro Asp
1

<210> SEQ ID NO 2
<211> LENGTH: 1635
<212> TYPE: DNA
<213> ORGANISM: Artificial Sequence
<220> FEATURE:
<223> OTHER INFORMATION: GzB IFP reporter

<400> SEQUENCE: 2

| | |
|---|---|
| atgtccaaag gagaagaact gtttaccggt gttgtgccaa ttttggttga actcgatggt | 60 |
| gatgtcaacg gacataagtt ctcagtgaga ggcgaaggag aaggtgacgc caccattgga | 120 |
| aaattgactc ttaaattcat ctgtactact ggtaaacttc ctgtaccatg gccgactctc | 180 |
| gtaacaacgc ttacgtacgg agttcagtgc ttttcgagat acccagacca tatgaaaaga | 240 |
| catgactttt ttaagtcggc tatgcctgaa ggttacgtgc aagaaagaac aatttcgttc | 300 |
| aaagatgatg gaaaatataa aactagagca gttgttaaat ttgaaggaga tactttggtt | 360 |
| aaccgcattg aactgaaagg aacagatttt aaagaagatg gtaatattct tggacacaaa | 420 |
| ctcgaataca attttaatag tcataacgta tacatcactg ctgataagca aaagaacgga | 480 |
| attaaagcga atttcacagt acgccataat gtagaagatg gcagtgttca acttgccgac | 540 |
| cattaccaac aaaacacccc tattggagac ggtccggtac ttcttcctga taatcactac | 600 |
| ctctcaacac aaacagtcct gagcaaagat ccaaatgaaa aggaggcag cggatccacc | 660 |
| actaacattg cgccggctct ggacggtgcg tttcatcgta tcacttcttc atcctccctg | 720 |
| atgggcctgt gtgacgaaac cgcgactatt atccgtgaga ttactggcta cgaccgtgtg | 780 |
| atggtagtac gtttcgatga agagggtaat gccgaaattc tgtccgaacg tcgtcgtgcg | 840 |
| gacctggaag cgttcctggg taaccgctac ccggcgtcta ctattccgca gatcgctcgt | 900 |
| cgcctgtacg aacataaccg tgttcgcctg ctggtagatg tgaactatac tccggttccg | 960 |
| ctacagccgc gcatcagccc gctgaacggt cgtgatctgg atatgtccct gtcttgcctg | 1020 |
| cgctctatgt ccccggtcca ccagaaatac atgcaggaca tgggcgttgg cgcgaccctg | 1080 |
| gtttgctctc tgatggtgtc tggtcgtttg tggggtctga tcgcttgcca ccactacgaa | 1140 |
| ccgcgcttcg ttccgttcca cattcgcgct gctggcgaag cgctggcgga aacttgtgcg | 1200 |
| aaccgcatcg cgacgctgga gagcgtggga cctgattttg gtagagaatt ctgtgaacgc | 1260 |
| gagcagatcc acctggcggg ctccattcag ccgcacggta tcctgctggc tgtgaaagag | 1320 |
| ccagacaacg tggtgatcca ggcttctatc aacgctgcgg agttcctgaa caccaactct | 1380 |
| gttgttggcc gtccgctgcg tgacctgggc ggcgatctgc ctttgcagat cctgccgcac | 1440 |
| ctgaacggcc cgctgcacct ggctccggtg accctgcgtt gtaccgtggg ttctccgccg | 1500 |
| cgccgtgtgg actgtaccat tcaccgtccg tctaacggcg gcctgatcgt agaactggaa | 1560 |
| ccagcaacca agctcgaggg aggcagccgg gaccacatgg tgctgcacga gtacgtgaac | 1620 |
| gccgccggca tcaca | 1635 |

<210> SEQ ID NO 3
<211> LENGTH: 1631
<212> TYPE: DNA
<213> ORGANISM: Artificial Sequence
<220> FEATURE:
<223> OTHER INFORMATION: GzB IFP reporter

<400> SEQUENCE: 3

| | |
|---|---|
| gccgccccct tcaccatcca taacttcgta tagcatacat tatacgaacg gtaatctgaa | 60 |
| agcttgccac catggatagc actgagaacg tcatcaagcc cttcatgcgc ttcaaggtgc | 120 |

-continued

```
acatggaggg ctccgtgaac ggccacgagt tcgagatcga gggcgtgggc gagggcaagc    180
cctacgaggg cacccagacc gccaagctgc aagtgaccaa gggcggcccc ctgcccttcg    240
cctgggacat cctgtccccc cagttcttct acggctccaa ggcgtacatc aagcaccccg    300
ccgacatccc cgactacctc aagcagtcct tccccgaggg cttcaagtgg agcgcgtgga    360
tgaacttcga ggacggcggc gtggtgaccg tgacccagga ctcctccctg caggacggca    420
ccctcatcta ccacgtgaag ttcatcggcg tgaacttccc ctccgacggc ccgtaatgc     480 agaagaagac tctgggctgg agccctcca ctgagcgcaa ctaccccgc gacggcgtgc      540 tgaagggcga gaaccacatg cgctgaagc tgaaggcgg cggccactac ctgtgtgagt      600
tcaagtccat ctacatggcc aagaagcccg tgaagctgcc cggctaccac tacgtggact    660
acaagctcga catcacctcc cacaacgagg actacaccgt ggtggagcag tacgagcgcg    720
ccgaggcccg ccaccacctg ttccagtagg gatccgccgc caccatggga ggaattctta    780
cttgtacagc tcgtccatgc cgagagtgat cccggcggcg gtcacgaact ccagcaggac    840
catgtgatcg cgcttctcgt tggggtcttt gctcagggcg gactgggtgc tcaggtagtg    900
gttgtcgggg agcagcacgg ggccgtcgcc gatgggggtg ttctgctggt agtggtcggc    960
gagctgcacg ctgccgtcct cgatgttgtg gcggatcttg aagttcacct tgatgccgtt   1020
cttctgcttg tcggccatga tatagacgtt gtggctgttg tagttgtact ccagcttgtg   1080
ccccaggatg ttgccgtcct ccttgaagtc gatgcccttc agctcgatgc ggttcaccag   1140
ggtgtcgccc tcgaacttca cctcggcgcg gtcttgtag ttgccgtcgt ccttgaagaa    1200
gatggtgcgc tcctggacgt agccttcggg catggcggac ttgaagaagt cgtgctgctt   1260
catgtggtcg gggtagcggc tgaagcactg cacgccgtag gtcagggtgg tcacgagggt   1320
gggccagggc acgggcagct gccggtggt gcagatgaac ttcagggtca gcttgccgta    1380
ggtggcatcg ccctcgccct cgccggacac gctgaacttg tggccgttta cgtcgccgtc   1440
cagctcgacc aggatgggca ccaccccggt gaacagctcc tcgcccttgc tcaccatggt   1500
ggaattcatc gatctcgagg ttagtaggta cccttatgcg tgatcgctca gataacttcg   1560
tataatgtat gctatacgaa cggtaaagga agggtgggcg cgccgaccca gctttcttgt   1620
acaaagttgg c                                                       1631
```

<210> SEQ ID NO 4
<211> LENGTH: 9
<212> TYPE: PRT
<213> ORGANISM: Artificial Sequence
<220> FEATURE:
<223> OTHER INFORMATION: known target of the NLV2 TCR

<400> SEQUENCE: 4

Asn Leu Val Pro Met Val Ala Thr Val
1               5

<210> SEQ ID NO 5
<211> LENGTH: 331
<212> TYPE: PRT
<213> ORGANISM: Artificial Sequence
<220> FEATURE:
<223> OTHER INFORMATION: exemplary mature ICAD sequence

<400> SEQUENCE: 5

Met Glu Val Thr Gly Asp Ala Gly Val Pro Glu Ser Gly Glu Ile Arg
1               5                   10                  15

-continued

```
Thr Leu Lys Pro Cys Leu Leu Arg Arg Asn Tyr Ser Arg Glu Gln His
             20                  25                  30

Gly Val Ala Ala Ser Cys Leu Glu Asp Leu Arg Ser Lys Ala Cys Asp
         35                  40                  45

Ile Leu Ala Ile Asp Lys Ser Leu Thr Pro Val Thr Leu Val Leu Ala
 50                  55                  60

Glu Asp Gly Thr Ile Val Asp Asp Asp Tyr Phe Leu Cys Leu Pro
65                  70                  75                  80

Ser Asn Thr Lys Phe Val Ala Leu Ala Ser Asn Glu Lys Trp Ala Tyr
             85                  90                  95

Asn Asn Ser Asp Gly Gly Thr Ala Trp Ile Ser Gln Glu Ser Phe Asp
        100                 105                 110

Val Asp Glu Thr Asp Ser Gly Ala Gly Leu Lys Trp Lys Asn Val Ala
        115                 120                 125

Arg Gln Leu Lys Glu Asp Leu Ser Ser Ile Ile Leu Leu Ser Glu Glu
130                 135                 140

Asp Leu Gln Met Leu Val Asp Ala Pro Cys Ser Asp Leu Ala Gln Glu
145                 150                 155                 160

Leu Arg Gln Ser Cys Ala Thr Val Gln Arg Leu Gln His Thr Leu Gln
             165                 170                 175

Gln Val Leu Asp Gln Arg Glu Glu Val Arg Gln Ser Lys Gln Leu Leu
        180                 185                 190

Gln Leu Tyr Leu Gln Ala Leu Glu Lys Glu Gly Ser Leu Leu Ser Lys
             195                 200                 205

Gln Glu Glu Ser Lys Ala Ala Phe Gly Glu Val Asp Ala Val Asp
210                 215                 220

Thr Gly Ile Ser Arg Glu Thr Ser Ser Asp Val Ala Leu Ala Ser His
225                 230                 235                 240

Ile Leu Thr Ala Leu Arg Glu Lys Gln Ala Pro Glu Leu Ser Leu Ser
             245                 250                 255

Ser Gln Asp Leu Glu Leu Val Thr Lys Glu Asp Pro Lys Ala Leu Ala
        260                 265                 270

Val Ala Leu Asn Trp Asp Ile Lys Lys Thr Glu Thr Val Gln Glu Ala
        275                 280                 285

Cys Glu Arg Glu Leu Ala Leu Arg Leu Gln Gln Thr Gln Ser Leu His
290                 295                 300

Ser Leu Arg Ser Ile Ser Ala Ser Lys Ala Ser Pro Pro Gly Asp Leu
305                 310                 315                 320

Gln Asn Pro Lys Arg Ala Arg Gln Asp Pro Thr
             325                 330
```

<210> SEQ ID NO 6
<211> LENGTH: 4
<212> TYPE: PRT
<213> ORGANISM: Artificial Sequence
<220> FEATURE:
<223> OTHER INFORMATION: GzB cleavage

<400> SEQUENCE: 6

Ile Glu Thr Asp
1

<210> SEQ ID NO 7
<211> LENGTH: 67
<212> TYPE: PRT
<213> ORGANISM: Artificial Sequence
<220> FEATURE:

-continued

<223> OTHER INFORMATION: plasma membrane attachment peptide

<400> SEQUENCE: 7

```
Met Gly Val Lys Val Leu Phe Ala Leu Ile Cys Ile Ala Val Ala Glu
1               5                   10                  15
Ala Ser Ser Gly Ser Ser Gly Asp Tyr Lys Asp Asp Asp Lys Pro
            20                  25                  30
Val Gln Pro Met Ala Leu Ile Val Leu Gly Gly Val Ala Gly Leu Leu
        35                  40                  45
Leu Phe Ile Gly Leu Gly Ile Phe Phe Cys Val Arg Cys Arg His Arg
    50                  55                  60
Arg Arg Gln
65
```

<210> SEQ ID NO 8
<211> LENGTH: 23
<212> TYPE: PRT
<213> ORGANISM: Artificial Sequence
<220> FEATURE:
<223> OTHER INFORMATION: membrane attachment signal peptide

<400> SEQUENCE: 8

```
Met Ala Leu Pro Val Thr Ala Leu Leu Leu Pro Leu Ala Leu Leu Leu
1               5                   10                  15
His Ala Ala Arg Pro Ser Gln
            20
```

<210> SEQ ID NO 9
<211> LENGTH: 7
<212> TYPE: PRT
<213> ORGANISM: Artificial Sequence
<220> FEATURE:
<223> OTHER INFORMATION: GzB cleavage sequence

<400> SEQUENCE: 9

```
Val Gly Pro Asp Phe Gly Arg
1               5
```

<210> SEQ ID NO 10
<211> LENGTH: 8
<212> TYPE: PRT
<213> ORGANISM: Artificial Sequence
<220> FEATURE:
<223> OTHER INFORMATION: flag tag

<400> SEQUENCE: 10

```
Asp Tyr Lys Asp Asp Asp Asp Lys
1               5
```

<210> SEQ ID NO 11
<211> LENGTH: 9
<212> TYPE: PRT
<213> ORGANISM: Artificial Sequence
<220> FEATURE:
<223> OTHER INFORMATION: HA tag

<400> SEQUENCE: 11

```
Tyr Pro Tyr Asp Val Pro Asp Tyr Ala
1               5
```

<210> SEQ ID NO 12
<211> LENGTH: 56
<212> TYPE: PRT
<213> ORGANISM: Artificial Sequence

```
<220> FEATURE:
<223> OTHER INFORMATION: 56 aa fragment containing the IV9 epitope

<400> SEQUENCE: 12

Gly Ala Lys Ala Leu Thr Asp Ile Val Pro Leu Thr Arg Glu Ala Glu
1               5                   10                  15

Leu Glu Leu Ala Glu Asn Lys Glu Ile Leu Lys Glu Pro Val His Gly
            20                  25                  30

Val Tyr Tyr Asp Ser Ala Lys Glu Leu Ile Ala Glu Val Gln Lys Gln
        35                  40                  45

Gly Leu Asp Gln Trp Thr Tyr Gln
    50                  55

<210> SEQ ID NO 13
<211> LENGTH: 46
<212> TYPE: DNA
<213> ORGANISM: Artificial Sequence
<220> FEATURE:
<223> OTHER INFORMATION: primer HIV_lib_F

<400> SEQUENCE: 13
ggggacaagt ttgtacaaaa aagcaggctc aagaattctc cgtggc           46

<210> SEQ ID NO 14
<211> LENGTH: 54
<212> TYPE: DNA
<213> ORGANISM: Artificial Sequence
<220> FEATURE:
<223> OTHER INFORMATION: primer HIV_lib_R

<400> SEQUENCE: 14
ggggaccact ttgtacaaga aagctgggtc agctagttac actcgagagc tcac    54

<210> SEQ ID NO 15
<211> LENGTH: 59
<212> TYPE: DNA
<213> ORGANISM: Artificial Sequence
<220> FEATURE:
<223> OTHER INFORMATION: primer T_cell_PCR1_F

<400> SEQUENCE: 15
ccagtcaggt gtgatgctcg gggatccagg aattcagttt gtacaaaaaa gcaggctca  59

<210> SEQ ID NO 16
<211> LENGTH: 46
<212> TYPE: DNA
<213> ORGANISM: Artificial Sequence
<220> FEATURE:
<223> OTHER INFORMATION: primer T_cell_PCR1_R

<400> SEQUENCE: 16
cgagcttatc gtcgtcatcc ccactttgta caagaaagct gggtca           46

<210> SEQ ID NO 17
<211> LENGTH: 4
<212> TYPE: PRT
<213> ORGANISM: Artificial Sequence
<220> FEATURE:
<223> OTHER INFORMATION: C-terminal motif

<400> SEQUENCE: 17

Lys Lys Tyr Leu
1
```

```
<210> SEQ ID NO 18
<211> LENGTH: 2266
<212> TYPE: DNA
<213> ORGANISM: Artificial Sequence
<220> FEATURE:
<223> OTHER INFORMATION: KKXX reporter sequence

<400> SEQUENCE: 18
```

| | | | | | |
|---|---|---|---|---|---|
| ggggacaagt | ttgtacaaaa | aagcaggctc | aggaattctc | accatgaacc | ggggagtccc | 60 |
| ttttaggcac | ttgcttctgg | tgctgcaact | ggcgctcctc | ccagcagcca | ctcagggaaa | 120 |
| gaaagtggtg | ctgggcaaaa | aaggggatac | agtggaactg | acctgtacag | cttcccagaa | 180 |
| gaagagcata | caattccact | ggaaaaactc | caaccagata | aagattctgg | gaaatcaggg | 240 |
| ctccttctta | actaaaggtc | catccaagct | gaatgatcgc | gctgactcaa | gaagaagcct | 300 |
| tgggaccaa | ggaaacttcc | ccctgatcat | caagaatctt | aagatagaag | actcagatac | 360 |
| ttacatctgt | gaagtggagg | accagaagga | ggaggtgcaa | ttgctagtgt | tcggattgac | 420 |
| tgccaactct | gacacccacc | tgcttcaggg | gcagagcctg | accctgacct | ggagagccc | 480 |
| ccctggtagt | agcccctcag | tgcaatgtag | gagtccaagg | ggtaaaaaca | tacaggggg | 540 |
| gaagaccctc | tccgtgtctc | agctggagct | ccaggatagt | ggcacctgga | catgcactgt | 600 |
| cttgcagaac | cagaagaagg | tggagttcaa | aatagacatc | gtggtgctag | ctttccagaa | 660 |
| ggcctccagc | atagtctata | agaaagaggg | ggaacaggtg | gagttctcct | tcccactcgc | 720 |
| ctttacagtt | gaaaagctga | cggggcagtgg | cgagctgtgg | tggcaggcgg | agagggcttc | 780 |
| ctcctccaag | tcttggatca | cctttgacct | gaagaacaag | gaagtgtctg | taaaacgggt | 840 |
| tacccaggac | cctaagctcc | agatgggcaa | gaagctcccg | ctccacctca | ccctgccccca | 900 |
| ggccttgcct | cagtatgctg | gctctggaaa | cctcaccctg | gcccttgaag | cgaaaacagg | 960 |
| aaagttgcat | caggaagtga | acctggtggt | gatgagagcc | actcagctcc | agaaaaattt | 1020 |
| gacctgtgag | gtgtggggac | ccacctcccc | taagctgatg | ctgagcttga | aactggagaa | 1080 |
| caaggaggca | aaggtctcga | agcgggagaa | ggcggtgtgg | gtgctgaacc | ctgaggcggg | 1140 |
| gatgtggcag | tgtctgctga | gtgactcggg | acaggtcctg | ctggaatcca | acatcaaggt | 1200 |
| tctgcccaca | tggtccaccc | cggtgcagcc | aatggccctg | attgtgctgg | ggggcgtcgc | 1260 |
| cggcctcctg | cttttcattg | gctaggcat | cttcttctgt | gtcaggtgcc | ggcaccgaag | 1320 |
| gcgccaagca | gagcggatgt | ctcagatcaa | gagactcctc | agtgagaaga | agacctgcca | 1380 |
| gtgccctcac | cggtttcaga | agacatgtag | ccccattggc | ggccgcatgg | tgagcaaggg | 1440 |
| cgaggagctg | ttcaccgggg | tggtgcccat | cctggtcgag | ctggacgcg | acgtaaacgg | 1500 |
| ccacaagttc | agcgtgtccg | gcgagggcga | gggcgatgcc | acctacggca | agctgaccct | 1560 |
| gaagttcatc | tgcaccaccg | gcaagctgcc | cgtgccctgg | cccaccctcg | tgaccaccct | 1620 |
| gacctacggc | gtgcagtgct | tcagccgcta | ccccgaccac | atgaagcagc | acgacttctt | 1680 |
| caagtccgcc | atgcccgaag | gctacgtcca | ggagcgcacc | atcttcttca | aggacgacgg | 1740 |
| caactacaag | acccgcgccg | aggtgaagtt | cgagggcgac | accctggtga | accgcatcga | 1800 |
| gctgaagggc | atcgacttca | aggaggacgg | caacatcctg | gggcacaagc | tggagtacaa | 1860 |
| ctacaacagc | cacaacgtct | atatcatggc | cgacaagcag | aagaacggca | tcaaggtgaa | 1920 |
| cttcaagatc | cgccacaaca | tcgaggacgg | cagcgtgcag | ctcgccgacc | actaccagca | 1980 |
| gaacaccccc | atcggcgacg | gccccgtgct | gctgcccgac | aaccactacc | tgagcaccca | 2040 |
| gtccgccctg | agcaaagacc | ccaacgagaa | gcgcgatcac | atggtcctgc | tggagttcgt | 2100 |

```
gaccgccgcc gggatcactc tcggcatgga cgagctgtac aagcttgtag gaccagactt    2160
cgggcgcgag aacctgtact tccagtctag aactctggcc agctccctga ctttcaagaa    2220
gtatctgtaa ctagctgacc cagctttctt gtacaaagtg gtcccc                   2266
```

<210> SEQ ID NO 19
<211> LENGTH: 56
<212> TYPE: PRT
<213> ORGANISM: Artificial Sequence
<220> FEATURE:
<223> OTHER INFORMATION: ORFL205C_(UL83) (pp65)

<400> SEQUENCE: 19

```
His Asn Pro Ala Val Phe Thr Trp Pro Pro Trp Gln Ala Gly Ile Leu
1               5                   10                  15

Ala Arg Asn Leu Val Pro Met Val Ala Thr Val Gln Gly Gln Asn Leu
            20                  25                  30

Lys Tyr Gln Glu Phe Phe Trp Asp Ala Asn Asp Ile Tyr Arg Ile Phe
        35                  40                  45

Ala Glu Leu Glu Gly Val Trp Gln
    50                  55
```

<210> SEQ ID NO 20
<211> LENGTH: 56
<212> TYPE: PRT
<213> ORGANISM: Artificial Sequence
<220> FEATURE:
<223> OTHER INFORMATION: ORFL205C_(UL83) (pp65)

<400> SEQUENCE: 20

```
Gly Val Met Thr Arg Gly Arg Leu Lys Ala Glu Ser Thr Val Ala Pro
1               5                   10                  15

Glu Glu Asp Thr Asp Glu Asp Ser Asp Asn Glu Ile His Asn Pro Ala
            20                  25                  30

Val Phe Thr Trp Pro Pro Trp Gln Ala Gly Ile Leu Ala Arg Asn Leu
        35                  40                  45

Val Pro Met Val Ala Thr Val Gln
    50                  55
```

<210> SEQ ID NO 21
<211> LENGTH: 56
<212> TYPE: PRT
<213> ORGANISM: Artificial Sequence
<220> FEATURE:
<223> OTHER INFORMATION: ORFL264C_ (UL123)

<400> SEQUENCE: 21

```
Glu Thr Met Cys Asn Glu Tyr Lys Val Thr Ser Asp Ala Cys Met Met
1               5                   10                  15

Thr Met Tyr Gly Gly Ile Ser Leu Leu Ser Glu Phe Cys Arg Val Leu
            20                  25                  30

Cys Cys Tyr Val Leu Glu Glu Thr Ser Val Met Leu Ala Lys Arg Pro
        35                  40                  45

Leu Ile Thr Lys Pro Glu Val Ile
    50                  55
```

<210> SEQ ID NO 22
<211> LENGTH: 56
<212> TYPE: PRT
<213> ORGANISM: Artificial Sequence
<220> FEATURE:
<223> OTHER INFORMATION: ORFL264C_ (UL123)

<400> SEQUENCE: 22

Cys Arg Val Leu Cys Cys Tyr Val Leu Glu Glu Thr Ser Val Met Leu
1               5                   10                  15

Ala Lys Arg Pro Leu Ile Thr Lys Pro Glu Val Ile Ser Val Met Lys
                20                  25                  30

Arg Arg Ile Glu Glu Ile Cys Met Lys Val Phe Ala Gln Tyr Ile Leu
            35                  40                  45

Gly Ala Asp Pro Leu Arg Val Cys
        50                  55

<210> SEQ ID NO 23
<211> LENGTH: 56
<212> TYPE: PRT
<213> ORGANISM: Artificial Sequence
<220> FEATURE:
<223> OTHER INFORMATION: ORFS333C_(US8)

<400> SEQUENCE: 23

Asp Tyr Tyr Tyr Tyr Arg Glu Asp Glu Pro Arg Gln His Gly Glu Pro
1               5                   10                  15

Asn Tyr Val Ala Pro Pro Ala Arg Gln Phe Arg Phe Pro Pro Leu Asn
                20                  25                  30

Asn Val Ser Ser Tyr Gln Ala Ser Cys Val Val Lys Asp Gly Val Leu
            35                  40                  45

Asp Ala Val Trp Arg Val Gln Gly
        50                  55

<210> SEQ ID NO 24
<211> LENGTH: 56
<212> TYPE: PRT
<213> ORGANISM: Artificial Sequence
<220> FEATURE:
<223> OTHER INFORMATION: ORFS333C_(US8)

<400> SEQUENCE: 24

Pro Pro Leu Asn Asn Val Ser Ser Tyr Gln Ala Ser Cys Val Val Lys
1               5                   10                  15

Asp Gly Val Leu Asp Ala Val Trp Arg Val Gln Gly Thr Phe Tyr Pro
                20                  25                  30

Glu Lys Gly Ile Val Ala Arg Val Gly Trp Ser Gly Arg Arg Gly Arg
            35                  40                  45

Lys Trp Gly Arg Leu His Ala Pro
        50                  55

<210> SEQ ID NO 25
<211> LENGTH: 56
<212> TYPE: PRT
<213> ORGANISM: Artificial Sequence
<220> FEATURE:
<223> OTHER INFORMATION: ORFL232C_(UL100)

<400> SEQUENCE: 25

Val Ser Met Val Thr Gln Tyr Arg Ser Tyr Lys Arg Ser Leu Phe Phe
1               5                   10                  15

Phe Ser Arg Leu His Pro Lys Leu Lys Gly Thr Val Gln Phe Arg Thr
                20                  25                  30

Leu Ile Val Asn Leu Val Glu Val Ala Leu Gly Phe Asn Thr Thr Val
            35                  40                  45

Val Ala Met Ala Leu Cys Tyr Gly

<210> SEQ ID NO 26
<211> LENGTH: 56
<212> TYPE: PRT
<213> ORGANISM: Artificial Sequence
<220> FEATURE:
<223> OTHER INFORMATION: ORFL232C_(UL100)

<400> SEQUENCE: 26

```
Gln Phe Arg Thr Leu Ile Val Asn Leu Val Glu Val Ala Leu Gly Phe
1               5                   10                  15

Asn Thr Thr Val Val Ala Met Ala Leu Cys Tyr Gly Phe Gly Asn Asn
            20                  25                  30

Phe Phe Val Arg Thr Gly His Met Val Leu Ala Val Phe Val Val Tyr
        35                  40                  45

Ala Ile Ile Ser Ile Ile Tyr Phe
    50                  55
```

<210> SEQ ID NO 27
<211> LENGTH: 56
<212> TYPE: PRT
<213> ORGANISM: Artificial Sequence
<220> FEATURE:
<223> OTHER INFORMATION: ORFL321W

<400> SEQUENCE: 27

```
Ser Thr Asp Ser Asp Gly Lys Ser Ile Ile Ala Gly Val Gln Val Val
1               5                   10                  15

Asp His Asp Glu Asp Ile Ile Ala Pro Gln Ser Leu Trp Cys Thr Ala
            20                  25                  30

Phe Lys Glu Ala Leu Trp Asp Val Ala Leu Leu Glu Val Pro Arg Trp
        35                  40                  45

Ala Trp Gln Gly Trp Lys Arg Trp
    50                  55
```

<210> SEQ ID NO 28
<211> LENGTH: 56
<212> TYPE: PRT
<213> ORGANISM: Artificial Sequence
<220> FEATURE:
<223> OTHER INFORMATION: ORFL321W

<400> SEQUENCE: 28

```
Trp Cys Thr Ala Phe Lys Glu Ala Leu Trp Asp Val Ala Leu Leu Glu
1               5                   10                  15

Val Pro Arg Trp Ala Trp Gln Gly Trp Lys Arg Trp Arg Asn Ser Glu
            20                  25                  30

Ser Gly Arg Arg Trp Ser Ala Gly Ser Ala Ser Ala Ser Ser Leu Ser
        35                  40                  45

Asp Leu Ala Gly Glu Ala Val Gly
    50                  55
```

<210> SEQ ID NO 29
<211> LENGTH: 56
<212> TYPE: PRT
<213> ORGANISM: Artificial Sequence
<220> FEATURE:
<223> OTHER INFORMATION: ORFL117C_(UL46)

<400> SEQUENCE: 29

```
Val Glu Phe Glu Ala Gln Pro Gly Ala Leu Leu Ile Arg Met Glu Thr
```

```
                1               5                  10                 15
Gly Cys Asp Ser Pro Arg His Leu Tyr Ile Ser Leu Tyr Leu Leu Gly
                20                 25                 30

Ile Arg Ala Ser Asn Val Ser Ala Ser Thr Arg Cys Leu Leu Glu Ser
        35                 40                 45

Val Tyr Thr Ala Ser Ala Ala Arg
        50                 55
```

<210> SEQ ID NO 30
<211> LENGTH: 56
<212> TYPE: PRT
<213> ORGANISM: Artificial Sequence
<220> FEATURE:
<223> OTHER INFORMATION: ORFL117C_(UL46)

<400> SEQUENCE: 30

```
Tyr Leu Leu Gly Ile Arg Ala Ser Asn Val Ser Ala Ser Thr Arg Cys
1               5                   10                  15

Leu Leu Glu Ser Val Tyr Thr Ala Ser Ala Ala Arg Ala Ala Leu Gln
                20                  25                  30

Trp Leu Asp Leu Gly Pro His Leu Leu His Arg Arg Leu Glu Thr Leu
        35                  40                  45

Gly Cys Val Lys Thr Val Ser Leu
        50                  55
```

<210> SEQ ID NO 31
<211> LENGTH: 56
<212> TYPE: PRT
<213> ORGANISM: Artificial Sequence
<220> FEATURE:
<223> OTHER INFORMATION: ORFL92C_(UL32)

<400> SEQUENCE: 31

```
Leu Ala Arg Ile Gln Glu Arg Cys Lys Leu Leu Val Lys Glu Leu Arg
1               5                   10                  15

Met Cys Leu Ser Phe Asp Ser Asn Tyr Cys Arg Asn Ile Leu Lys His
                20                  25                  30

Ala Val Glu Asn Gly Asp Ser Ala Asp Thr Leu Leu Glu Leu Leu Ile
        35                  40                  45

Glu Asp Phe Asp Ile Tyr Val Asp
        50                  55
```

<210> SEQ ID NO 32
<211> LENGTH: 56
<212> TYPE: PRT
<213> ORGANISM: Artificial Sequence
<220> FEATURE:
<223> OTHER INFORMATION: ORFL92C_(UL32)

<400> SEQUENCE: 32

```
Ile Leu Lys His Ala Val Glu Asn Gly Asp Ser Ala Asp Thr Leu Leu
1               5                   10                  15

Glu Leu Leu Ile Glu Asp Phe Asp Ile Tyr Val Asp Ser Phe Pro Gln
                20                  25                  30

Ser Ala His Thr Phe Leu Gly Ala Arg Ser Pro Ser Leu Glu Phe Asp
        35                  40                  45

Asp Asp Ala Asn Leu Leu Ser Leu
        50                  55
```

METHODS AND COMPOSITIONS FOR IDENTIFYING EPITOPES

CLAIM OF PRIORITY

This application is a § 371 National Stage Application of PCT/US2018/036663, filed Jun. 8, 2018, which claims the benefit of U.S. Provisional Patent Application Ser. No. 62/516,977, filed on Jun. 8, 2017. The entire contents of the foregoing are hereby incorporated by reference.

GOVERNMENT RIGHTS

This invention was made with government support under Grant No. AI116833 awarded by the National Institutes of Health. The government has certain rights in the invention.

TECHNICAL FIELD

Described herein are methods and reagents for identifying target antigens specific to T cells, such as cytotoxic T cells.

BACKGROUND

Immunotherapy approaches based on cell-mediated immune responses can be effective in treating diseases such as cancer, autoimmune diseases, infectious diseases etc. However, antigens that are expressed by the disease-causing cells and play a role in modulating an immune response are challenging to identify. Accordingly, there is a need for methods for identifying target antigens specific to T cells so as to develop therapies and vaccines against the diseases.

SUMMARY

Described herein, in one aspect, are antigen presenting cells (APCs) comprising a) an exogenous nucleic acid encoding one or more candidate antigens, wherein the one or more candidate antigens are expressed and presented with MHC class I or MHC class II molecules; b) a molecular reporter of Granzyme B (GzB) activity; and c) an exogenous inhibitor of caspase-activated deoxyribonuclease (CAD)-mediated DNA degradation, a CAD knockout, or a caspase knockout (e.g., caspase 3 knockout).

Numerous embodiments are further provided that can be applied to any aspect of the present invention and/or combined with any other embodiment described herein. For example, in various embodiments, the exogenous nucleic acid is stably introduced into the genome of the APC, optionally via a lentiviral vector, a retroviral vector, or a transposon. In various embodiments, the exogenous nucleic acid is flanked on each side by predetermined primer recognition sequences. In various embodiments, the molecular reporter of GzB activity comprises a fusion polypeptide comprising a GzB cleavage site (VGPD, SEQ ID NO:1) linked to a detection molecule, such as wherein the molecular reporter comprises a modified infrared fluorescent protein, a membrane tethered CRE recombinase, an antibody-based reporter of GzB activity, an ER retention-based reporter of GzB activity, a cell surface detectable-based reporter of GzB activity, or combinations thereof. In various embodiments, the molecular reporter comprises a membrane tethered CRE recombinase, and the APC further comprises an inverted CRE reporter flanked by LoxP sites, optionally wherein the exogenous nucleic acid is located proximal to a CRE activated primer recognition sequence. In various embodiments, the exogenous inhibitor of CAD-mediated DNA degradation is a nucleic acid encoding inhibitor of caspase-activated deoxyribonuclease (ICAD) gene in expressible form; an inhibitory nucleic acid targeting CAD or caspase 3; a small molecule inhibitor of caspase 3; a chemical DNAse inhibitor; or a peptide or protein inhibitor of caspase 3, or the caspase knockout is a caspase 3 knockout. In various embodiments, the APC i) does not express an endogenous MHC molecule and is engineered to express an exogenous MHC molecule and/or ii) is selected from the group consisting of a K 562 cell, a HEK 293 cell, a HEK 293 T cell, a U2OS cell, a MelJuso cell, a MDA-MB231 cell, a MCF7 cell, a NTERA2 cell, a LN229 cell, a dendritic cell, and a primary autologous B cell. In various embodiments, the candidate antigen is less than or equal to 8, 9, 10, 11, 20, 30, 50, 100, 200, or 300 amino acids in length. In various embodiments, the candidate antigen is greater than 300 amino acids in length. In various embodiments, the exogenous nucleic acid encoding a candidate antigen is derived from an infectious organism or human DNA. In various embodiments, the human DNA is obtained from a cancer cell. In various embodiments, infectious organism is selected from the group consisting of a virus, a bacteria, a fungi, a protozoa, and a multicellular parasitic organism.

Described herein, in another aspect, is a library of APCs, such as APC described above, wherein the respective APCs comprise different exogenous nucleic acids that encode a candidate antigen to thereby represent a library of candidate antigens expressed and presented with MHC Class I and/or MHC Class II molecules.

As described above, numerous embodiments are further provided that can be applied to any aspect of the present invention and/or combined with any other embodiment described herein. For example, in various embodiments, the exogenous nucleic acids are derived from an infectious agent or human DNA. In various embodiments, the library comprises from about $10^2$- to about $10^{14}$ individual candidate antigens.

Described herein, in another aspect, is a molecular reporter of Granzyme B activity, comprising a fusion polypeptide comprising a GzB cleavage site (VGPD, SEQ ID NO:1) linked to a detection molecule.

As described above, numerous embodiments are further provided that can be applied to any aspect of the present invention and/or combined with any other embodiment described herein. For example, in various embodiments, the reporter does not include a pair of fluorochromes that form a FRET pair, or wherein one of the fluorophores is quenched; is not an intact fluorophore, e.g., is not a complete protein capable of fluorescing on its own; and/or is not a leuco dye, e.g., is not a dye that can switch between two chemical forms; one of which is colorless. In various embodiments, the detection molecule is an enzyme, a detectable label, an antibody-binding antigen, or an affinity tag. In various embodiments, the detectable label is detectable after GzB cleavage selected from the group consisting of an infrared fluorescent protein (IFP), a nucleic acid amplification target, a composition recognized by an antibody, a composition that is released from the ER, and a composition present at the cell surface. In various embodiments, the IFP comprises a N-fragment (N-IFP) and a C-fragment (C-IFP), functionally separated by the GzB cleavage site, and is further flanked by an N-fragment of green fluorescent protein (N-GFP) located N-terminally to the C-IFP, and a C-fragment of a green fluorescent protein (C-GFP) located C-terminally to the N-IFP, such that the N-GFP and C-GFP are constitutively active. In various embodiments, the enzyme is CRE recombinase, and the fusion polypeptide comprises the CRE recombinase functionally linked to a plasma membrane attachment peptide separated by the GzB cleavage site. In various embodiments, the affinity tag is a Flag epitope, located C-terminal to the GzB cleavage site such that the epitope is only recognized by an M1 Flag antibody upon cleavage of the GzB site, and optionally further comprising GFP located C-terminal to the flag epitope. In various embodiments, the molecular reporter comprises an endoplasmic reticulum (ER) retention signal and an antibody-binding plasma membrane protein, wherein cleavage of the GzB site removes the ER retention signal, optionally wherein the antigen is CD40, CD4, CD19, CD20, or a tagged proteins, optionally wherein the tag is a Myc tag, Flag tag, HA tag, or Histidine tag.

In another aspect, is a nucleic acid that encodes a molecular reporter described herein are provided.

Described herein, in another aspect, is a system for detection of granzyme B activity in an antigen presenting cell, comprising a) a fusion polypeptide comprising a CRE recombinase functionally linked to a plasma membrane attachment peptide, wherein the CRE recombinase and membrane attachment peptide are separated by a GzB cleavage site; b) a reporter of CRE activity comprising a nucleic acid sequence encoding GFP and RFP in head-to-head orientation flanked by LoxP sites; and/or c) a nucleic acid sequence encoding a candidate antigen in expressible form, located proximally to a CRE activated primer recognition sequence comprising an inactive primer flanked by LoxP sites, wherein CRE induced rearrangement of the LoxP sites produces a functional primer recognition sequence.

Similarly, described herein, in another aspect, is a system for detection of recognized antigen presentation by an antigen presenting cell to a cytotoxic lymphocyte or NK cell, comprising a) an antigen presenting cell (APC) comprising: i) an exogenous nucleic acid encoding a candidate antigen, wherein the candidate antigen is expressed and presented with MHC class I and/or MHC class II molecules to a cytotoxic lymphocyte and/or NK cell; ii) a molecular reporter of Granzyme B (GzB) activity described herein or a system for detecting granzyme B activity described herein; and iii) an inhibitor of CAD-mediated degradation; and b) a cytotoxic lymphocyte and/or NK cell.

As described above, numerous embodiments are further provided that can be applied to any aspect of the present invention and/or combined with any other embodiment described herein. For example, in various embodiments, the inhibitor of CAD-mediated degradation is an exogenous inhibitor of CAD-mediated DNA degradation, a CAD knockout, or a caspase knockout (e.g., caspase 3 knockout), optionally wherein the caspase knockout is a caspase 3 knockout or wherein the exogenous inhibitor of CAD-mediated DNA degradation is a nucleic acid encoding inhibitor of caspase-activated deoxyribonuclease (ICAD) gene in expressible form; an inhibitory nucleic acid targeting CAD or caspase 3; a small molecule inhibitor of caspase 3; or a peptide or protein inhibitor of caspase 3. In various embodiments, the antigen presenting cells are selected from the group consisting of a K 562 cell, a HEK 293 cell, a HEK 293 T cell, a U2OS cell, MelJuso cell, a MDA-MB231 cell, a MCF7 cell, a NTERA2a cell, a dendritic cell, and a primary autologous B cell. In various embodiments, the cytotoxic lymphocyte are selected from the group consisting of cytotoxic CD4 T cells and cytotoxic CD8 T cells. In various embodiments, the cytotoxic lymphocytes and/or NK cells are modified to express an antigen receptor of interest.

In various embodiments, the cytotoxic lymphocytes and/or NK cells are cytotoxic T cells and/or NK cells that have been modified to express a T cell receptor from a non-cytotoxic CD4 T cell.

Described herein, in another aspect, is a method for identifying an antigen that is recognized by a cytotoxic T cell and/or NK cell, comprising a) contacting an antigen presenting cell (APC) or a library of APC, as described herein, with one or more cytotoxic T cells (CTLs) and/or NK cells under conditions appropriate for antigen recognition; b) identifying APC(s) that express recognized antigen by assaying for granzyme B activity in the APC(s), wherein increased granzyme B activity, as compared to an appropriate control, indicates the APC expresses antigen that was recognized by the cytotoxic T cell and/or NK cell; and c) isolating nucleic acid that encodes the recognized antigen from the APC identified in step b).

Similarly, described herein, in another aspect, is a method for identifying an antigen that is recognized by a cytotoxic T cell and/or NK cell, comprising a) contacting an antigen presenting cell (APC) or a library of APCs, as described herein, with one or more CTLs under conditions appropriate for antigen recognition, wherein cleavage of the GzB site removes the ER retention signal and releases the plasma membrane protein from the ER for trafficking to the plasma membrane; b) isolating APC(s) that express recognized antigen by contacting the APCs with an antibody that binds the plasma membrane protein, and purifying the antibody-bound APCs; and c) isolating nucleic acid that encodes the recognized antigen from the APCs isolated in step b).

As described above, numerous embodiments are further provided that can be applied to any aspect of the present invention and/or combined with any other embodiment described herein. For example, in various embodiments, the method further comprises sequencing the isolated nucleic acid. In various embodiments, the cytotoxic T cells and/or NK cells are obtained from a biological sample of a subject. In various embodiments, the biological sample is selected from the group consisting of blood, tumor, healthy tissue, ascites fluid, location of autoimmunity, tumor infiltrate, virus infection site, lesion, mouth mucosa, and skin. In various embodiments, the biological sample is obtained from a site of infection or autoimmune reactivity in the subject. In various embodiments, the cytotoxic T cells are CD4 or CD8 cells. In various embodiments, the cytotoxic T cells and/or NK cells are modified to express an antigen receptor of interest. In various embodiments, the cytotoxic T cells and/or NK cells have been modified to express a T cell receptor from a non-cytotoxic CD4 T cell. In various embodiments, the identifying step b) is through detection of a fluorescence signal in the APC that is increased by at least 2-fold, at least 5-fold, at least 10-fold, at least 25-fold, at least 50-fold, at least 100-fold, at least 1000-fold or more, relative to that of the control. In various embodiments, the step of identifying is performed using flow cytometry or affinity purification. In various embodiments, the step of identifying is performed using fluorescence-activated cell sorting (FACS) or affinity purification. In various embodiments, the step of isolation is performed by PCR amplification. In various embodiments, sequencing is performed by pyrosequencing or next-generation sequencing. In various embodiments, the library of APCs comprises at least 5,000 different candidate antigens.

Definitions

The articles "a" and "an" are used herein to refer to one or to more than one (i.e., to at least one) of the grammatical object of the article. By way of example, "an element" means one element or more than one element.

By "isolated" is meant a material that is free to varying degrees from components which normally accompany it as found in its native state. "Isolate" denotes a degree of separation from original source or surroundings. For example, an isolated cell can be removed from an animal and placed in a culture dish or another animal. Isolated is not necessarily being removed from all other cells.

The term "isolated population" with respect to an isolated population of cells as used herein refers to a population of cells that has been taken from its natural environment (e.g., in the body) and has been removed and separated from a mixed or heterogeneous population of cells (e.g., either in the process of removal from the natural environment, or subsequence to its removal, or a combination of both). In some embodiments, an isolated population is a substantially pure population of cells as compared to the heterogeneous population from which the cells were isolated or enriched from. In some embodiments, the isolated population is an isolated population of cells which is a substantially pure population of cells as compared to a heterogeneous population of cells comprising desired cells (e.g., cytotoxic lymphocytes) and contaminating cells. Such cells can be originally isolated from an adult or from an immature subject (e.g., ≤18 years of age, or ≤1 year of age, or ≤1 month of age, or ≤1 day from birth, or from an embryo or developing fetus).

The term "substantially pure", with respect to a particular cell population, refers to a population of cells that is at least about 50%, 60%, 70%, or 75%, preferably at least about 85%, more preferably at least about 90%, and most preferably at least about 95% pure, with respect to the cells making up a total cell population. Recast, the terms "substantially pure" or "essentially purified", with regard to a population of cells, refers to a population of cells that contain fewer than about 20%, more preferably fewer than about 15%, 10%, 8%, 7%, most preferably fewer than about 5%, 4%, 3%, 2%, 1%, or less than 1%, of contaminating cells.

An antigen presenting cell (APC) is any cell that can present antigen via MHC Class I and/or MHC Class II to an immune cell (e.g., a cytotoxic immune cell). APC are also referred to herein as APC targets, target cells, or target APC. APC used as described herein are modified to present a candidate antigen via expression of an exogenous nucleic acid stably inserted into the genome of the APC. In some embodiments, the APC are cells suitable for preparing libraries encoding candidate antigens as described herein (e.g., HEK293, HEK293T, U20S, K562, MelJuso, MDA-MB231, MCF7, NTERA2a, dendritic, and primary (autologous) B cells).

Cells and subjects, as the term is used herein, are typically human. However, subjects and cells derived therefrom, that are non-human animals are also envisioned for use. The term "non-human animals" includes all vertebrates, including, without limitation, mammals (e.g., sheep, dog, cow, horses, chickens, rodent (mice, rat, rabbit, guinea pig), primate, canine, equine, bovine, feline, porcine) and non-mammals amphibians, reptiles, etc. Cells described herein can be in the context of or otherwise isolated from any such subject described herein. Non-human primates are also possible sources. The skilled practitioner will recognized that APC and cytotoxic lymphocytes should be derived from the same species of subject.

As used herein, the term "antigen" refers to a molecule capable of inducing an immune response in the host organism, and is specifically recognized by T cells. In some embodiments, the antigens are peptides.

As used herein, the term "candidate antigen" refers to a peptide encoded by an exogenous nucleic acid introduced into the APC target intended for use in the screening methods described herein. Libraries, as described herein, comprise target cells which include the introduced candidate antigens.

"Exogenous", as the term is used herein, refers to material originating external to or extrinsic to a cell (e.g., nucleic acid from outside a cell inserted into the cellular genome is considered exogenous nucleic acid).

The terms "nucleic acid", "nucleic acid sequence", "nucleic acid molecule" and "polynucleotide" may be used interchangeably herein and refer to a polymeric form of nucleotides of any length, either deoxyribonucleotides or ribonucleotides, or analogs thereof, and may include naturally occurring nucleotides and/or modified nucleotides. Polynucleotides may have any three-dimensional structure, and may perform any function, known or unknown. Non-limiting examples of polynucleotides include a gene, a gene fragment, exons, introns, DNA, RNA, cDNA (complementary DNA), mRNA (messenger RNA), rRNA (ribosomal RNA), shRNA (small hairpin RNA), snRNA (small nuclear RNA), snoRNA (short nucleolar RNA), miRNA (microRNA), genomic DNA, synthetic DNA, synthetic RNA, and/or tRNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

"Vector", "cloning vector" and "expression vector" as used herein refer to the vehicle by which a polynucleotide sequence (e.g. a foreign gene) can be introduced into a host cell, so as to transform the host and promote expression (e.g. transcription and translation) of the introduced sequence. Each refers to a nucleic acid molecule capable of transporting another nucleic acid to which it has been linked. Preferred vectors are those capable of autonomous replication and/or expression of nucleic acids to which they are linked. Vectors capable of directing the expression of genes to which they are operatively linked are referred to herein as "expression vectors". Vectors include plasmids, phages, viruses, etc.

The terms "peptide", "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

As used herein, the term "library" refers to a collection of genetic material, as used herein, a collection of nucleic acids encoding candidate antigen. The term "library" can also refer to a collection of cells (APC) in which the individual cells collectively contain and possibly express, the library of nucleic acids. In some embodiments, a library of target APC comprise a plurality of peptides derived from any of, for example, pathogens, pathogen-infected cells, cancer cells, cells involved in (e.g., targeted in) autoimmune disease, and/or cells from healthy subjects, wherein the peptides are displayed on the surface of the target cell such that they are presented with MHC class I and/or MHC class II molecules.

The terms "T-cell" and "T-lymphocyte" are interchangeable and used synonymously herein. Examples include but are not limited to naïve T cells, central memory T cells, effector memory T cells, or combinations thereof.

The term "transduction" as used herein refers to the introduction of a foreign nucleic acid into a cell using a viral vector.

The term "transfection" as used herein refers to the introduction of a foreign nucleic acid into a cell using recombinant DNA technology. The term "transformation" means the introduction of a "foreign" (i.e., extrinsic, exogenous, or extracellular) gene, DNA or RNA sequence to a host cell, so that the host cell will express the introduced gene or sequence to produce a desired substance, such as a protein or enzyme coded by the introduced gene or sequence. One such way to transform the cells described herein is by transduction. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "detection molecule" refers to a molecule capable of being detected, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens) and the like. Exemplary detectable moieties suitable for use as detection molecules include affinity tags and detectable labels. Examples of detectable labels are, without limitation, fluorescers, chemiluminescers, and chromophores.

The term "fluorescer" refers to a substance or a portion thereof which is capable of exhibiting fluorescence in the detectable range.

The term "affinity tag" is used herein to denote a peptide segment that can be attached to a target that can be detected using a molecule that binds the affinity tag and provides a detectable signal (e.g., a fluorescent compound or protein). In principal, any peptide or protein for which an antibody or other specific binding agent is available can be used as an affinity tag.

The term "reaction mixture" as used herein refers to a fluid medium in which the library of target cells comprising the candidate antigen is in contact with the biological sample comprising the cytotoxic lymphocytes. This includes, for example, a reaction mixture in which a library of target cells comprising the candidate antigen is initially contacted with the biological sample comprising cytotoxic lymphocytes and any subsequent wash steps designed to remove nonspecific or low-affinity binding between the candidate antigens on the target cells and cytotoxic lymphocytes in the sample. Where desired, the stringency conditions of the reaction mixture can be modified so as to influence the formation of complexes between the candidate antigen and cytotoxic lymphocytes in the sample.

As used herein, the terms "specific binding," "specifically bind," and the like, refer to the ability of a first binding molecule or moiety to preferentially bind (covalently or non-covalently) to a second binding molecule or moiety relative to other molecules or moieties in a reaction mixture.

As used herein, the terms "determining," "measuring," "assessing," and "assaying" are used interchangeably and include both quantitative and qualitative determinations unless the context clearly indicates otherwise.

As used herein, the term "sample" or a "biological sample" refers to a biological material which is isolated from its natural environment and contains immune cells (such as, for example, including cytotoxic lymphocytes). A sample or a biological sample may comprise a tissue sample or a biological fluid sample. A biological fluid includes, but is not limited to, blood, plasma, sputum, urine, cerebrospinal fluid, lavages, and leukophoresis samples, for example.

As used herein, the term "pathogen" refers to an organism, including a microorganism, which causes disease in another organism (e.g., animals and plants) by directly infecting the other organism, or by producing agents that causes disease in another organism (e.g., bacteria that produce pathogenic toxins and the like). As used herein, pathogens include, but are not limited to bacteria, protozoa, fungi, nematodes, viroids and viruses, or any combination thereof, wherein each pathogen is capable, either by itself or in concert with another pathogen, of eliciting disease in vertebrates including but not limited to mammals, and including but not limited to humans. As used herein, the term "pathogen" also encompasses microorganisms which may not ordinarily be pathogenic in a non-immunocompromised host.

The term "immune cell" as used herein refers to the cells of the mammalian immune system including but not limited to antigen presenting cells, B-cells, basophils, cytotoxic T-cells, dendritic cells, eosinophils, granulocytes, helper T-cells, leukocytes, lymphocytes (e.g., cytotoxic lymphocytes), macrophages, mast cells, memory cells, monocytes, natural killer cells, neutrophils, phagocytes, plasma cells and T-cells.

The term "immune response" as used herein refers to immunities including but not limited to innate immunity, humoral immunity, cellular immunity, immunity, inflammatory response, acquired (adaptive) immunity, autoimmunity, and/or overactive immunity.

The term "mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

The term "tumor" as used herein refers to all neoplastic cell growth and proliferation, whether malignant or benign, and all pre-cancerous and cancerous cells and tissues.

The terms "cancer" and "cancerous" as used herein refer to or describe the physiological condition in mammals that is typically characterized by unregulated cell growth. Examples of cancer include, but are not limited to B-cell lymphomas (Hodgkin lymphomas and/or non-Hodgkin lymphomas), brain tumor, breast cancer, colon cancer, lung cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, and prostate cancer, including but not limited to androgen-dependent prostate cancer and androgen-independent prostate cancer.

An "appropriate control" as the term is used herein refers to a control reaction which is treated otherwise identically to an experimental reaction, with the exception of one or more critical factors. A control can be a cell which is identical, but is not exposed to an activating molecule (e.g., an activating cytotoxic lymphocyte). Alternatively, a control can be a cell which is exposed to an activating molecule but which lacks a reporter molecule (and can be otherwise identical to experimental cells). An appropriate control is determined by the skilled practitioner.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 2A shows that CTLs recognize and kill target cells pulsed with IV9 but not control peptide, as determined by 7-AAD staining. FIG. 2B shows that expression of 56 amino acid peptide (also referred to as a 56-mer) containing IV9 peptide from three different promoters leads to efficient antigen presentation and killing by IV9 CTLs, as measured by LDH release.

FIG. 4A shows a schematic of the reconstruction experiment. FIG. 4B shows fold enrichment of target cells displaying cognate antigen when spiked in at various proportions into target cells displaying control antigen.

FIG. 5A shows a schematic of the screen. FIG. 5B shows fold enrichment detected by qPCR of control (non-target) and cognate (target) peptides following screen relative to input library. Rep1 and Rep2 are two independent biological replicates.

FIG. 6A shows an antigen presenting cell (APC) expressing a DNA-encoded peptide presents epitopes derived from the peptide on MHC I molecules at its cell surface. When a T cell recognizes this complex through its T cell receptor (TCR), it forms an immunological synapse where it secretes perforin and granzymes. The granzymes enter the APC and cleave a previously membrane-bound Cre recombinase. The Cre recombinase reverses the orientation of a 3' primer site, allowing productive PCR amplification of the DNA encoding the peptide. FIG. 6B shows the results of detection of Cre-mediated inversion (Cre activity) in target cells expressing membrane-tethered Cre and exposed to GzB delivered by NK cells. The Cre activity was detected by qPCR using primers specific for the inverted reporter cassette. The genomic DNA from NK-cell treated and control untreated cells was purified and the frequency of inversion was quantified by qPCR, normalized to the abundance of the reporter in each sample (quantified using inversion-independent qPCR primers). Target cells expressing only the reporter for Cre activity (No Cre control) did not demonstrate detectable Cre activity upon GzB delivery.

FIG. 7A shows a schematic of the antibody-based reporter approach. Generally, a reporter substrate contains the Flag epitope preceded by a GzB cleavage site. Following GzB cleavage, the Flag epitope is accessible for recognition by the M1 antibody that recognized the Flag epitope specifically at the N terminus of a protein. FIG. 7B shows the results of Western blotting analyses using the M1 Flag antibody on cell lysates from target cells expressing the GzB reporter with and without delivery of GzB by NK cells. A dramatic increase in antibody target is observed in the presence of the reporter and following GzB delivery.

FIG. 10 shows the percentage of target cells that activated the GzB reporter in experiments that used the GzB reporter with a CD4 TCR. Primary CD8+ T cells were modified by lentivirus to express either the Ob1A.12 TCR or a control TCR. The modified T cells were then mixed with target cells displaying the target antigen of the Ob1A.12 TCR or mutant control antigens. Expressing the Ob1A.12 TCR conferred specific recognition of the cognate MBP peptide in the context of MHC II that could be detected using the GzB reporter.

FIG. 11 is a linear schematic of the Gzb reporter that utilizes IFP. The reporter contains part of the two halves of IFP split by a linker containing the GzB cleavage sequence. The whole IFP cassette is itself flanked by a split-GFP.

FIG. 12 is a schematic of the mechanisms of reporter activation. Prior to activation, the reporter includes two halves of IFP that are kept from maturing by a linker sequence. Upon GzB cleavage, the linker is released and the halves of IFP can come together and form active, fluorescent IFP. The split-GFP at the N- and C-termini of the construct provides constitutive GFP fluorescence and helps to stabilize the entire protein.

FIG. 13 shows the nucleotide (SEQ ID NO:2) and amino acid (SEQ ID NO:33) sequence of an exemplary GzB IFP reporter

FIG. 20 shows the results of tiling mutagenesis characterization of TCR binding. T cells expanded against the NLV epitope (NLVPMVATV (SEQ ID NO:4)) were screened against a comprehensive mutagenesis library of the NLV epitope and its adjacent two amino acids on each side. Each box in the heatmap represents one mutant, with the shading and value indicating how well this mutant performed compared to the wild-type version of the epitope.

DETAILED DESCRIPTION

Figure 1:
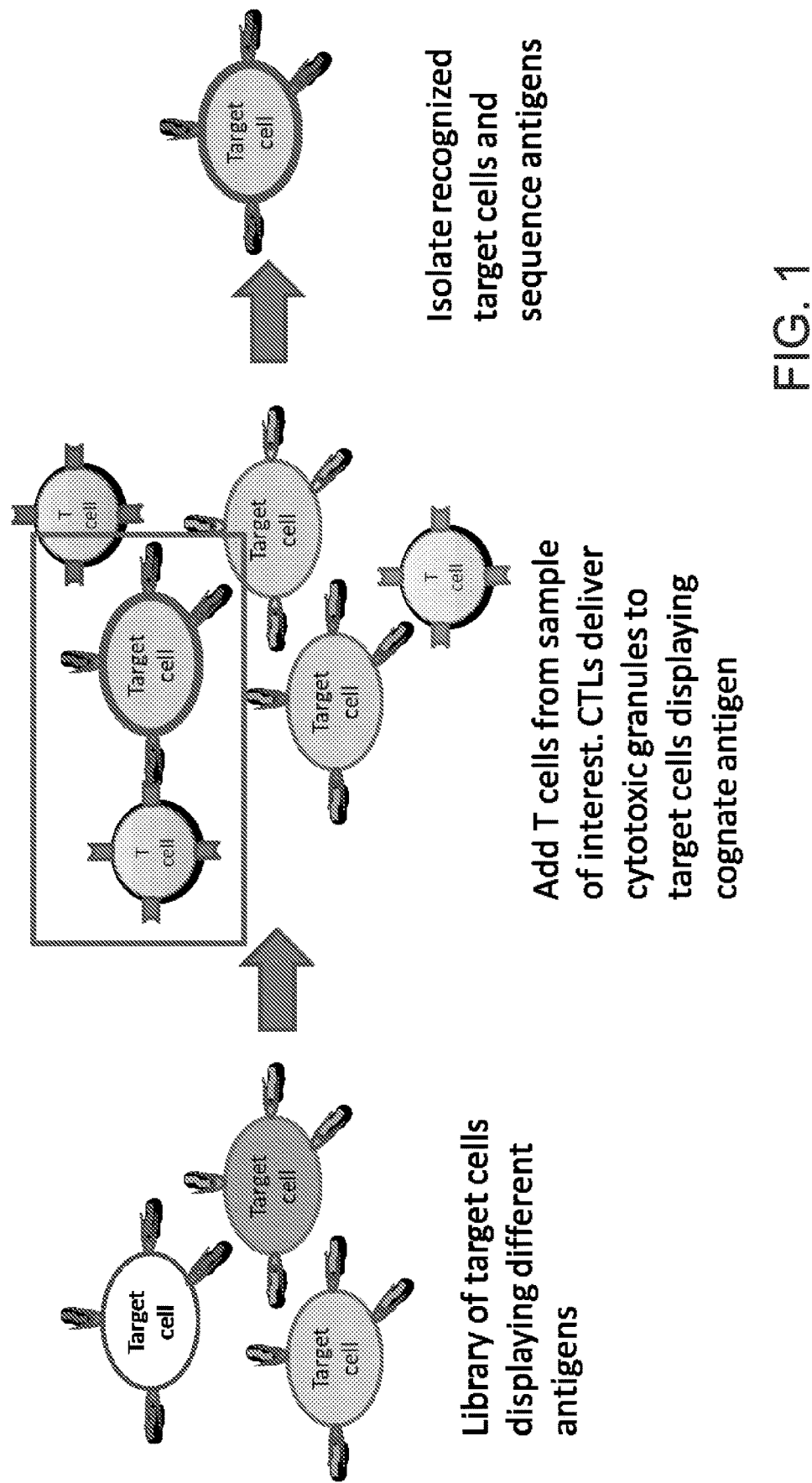
FIG. 1 depicts an overview of an exemplary approach for systematic identification of T cell antigens.

An immune response is a complex process that involves several "molecular players." However, one of the fundamental parts of the immune response is recognition of epitopes/antigens by CTLs. Epitopes are proteins or fragments of proteins presented on the cell membrane by the major histocompatibility complex (MHC). Large proteins can be broken down by specialized enzymes into hundreds of short peptide fragments, but only few of these fragments will elicit an immune response.

Productive interactions between a T cell (e.g., cytotoxic T cell) and an antigen, such as an antigen presented by an APC, are exceedingly rare and often occur among fewer than one out of one million target cells. An antigen recognized by a given T cell is typically present at exceedingly low frequencies, such as at a frequency of 1 in 100,000 antigens or less. In addition, not every target cell displaying a given antigen will encounter its cognate T cell, especially given the specificities of mixed T cell populations. Accordingly, efforts to identify T cell receptor interactions with antigens and epitopes thereof have focused on individual or small numbers of pairs of interactions based on direct measurement of T cell responses due to the inability to detect such rare events among complex mixtures of T cell receptors and epitopes/antigens (e.g., physiologically relevant and/or genome scale analyses). Moreover, existing approaches focus on non-cell-based platforms, resulting in an inability to allow for the endogenous processing and loading of peptides onto MHC by antigen presenting cells. Thus, target antigens identified by such non-cell-based platforms are less likely to actually be functionally displayed in vivo.

In order to solve this problem, compositions and methods are provided herein using a combination of elements that allow for high-throughput discovery of antigens specific to T cells, such as cytotoxic T cells, to detect such rare interactions in a manner that identifies the interaction signals above background noise in a reproducible manner and in a manner that allows recovery of the presenting APC and antigen driving the interaction. Such compositions and methods are particularly useful because they overcome the problem of low throughput and biased T cell receptor-epitope/antigen discovery by allowing for sensitive and robust detection of T cell receptor-epitope/antigen interactions using complex antigen libraries at a high-throughput (e.g., genome-wide) scale and in a modular fashion.

In general, the compositions and methods provided herein are useful to identify antigens recognized by cytotoxic lymphocytes by isolating the DNA from target APC presenting the candidate antigen using a marker/readout of recognized APC, thereby allowing for the identification of antigens that can activate the immune response from a wide variety of possible antigen fragments (e.g., a library of test antigens). Genetic material is delivered into the APC (e.g., via viral vectors) to encode one or more candidate antigens for expression and presentation on MHC class I and/or MHC class II molecules. A library of genetic material delivered into a plurality of APC results in a library of target APC. The library can be screened to identify antigens that are productively recognized by cytotoxic lymphocytes by the methods described herein. The APC or library of APC thereby comprise an exogenous nucleic acid encoding one or more candidate antigens expressed and presented with MHC Class I or MHC Class II molecules. The exogenous nucleic acid can be stably introduced into the genome of the APC (e.g., via a vector, such as a viral vector, or a transposon). In some embodiments, the inserted exogenous nucleic acid has a predetermined primer recognition sequences both upstream and downstream (referred to herein as flanking primer recognition sequences). These sequences facilitate later identification of the recognized antigen from the APC.

The APC may further be modified to contain a molecular reporter that indicates antigen recognition by the cytotoxic lymphocyte. Productive antigen recognition is identified, for example, by detection of an activity that results from antigen recognition rather than measuring responding T cells directly. For example, surrogate measures of cytotoxic T cell activity, such as IFN-γ secretion measured by ELISPOT, are typically used in the field to investigate T cell interactions. However, these surrogate measures have uncertain relevance to the in vivo function of CTLs (Sekaly, JEM 205 (1): 7 (2008)) and do not directly identify TCR-epitopes/antigen binding. By contrast, modified APC described herein allow for identification of cytotoxic lymphocyte binding via detection of a reporter of productive antigen recognition caused by cytotoxic lymphocyte-mediated modification of the APC, such as release of cytotoxic granules containing proteases like granzyme B (GzB). This occurs upon contact of the APC with cytotoxic lymphocytes expressing a T cell receptor capable of binding antigen presented by the APC and when contacted under conditions appropriate for antigen recognition. This also identifies functionally relevant T cell activity because the detected T cell modification of the APC involves induction of cytolysis. For example, productive antigen recognition by a cytotoxic lymphocyte results in activity of GzB, a serine protease involved in cytolysis, in the APC, which is demonstrated herein to minimize background noise to allow for true positive signal identification since even a 1% spurious signal level would be sufficient to mask true positives. In some embodiments, the GzB reporter is a fluorogenic reporter of GzB. In some embodiments, the GzB reporter does not produce an optically detectable signal, but provides a cell-surface signal that allows isolation of APCs that express an antigen recognized by a CTL, e.g., by affinity purification. In some embodiments, the detectable signal generated by the GzB reporter is used to enrich APC whose expressed antigen(s) are productively recognized by cytotoxic lymphocytes.

The marker of productive antigen recognition allows for an increased complexity of candidate antigens (i.e., the number of candidate antigens that can be included in the library where the single correct target of a T cell can successfully be identified) due to enhanced signal-to-noise. For example, unlike traditional methods of T cell receptor-antigen interaction analyses, the complexity of candidate antigens that can be assayed per 1 million target cells can be more than 5 k (i.e., 5,000), 10 k, 15 k, 20 k, 25 k, 30 k, 35 k, 40 k, 45 k, 50 k, 55 k, 60 k, 65 k, 70 k, 75 k, 80 k, 85 k, 90 k, 95 k, 100 k, 105 k, 110 k, 115 k, 120 k, 125 k, 130 k, 135 k, 140 k, 145 k, 150 k, 155 k, 160 k, 165 k, 170 k, 175 k, 180 k, 185 k, 190 k, 195 k, 200 k, 210 k, 220 k, 230 k, 240 k, 250 k, 260 k, 270 k, 280 k, 290 k, 300 k, 310 k, 320 k, 330 k, 340 k, 350 k, 360 k, 370 k, 380 k, 390 k, 400 k, 410 k, 420 k, 430 k, 440 k, 450 k, 460 k, 470 k, 480 k, 490 k, 500 k, 600 k, 700 k, 800 k, 900 k, 1000 k, 1100 k, 1200 k, 1300 k, 1400 k, 1500 k, 1600 k, 1700 k, 1800 k, 1900 k, 2000 k, or more, or any range in between, inclusive (e.g., 100K to 2000K) target cells. In some antigen library formats, such as libraries of random peptides where each cell displays a unique peptide, antigens that can be screened are on the order of $1\times10^8$ (i.e., hundreds of millions) to $1\times10^9$ or more.

In addition to enhanced complexity of antigens that can be screened according to the compositions and methods described herein, the methods and compositions can also include APC that preferably also include an inhibitor of DNA degradation (e.g., caspase-activated deoxyribonuclease (CAD)-mediated DNA degradation) in order to increase the efficiency of antigen recovery. Antigen(s) recognized by CTL of interest can only be identified if they can be recovered from the modified APC marked by productive antigen recognition (e.g., obtaining the sequence of the exogenous nucleic acid encoding the cognate antigen bound by the T cell receptor). However, cytolysis induced by the CTL initiates degradation of DNA that hinders efficient recovery of antigen identities. Without inclusion of an inhibitor of DNA degradation, approximately one single antigen from 100 modified APC marked by productive antigen recognition (i.e., antigens that 1 out of 100 modified APC had been presenting or 1% efficiency) can be identified. As described further below, the inclusion of an inhibitor of DNA degradation, such as an inhibitor of CAD-mediated DNA degradation, increases the antigen recovery at least 5-fold (i.e., 5% efficiency) and can be at least 5%, 10%, 15%, 20%, 25%, 30%, 35%, 40%, 45%, 50%, or more, or any range in between, inclusive (e.g., 5%-50%) of antigen recovery. Thus, the present methods can be used to attain greater than 5%, e.g., 50% or higher recovery (with 100% being the theoretical limit).

Due to the large number of antigens that can be screened and efficiency of antigen recovery in an individual experiment, the methods described herein require fewer T cells and can therefore be applied to samples with limited numbers of T cells directly ex vivo.

Also provided herein are a plurality of APCs modified as described herein, wherein the APCs comprise different exogenous nucleic acids encoding candidate antigens, such that the APCs collectively present a library of candidate antigens. In some embodiments, each APC contains and expresses a single nucleic acid, perhaps in multiple copies, to thereby present a single candidate antigen with MHC Class I and/or MHC Class II molecule. In other embodiments, each APC contains and expresses a handful of different nucleic acids expressing different candidate antigens, perhaps in multiple copies, to thereby present several candidate antigens (e.g., 2, 3, 4, 5, 6, or more) with MHC Class I and/or MHC Class II molecules.

Preferably the APCs for the library are derived from the same cell type, (e.g., such that they were clonal prior to modification). In various embodiments described herein, the library is made of a plurality of APCs that are an isolated population and/or are substantially pure population of cells. Examples of suitable cells include, without limitation, a K 562 cell, a HEK 293 cell, a HEK 293 T cell, a U2OS cell, MelJuso cell, a MDA-MB231 cell, a MCF7 cell, a NTERA2a cell, a dendritic cell, and a primary autologous B cell.

In methods described herein, generally, the APC, or plurality thereof, is contacted by the cytotoxic lymphocyte, under conditions appropriate for antigen recognition. In some embodiments, a reaction sample comprising the APC targets are mixed with a biological sample comprising cytotoxic lymphocytes of interest and incubated to allow the recognition by the cytotoxic lymphocytes of any target cells displaying the cognate antigen(s). Upon recognition, the cytotoxic lymphocytes modify the target cell in a detectable manner (e.g., release their cytotoxic granules, which contain the serine protease Granzyme B (GzB), in order to initiate the killing process). Cells that are so modified are identified and the exogenous nucleic acid encoding the cognate antigen is isolated therefrom. Sequencing of the isolated exogenous nucleic acid identifies the recognized antigen. This method, used with a plurality of APC expressing a library of candidate antigen, can be used to comprehensively identify a target antigen specific to a given cytotoxic lymphocyte. Additional details and representative embodiments are further described below.

Uses of the Compositions and Methods

CTLs have long been understood to recognize cells that are infected by intracellular pathogens, and they are necessary for the control of many infectious diseases, including HIV. Aberrant CTL recognition of self-antigens, on the other hand, can cause autoimmune diseases including Type 1 Diabetes. Recent advances in tumor immunology have highlighted another important function of CTLs: their ability to recognize and clear tumors. This function serves as the foundation for promising immunotherapies such as adoptive T cell transfer and immune checkpoint blockade, which have resulted in the durable cure of a subset of patients with previously intractable cancers. A major ongoing challenge is the characterization of the antigens driving T cell activity in each of these contexts.

Understanding protective and pathogenic T cell responses is critical to inform the discovery of biomarkers or co-interventions that can improve immunotherapies to help a wider range of patients. The technology disclosed herein can be used to identify the target antigens of T cells of interest as well as for unbiased profiling to characterize protective or pathogenic T cell responses.

Identifying the Target Antigens of TCRs of Interest

This technology can be directly applied to identify the targets of isolated T cell clones, as demonstrated herein. In addition, it can be used to identify the targets of TCRs of interest that are identified by DNA sequencing. The approach can be applied to TCRs coming from either CD4 or CD8 T cells. These TCR sequences can be synthesized and introduced into primary T cells that are subsequently screened in our platform. Notably, technologies for sequencing TCRs are improving dramatically and promise to uncover many other applications for this platform.

Autoimmune Disease

Advances in high throughput sequencing have enabled the identification of potentially pathogenic T cell clones or TCRs that are expanded within patients or conserved across patients with diseases such as type 1 diabetes, multiple sclerosis, ankylosing spondylitis, aplastic anemia, large granular lymphocytic leukemia, polymyositis, thyroiditis, and cardiomyopathy. Existing methods to identify the antigens recognized by these T cells lack the throughput to enable unbiased antigen discovery, even in cases where the TCR sequence is known. These T cells and/or TCRs can be used in the methods described herein to identify their target antigens. This will generate insights into disease pathogenesis, provide biomarkers, and open the door for targeted therapies to specifically suppress the pathogenic autoimmune reaction.

Cancer Immunotherapy

A major outstanding challenge in the field of cancer immunotherapy is to identify tumor antigens that can mediate productive anti-tumor immunity. T cell clones from tumor infiltrates have been isolated and TCR sequencing of tumor infiltrates has demonstrated oligoclonal expansions of tumor-specific T cells. Patient-specific neoantigen libraries can be generated containing the novel protein fragments arising from somatic mutations in patient tumors. Tumor-specific T cells can then be screened systematically for recognition of these neoepitopes and screened genome-wide for recognition of non-mutated tumor antigens. Understanding productive anti-tumor immunity can lead to the development of biomarkers and co-interventions to enhance the success of immunotherapy.

Unbiased Profiling of Protective or Pathogenic T Cell Responses

The herein described technology can be applied to identify the specificities of mixed populations of T cells. This allows the characterization of protective or pathogenic T cell responses even in cases where specific clones or TCRs of interest have not yet been identified.

The platform can be applied to populations of T cells in each of the contexts described above. For example, it can be used to screen bulk T cells isolated from Type 1 Diabetes patients to identify the complete set of pancreatic autoantigens recognized by patient T cells. Similarly, polyclonal tumor infiltrating T cells can be screened to profile the scope of mutated and unmutated tumor antigens recognized in anti-tumor immunity.

Protection from Infectious Disease

T cells are thought to mediate protection to a wide range of infectious diseases. For example, there is a strong association between the MHC Class I allele HLA-B57 and elite control of HIV, implicating CD8 T cells and specific target antigens as likely determinants of viral control. The technology disclosed herein can be used to systematically profile CTL specificity in patients with particular clinical outcomes, for example immunity to controlled malaria exposure or elite control of HIV, to identify correlates of protection and inform vaccine design.

The platform can also contribute to improved vaccine design by identifying the characteristics of effective T cell epitopes. While some algorithms exist for predicting the affinity of peptides for MHC molecules, there is no understanding of other characteristics that make particular peptides more likely to be productively recognized by T cells. The herein disclosed technology enables the discovery of large numbers of T cell epitopes that are both productively displayed by target cells and recognized by patient T cells. These epitopes can be studied to reveal the properties of effective T cell epitopes. This knowledge can then be applied to generate optimized vaccines and T cell therapies in cancer and infectious diseases (e.g. HIV, cytomegalovirus infection, and malaria).

Cytotoxic Lymphocytes and NK Cells

In some embodiments, the cytotoxic lymphocytes are cytotoxic T cells. These can be either CD4 or CD8. The cytotoxic T cells can express their endogenous receptors, or may be modified to express an exogenous antigen receptor of interest. In some embodiments, the exogenous receptor is from a T cell that does not have cytotoxic activity (e.g., non-cytotoxic CD4 T cell). The specificity of a T cell is contained in the sequence of its T cell receptor. It has been demonstrated that introducing the TCR from one T cell into another can retain the effector functions of the recipient cell while transferring the specificity of the new TCR. This is the basis of TCR therapeutics in general. Moreover, a TCR from a CD8 T cell can drive the effector functions of CD4 T cells when introduced into donor CD4 cells (Ghorashian et al., J Immunol, 194(3): 1080-1089 (2015)). As demonstrated herein, transferring the TCR from a CD4 T cell into donor CD8 cells can confer GzB-mediated cytotoxic activity towards antigens presented on MHC Class II and recognized by the CD4 TCR (see FIG. 10 herein). In some embodiments, the exogenous T cell receptor is from a T helper (Th1 or Th2) or a regulatory T cell. Other types of cytotoxic cells can be used in the assays, such as natural killer cells, to identify factors those cells recognize. The cytotoxic lymphocytes used in the method can be clonal or a mixed population. Alternatively, or in addition, to CTLs, natural killer (NK) cells that have been engineered to express a T cell receptor can be used.

The cytotoxic lymphocytes or NK cells can be obtained from a variety of sources. Typically the cytotoxic lymphocytes are obtained from a biological sample.

Samples

In some embodiments, a "reaction sample" comprises a target cell or a library of target cells comprising candidate antigens. The reaction sample can also comprise additional buffers, salts, osmotic agents, etc. to facilitate the formation of complexes between the candidate antigen on the surface of the target cell and the T cells in the sample of interest.

A "biological sample" refers to a fluid or tissue sample of interest that comprises cells of interest such as cytotoxic lymphocytes or antigen presenting cells. In exemplary embodiments, the biological sample comprises cytotoxic T cell (CTLs) and/or Natural Killer cells. A biological sample can be obtained from any organ or tissue in the individual, provided that the biological sample comprises cells of interest. The organ or tissue can be healthy or can be diseased. In some embodiments, the biological sample is from a location of autoimmunity, a site of autoimmune reaction, a tumor infiltrate, a virus infection site, or a lesion.

In some embodiments, a biological sample is treated to remove biological particulates or unwanted cells. Methods for removing cells from a blood or other biological sample are well known in the art and can include e.g., centrifugation, ultrafiltration, immune selection, or sedimentation etc. Some non-limiting examples of biological samples include a blood sample, a urine sample, a semen sample, a lymphatic fluid sample, a cerebrospinal fluid sample, a plasma sample, a serum sample, a pus sample, an amniotic fluid sample, a bodily fluid sample, a stool sample, a biopsy sample, a needle aspiration biopsy sample, a swab sample, a mouth-wash sample, mouth mucosa sample, a cancer sample, a tumor sample, tumor infiltrate, a tissue sample (e.g., skin), a cell sample, a synovial fluid sample, or a combination of such samples. For the methods described herein, it is preferred that a biological sample is blood or tissue biopsies (e.g. tumors, site of autoimmunity or other pathology).

Modification of APC

The APC are engineered, such as by transfection or genetic modification, to express exogenous nucleic acid encoding the candidate antigen. The APC may be further modified to downregulate and/or upregulate expression of compositions of interest, such as genes, proteins, chemical labels, exogenous nucleic acid encoding reporter molecules, and the like.

As described above, the APC may further be modified to contain a molecular reporter that indicates antigen recognition by the cytotoxic lymphocyte and/or NK cell. Productive antigen recognition is identified, for example by detection of an activity that results from antigen recognition rather than measuring responding T cells directly. In some embodiments, a reporter of GzB activity is used, such as one or more GazB-based reporters described further herein.

In the methods and compositions described herein, the APC may further include an inhibitor of DNA degradation. In some embodiments, the inhibitor directly blocks DNA degradation by CAD. GzB initiates caspase activation in target cells, which leads to internucleosomal degradation of genomic DNA by the caspase-activated deoxyribonuclease (CAD). This degradation of genomic DNA can be slowed or inhibited in a number of contemplated manners by providing an inhibitor of CAD-mediated DNA degradation. For example, the protein inhibitor of caspase-activated deoxyribonuclease (ICAD), which blocks the degradation of DNA during apoptosis, can be used. For example, in some embodiments, the cells can be modified to express a protein inhibitor of caspase-activated deoxyribonuclease (ICAD) to inhibit degradation of genomic DNA mediated by active GzB. In some embodiments, the APC target is manipulated to overexpress ICAD, or to express a mutant of ICAD that has increased activity.

In some embodiments, the ICAD contains a mutation conferring resistance to caspase cleavage (e.g., D117E and/or D224E), otherwise referred to herein as a caspase resistant mutant (see Sakahira et al., Arch Biochem Biophys. 2001 Apr. 1; 388(1):91-9; Enari et al., Nature. 1998 Jan. 1; 391(6662):43-50; Sakahira et al., Nature. 1998 Jan. 1; 391(6662):96-9). Exemplary sequences of the ICAD precursor (also known as DNA fragmentation factor subunit alpha or DFFA) are available in GenBank at Acc. No. NM_004401.2 (transcript variant 1) encoding NP_004392.1 (isoform 1); and NM_213566.1 (transcript variant 2) encoding NP_998731.1 (isoform 2). An exemplary mature ICAD sequence is as follows; the residues at D117 and D224 are in upper case:

(SEQ ID NO: 5)

```
  1  mevtgdagvp  esgeirtlkp  cllrrnysre  qhgvaascle  dlrskacdil  aidksltpvt 61  lvlaedgtiv  ddddyflclp  sntkfvalas  nekwaynnsd  ggtawisqes  fdvdetDsga 121  glkwknvarq  lkedlssiil  lseedlqmlv  dapcsdlaqe  lrqscatvqr  lqhtlqqvld 181  qreevrqskq  llqlylqale  kegsllskqe  eskaafgeev  davDtgisre  tssdvalash 241  iltalrekqa  pelslssqdl  elvtkedpka  lavalnwdik  ktetvqeace  relalrlqqt 301  qslhslrsis  askasppgdl  qnpkrarqdp  t
```

Alternatively or in addition, the cells can include a CAD knockout (e.g., disruption of the CAD gene using CRISPR; an exemplary reference gene sequence is at RefSeqGene NG_029098.1, Range 5001-17026) or knockdown (e.g., using an inhibitory nucleic acid such as shRNA, siRNA, LNA, or antisense). Chemical or small molecule DNAse inhibitors can also be used, e.g., Mirin, a cell-permeable inhibitor of the MRE11 nuclease, or intercalating dyes like ethidium bromide, that inhibit proteins that interact with nucleic acids.

Caspase inhibition can also be used to prevent cleavage of ICAD and resulting activation of CAD during apoptosis. Caspase 3 initiates DNA degradation by cleaving DFF45 (DNA fragmentation factor-45)/ICAD (inhibitor of caspase-activated DNase) to release the active enzyme CAD (Wolf et al., J Biol Chem. 1999 Oct. 22; 274(43):30651-6). Thus, the cells can include a caspase 3 knockout (e.g., disruption of the caspase 3 gene using CRISPR; an exemplary reference gene sequence is at RefSeqGene ID NC_000004.12, Range184627696-184649475 complement) or knockdown (e.g., using an inhibitory nucleic acid such as shRNA, siRNA, LNA, or antisense). Exemplary sequences for human caspase 3 are in GenBank at NM_004346.3 (transcript variant 1) encoding NP_004337.2 (caspase-3 isoform a preproprotein); other isoforms can also be used. Chemical or small molecule caspase inhibitors can also be used (e.g., Z-VAD-FMK (Benzyloxycarbonyl-Val-Ala-Asp(OMe)-fluoromethylketone); Z-DEVD-FMK; Ac-DEVD-CHO; Q-VD-Oph (Quinolyl-Val-Asp-OPh); M826 (Han et al., The Journal of Biological Chemistry (277):30128-30136 (2002)); N-Benzylisatin Sulfonamide Analogues as described in Chu et al., J. Med. Chem., 2005, 48 (24), pp 7637-7647; Isoquinoline-1,3,4-trione Derivatives as described in Chen et al., J. Med. Chem., 2006, 49 (5), pp 1613-1623); as well as protein or peptide inhibitors of caspases (e.g., mammalian XIAP (GenBank Refseq: NP_001158.2) or Cowpox CrmA (GenBank Refseq: NP_001158.2). Although Caspase 3 is the key caspase for this purpose and a report has been published indicating that CAD is not activated during apoptosis in the absence of Caspase 3 (Tang et al., J Biol Chem. 1998 Oct. 30; 273(44): 28549-52), and inhibitors of caspase 3 are exemplified, other reports have determined that other caspases can cleave ICAD. Thus, inhibitors of other caspases can also be used, e.g., pan-caspase inhibitors, or inhibitors of executioner caspases (Caspase 6 or 7) or initiator caspases (Caspase 2, 8, 9, or 10). In some embodiments, the caspase inhibitor will inhibit caspase 3 and other caspases as well, e.g., caspase 6, 7, 2, 8, and/or 9.

A variety of methods are available to create the desired modifications. Typically vectors are used to introduce nucleic acid into a cell.

Many such vectors useful for transferring (e.g., by transformation) exogenous genes into target mammalian cells are available for generating the APC and libraries described herein. The vectors may be episomal, e.g., plasmids, virus derived vectors such cytomegalovirus, adenovirus, etc., or may be integrated into the target cell genome, through homologous recombination or random integration, e.g., retrovirus derived vectors such MMLV, HIV-1, ALV, etc. Lentiviral vectors such as those based on HIV or FIV gag sequences can be used to transfect non-dividing cells, such as the resting phase of human stem cells (see Uchida et al. (1998) P.N.A.S. 95(20): 11939-44). In some embodiments, combinations of retroviruses and an appropriate packaging cell line may also find use, where the capsid proteins will be functional for infecting the target cells. Usually, the cells and virus will be incubated for at least about 24 hours in the culture medium. The cells are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line.

Many viral vectors or virus-associated vectors are known in the art. Such vectors can be used as carriers of a nucleic acid construct into the cell. Constructs may be integrated and packaged into non-replicating, defective viral genomes like adenovirus, adeno-associated virus (AAV), or herpes simplex virus (HSV) or others, including retroviral and lentiviral vectors, for infection or transduction into cells. The vector may or may not be incorporated into the cells genome. Viral vectors which may be used include but are not limited SIN lentiviral vectors, retroviral vectors, foamy virus vectors, adeno-associated virus (AAV) vectors, hybrid vectors and/or plasmid transposons (for example sleeping beauty transposon system) or integrase based vector systems. Other vectors that may be used in connection with alternate embodiments will be apparent to those of skill in the art.

The constructs may include viral sequences for transfection, if desired. Alternatively, the construct may be incorporated into vectors capable of episomal replication, e.g., EPV and EBV vectors.

The inserted material of the vectors described herein may be operatively linked to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence. In some examples, transcription of an inserted material is under the control of a promoter sequence (or other transcriptional regulatory sequence) which controls the expression of the recombinant gene in a cell-type in which expression is intended. It will also be understood that the inserted material can be under the control of transcriptional regulatory sequences which are the same or which are different from those sequences which control transcription of the naturally-occurring form of a protein. In some instances the promoter sequence is recognized by the synthetic machinery of the cell, or introduced synthetic machinery, required for initiating transcription of a specific gene.

The promoter sequence may be a "tissue-specific promoter," which means a nucleic acid sequence that serves as a promoter, i.e., regulates expression of a selected nucleic acid sequence operably linked to the promoter, and which affects expression of the selected nucleic acid sequence in specific cells. The term also covers so-called "leaky" promoters, which regulate expression of a selected nucleic acid primarily in one tissue, but cause expression in other tissues as well.

The cell types of the APC are not particularly limited. The basic requirement is that the APC are able to endogenously process and present antigens on MHC I (e.g., including proteasome expression, TAP transporter expression, and proper folding and trafficking of MHC molecules). It is believed that this is true for almost all human cells and other mammalian cells. The present system can also be used with single-chain MHC-peptide fusions (Yu et al., Immunol 168 (7): 3145-3149 (2002)) that bypass the need for endogenous antigen processing. However, this would require increased library sizes and may lose information on whether peptides would be endogenously represented. APC should also have the ability to efficiently introduce exogenous DNA into the cells, e.g., by lentiviral/retroviral transduction or transfection, methods for which are well-known in the art.

With respect to the IFP-based GzB reporter systems described herein, APC are those in which the IFP protein is able to mature and fluoresce. Thus, the cells express sufficient levels of biliverdin, which is a critical co-factor for IFP maturation in these cell lines. Biliverdin can also be supplemented exogenously (e.g., by increasing expression of endogenous biliverdin, or by adding biliverdin to the cells) to enable additional cells to be used. Cells suitable for IFP reporter-based expression are well-known in the art and include, without limitation, HEK 293T, MelJuso, MDA-MB231, MCF7, and NTERA2. It has been reported in the literature to also function in LN229 cells, primary neurons, and hepatocytes (Yu et al., Nature Communications 5:3626 (2014)).

Primary dendritic cells and primary B cells can be used for autologous screening. Where the IFP-based reporter system is used, supplemental biliverdin can be used as needed. Bilverdin can be supplied to cells as needed using well-known methods in the art.

In some embodiments, the APCs of the compositions and methods described herein are MHC-deficient, i.e., do not express endogenous MHC. This allows the profiling of T cell responses restricted to specifically chosen MHC alleles that are engineered to be expressed by the APC. For example, introducing a single MHC alleles ensures that any responses detected are presented on this one allele; thus the results can be interpreted without the need for any further deconvolution. Such a result is not easily obtained if the set of endogenous MHC alleles is present. This also allows the possibility of re-use of the same target cells to profile T cells from different patients or with different MHC alleles by introducing in the new MHC of interest. It has also be determined herein that doing so also reduces background killing activity due to T cells recognizing other antigens. The level of MHC expression on the target cells affects the background rate of T cell activation. Beginning with MHC-deficient target cells enables fine tuning the amount of MHC on the surface to optimize signal-to-noise. In some embodiments, K 562 cell, a HEK 293 cell, a HEK 293 T cell, a U2OS cell, MelJuso cell, a MDA-MB231 cell, a MCF7 cell, a NTERA2a cell, a dendritic cell, and a primary autologous B cell is used.

Thus, compositions and methods described herein can be applied to T cells, NK cells, and any other cells that deliver a protease upon cell recognition. The experiments detailed in the Examples section herein demonstrate the feasibility of the methods to identify CD8+ T cell antigens and factors that confer recognition by Natural Killer cells. CD4+ T cell antigens can be characterized by directly screening cytotoxic CD4 T cells or by introducing the TCRs from non-toxic CD4 T cells into cytotoxic CTL (e.g., CD8 T cells), possibly with the co-expression of CD4.

Libraries of APC Targets

General methods for the construction of large, genome-scale libraries of sequences for the expression of encoded polypeptides, such as in the generation of the candidate antigen libraries to be introduced into MHC target cells, are known to the skilled practitioner. Some examples of such methods are found in Xu G J, Kula T, Xu Q, Li M Z, Vernon S D, Ndung'u T, et al. Comprehensive serological profiling of human populations using a synthetic human virome. Science. 2015; 348(6239); Larman H B, Zhao Z, Laserson U, Li M Z, Ciccia A, Gakidis M A, et al. Autoantigen discovery with a synthetic human peptidome. Nat Biotechnol. 2011; 29(6):535-41. Epub 2011/05/24. doi: 10.1038/nbt.1856. pmid:21602805; Zhu J, Larman H B, Gao G, Somwar R, Zhang Z, Laserson U, Ciccia A, Pavlova N, Church G, Zhang W, Kesari S, Elledge S J. Protein interaction discovery using parallel analysis of translated ORFs (PLATO). Nat Biotechnol. 2013 April; 31(4):331-4. doi: 10.1038/nbt.2539, the contents of which are incorporated herein by reference in their entirety.

Also provided herein are libraries of APC target cells comprising a plurality of candidate antigens. In some embodiments, the target cells further comprise one or more reporter constructs useful in identification of an activated APC, such as those described herein. In some embodiments, the reporter is sensitive to Granzyme B activity. In some embodiments, the APC target cells further comprise an inhibitor of CAD-mediated DNA degradation. Numerous representative examples are described herein. For example, in some embodiments, the target cells further comprise an exogenous inhibitor of the caspases activated by GzB so as to inhibit degradation of genomic DNA, or a CAD or caspase knockout, such as those described herein. For example, in some embodiments, the caspase-activated DNAse (CAD) which is activated by GzB is inhibited by inhibitor of caspase-activated deoxyribonuclease (ICAD) or a mutant thereof. In some embodiments, the ICAD mutation is D117E, wherein the aspartic acid at position 117 is substituted with a glumatic acid. In some embodiments, the ICAD further comprises the mutation is D224E, wherein the aspartic acid at position 224 is substituted with a glumatic acid. In some embodiments, the isoform of ICAD has the sequence disclosed in GenBank Accession Number O00273-2. Other isoforms of ICAD will also produce acceptable results in the compositions and methods described herein. In some embodiments, the exogenous inhibitor is wild type.

In some embodiments, the candidate antigens are encoded by genomic DNA. The genomic DNA may be isolated from a subject (e.g., human) or from infectious organisms or combinations thereof. In some embodiments, the subject is healthy. In some embodiments, the subject has a disease. In some embodiments, the infectious organisms are pathogens, including but not limited to bacteria, viruses, bacteria, fungi, protozoa, and multicellular parasitic organisms. In some embodiment, the plurality of candidate antigens from which the library is generated represents a substantially complete set of antigens from the genome of a healthy subject or a subject with a disease (for example, diseases including but not limited to cancer, autoimmune disease, cardiovascular disease, infectious disease etc.) In some embodiments, the plurality of candidate antigens represents a substantially complete set of peptides from a pathogen or group of pathogens, viruses, bacteria, or fungi (e.g., all pathogenic viruses, bacteria or fungi).

In some embodiments, antigen libraries can be used, such as, without limitation, open reading frame (ORF) collections, genome-wide peptide libraries, and application-specific custom libraries. In some embodiments, genome-wide detection of candidate antigens is used. In some embodiments, the library is a human genome-wide peptide library, such as one that tiles the human proteome (e.g., one that comprises 259,345 peptides that tile across the entire human proteome in 90 amino acid fragments with 45 amino acid overlap). In some embodiments, the library is a virome-wide library, such as one that tiles the virome (e.g., one that comprises 93,904 peptides that tile across the proteomes of all viruses annotated to infect humans in 56 amino acid fragments with 28 amino acid overlap). In some embodiments, the library is a CMV genome-wide peptide library, such as one that tiles the CMV proteome (e.g., one that comprises 5764 peptides that tile across all confirmed and predicted human cytomegalovirus proteins in 56 amino acid fragments with 28 amino acid overlap).

The antigen will most often be encoded at single copy at the DNA level. It will be produced, processed, and presented on MHC, typically at tens to thousands of molecules per cell. Even single peptides on the surface of the cell can however be productively recognized by cytotoxic lymphocytes, and so the system is functional for even very low copies of surface expressed antigen.

In various embodiments, the libraries of target cells comprising candidate antigens comprise about $10^2$ to about $10^{14}$ target cells.

In some embodiments, each target cell encodes a unique candidate antigen. Alternatively, in some embodiments, a target cell can encode more than one unique candidate antigen, such as 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more, or any range in between, inclusive (e.g., 5-10) candidate antigens per cell. If the screen results in higher background when using multiple antigens per cell, the methods can include performing a second round of the screen with just one antigen per cell (preferably re-cloned antigens from the first pass).

In exemplary embodiments, the library comprises any one or more of about $1\times10^2$ to about $10^{14}$ target cells, about $1\times10^3$ to about $10^{14}$ target cells, about $1\times10^4$ to about $10^{14}$ target cells, about $1\times10^5$ to about $10^{14}$ target cells, about $1\times10^6$ to about $10^{14}$ target cells, about $1\times10^7$ to about $10^{14}$ target cells, about $1\times10^8$ to about $10^{14}$ target cells, about $1\times10^9$ to about $10^{14}$ target cells, about $1\times10^{10}$ to about $10^{14}$ target cells, about $1\times10^{11}$ to about $10^{14}$ target cells, about $1\times10^{12}$ to about $10^{14}$ target cells, about $1\times10^{13}$ to about $10^{14}$ target cells, or about $1\times10^{14}$ target cells. The target cell libraries described herein provide at least about $10^2$ to about $10^{14}$ candidate antigens, wherein a sufficient amount of target cells comprise a unique candidate antigen for effective library screening. In some embodiments, a representation of between 10 and 10,000 is used, meaning each candidate antigen is presented by 10-10,000 cells.

In various embodiments, each target cell comprises about $10^2$ to about $10^{14}$ molecules of the candidate antigen. In exemplary embodiments, each target cell comprises about $1\times10^2$ to about $10^{14}$ copies of the candidate antigen, about $1\times10^3$ to about $10^{14}$ copies of the candidate antigen, about $1\times10^4$ to about $10^{14}$ copies of the candidate antigen, about $1\times10^5$ to about $10^{14}$ copies of the candidate antigen, about $1\times10^6$ to about $10^{14}$ copies of the candidate antigen, about $1\times10^7$ to about $10^{14}$ copies of the candidate antigen, about $1\times10^8$ to about $10^{14}$ copies of the candidate antigen, about $1\times10^9$ to about $10^{14}$ copies of the candidate antigen, about $1\times10^{10}$ to about $10^{14}$ copies of the candidate antigen, about $1\times10^{11}$ to about $10^{14}$ copies of the candidate antigen, about $1\times10^{12}$ to about $10^{14}$ copies of the candidate antigen, about $1\times10^{13}$ to about $10^{14}$ copies of the candidate antigen, or about $1\times10^{14}$ copies of the candidate antigen.

In various embodiments, the candidate antigens are encoded by nucleic acids that are about 21 to about 150 nucleotides in length. In further embodiments, the candidate antigens are encoded by nucleic acids that are about 24 to about 150 nucleotides in length, about 30 to about 150 nucleotides in length, about 40 to about 150 nucleotides in length, about 50 to about 150 nucleotides in length, about 60 to about 150 nucleotides in length, about 70 to about 150 nucleotides in length, about 80 to about 150 nucleotides in length, about 90 to about 150 nucleotides in length, about 100 to about 150 nucleotides in length, about 110 to about 150 nucleotides in length, about 120 to about 150 nucleotides in length, about 130 to about 150 nucleotides in length, about 140 to about 150 nucleotides in length or about 150 nucleotides in length. In some embodiments, the ORF or nucleic acid encoding the candidate antigen is longer than 150 nt.

In some embodiments, the candidate antigens displayed on the surface of target cells are at least 8, 9, 10, or 11 amino acids long; in other embodiments the candidate antigens are at least 20, at least 30, at least 40, at least 50, at least 60, at least 70, at least 80, at least 90, at least 100, at least 150, at least 200, at least 250, at least 300, at least 350, at least 400, at least 450 amino acids or more in length. Upon expression, longer antigens (e.g., hundreds of amino acids) are processed down into short peptides of 8-11 amino acids that are displayed on the surface of the target cells.

In some embodiments, the candidate antigens are complete ORFs (e.g., hundreds of amino acids in length). The full-length candidate antigens are not necessarily completely displayed on the surface of the APC. Instead, such antigens are expressed by the cells and endogenously processed into shorter peptides that are displayed on the cell surface. Identification of an APC having a nucleic acid encoding such a long candidate antigen could then be followed by further screening of various fragments of the identified candidate.

In various embodiments, the candidate antigens bind to the lymphocyte with a $K_d$ of from about 1 fM to about 100 µM, about 1 pM to about 100 µM, about 100 nM to about 100 µM, about 1 µM to about 100 µM, about 1 µM to about 10 µM, about 1 pM to about 100 nM, about 1 pM to about 10 nM, about 1 pM to about 5 nM. In some embodiments, the candidate antigens bind to the lymphocyte with a $K_d$ of 1 mM.

Screening Libraries of Target Cells to Identify Antigens

Candidate antigens are expressed in a library of APC for presentation on MHC Class I or Class II molecules to cytotoxic lymphocytes. This library is then mixed with a sample of cytotoxic lymphocytes (e.g., CTLs) of interest, under conditions suitable for recognition of any target cells displaying their cognate antigen such as in a reaction mixture. Upon recognition, the lymphocytes initiate the killing process of the target cell (e.g., for CTLs release their cytotoxic granules, which contain the serine protease Granzyme B (GzB)). A reporter of the initiated killing process in the target cell (e.g., intracellular GzB activity) is used to isolate genomic DNA from the recognized target cells. The nucleic acid encoding the antigen that was displayed and recognized is then identified (e.g., by PCR amplification and Next Generation Sequencing).

In addition, described herein are methods for screening libraries of target cells comprising candidate antigens for identifying antigens specific to T cells (for example, CTLs). The methods include (i) preparing a library of target cells as described herein, (ii) contacting the library of target cells with a biological sample comprising cytotoxic T cells (CTLs), (iii) isolating the target cells bound to the CTL, wherein the binding of the candidate antigen on the target cell results in a desired property and (iv) isolating DNA from the isolated target cells comprising the antigen that specifically bound to the CTL and produced the desired effect. In some embodiments, the methods further comprise enriching (for example, via PCR amplification) and identifying (for example, via sequencing) the candidate antigen specific to the CTL in the sample. In some embodiments, the methods for screening as described herein are iterative. In this way, a candidate antigen specific for the target CTL may be identified.

In various embodiments, desired property includes but is not limited to any one or more of a physically detectable change, a chemically detectable change, an optically detectable change or combinations thereof. In some embodiments, the desired property may be a target-binding activity or a target-binding induced activity, e.g., a catalytic activity or a modified catalytic activity; inhibition activity, activation activity, or a modification of an inhibition activity or activation activity; structure switching activity or a modification of a structure switching activity; or cooperative activity.

Identification of the Recognized APC

In some embodiments, GzB protease activity is used as a marker of the recognized APC. GzB is a cytotoxic protease secreted by cytotoxic lymphocytes into the recognized APC. GzB triggers caspase activation and apoptosis in the APC. Previous work demonstrated that the GzB released into target cells during cytolytic killing leads to complete proteolysis of the GzB targets, indicating robust enzymatic activity to serve as the basis of a reporter. To detect GzB activity, one can use a molecular reporter of GzB activity such as those described herein. Such reporters of GzB are typically not activated by general apoptosis pathways. The of skill in the art will recognize that other markers of the recognized APC can be used, such as other proteases secreted by cytotoxic T lymphocytes (Granzymes A, K, M) or other enzymes or proteases such as TEV protease engineered into T cells to be secreted into target cells.

Reporter molecules described herein can be used to indicate increased Granzyme B activity. In some embodiments, the method includes a step of quantitating a signal from the detectable label of the reporter molecule. In some embodiments, the method includes a step of enriching a population of the target cells based on the quantitated signal. In some embodiments, the method includes a step of introducing one or more mutations into one or more candidate antigen having the desired property.

In some embodiments, the method includes iteratively repeating one or more of the contacting, isolating and identifying steps described above. The method may include, for example, a total of 1, 2, 3, 4 or more rounds of screening.

Reporters of Granzyme B Activity

Additionally, provided herein are molecular reporters of Granzyme B activity, examples of which are described herein, and also to the nucleic acids that encode the molecular reporters, and also to cells that comprise the nucleic acids and/or the molecular reporters (e.g., the APC).

Granzyme B (GzB) is a protease that is secreted by CTLs into target cells. GzB cleaves a set of substrates, including effector caspases and downstream caspase substrates, to trigger apoptosis in the target cell.

In some embodiments, the reporter comprises a fusion polypeptide comprising a GzB cleavage site (e.g., VGPD, SEQ ID NO:1) linked to a detection molecule. As the term is used herein in reference to such reporters of Gzb, "detection molecule" is a molecule liberated by cleavage of the Gzb cleavage site, having an activity such as enzymatic activity, binding activity, or light emission. Once activated by cleavage, the activity can be detected by an assay such as those described herein (e.g., detection of a detectable label, detection of an enzyme activity such as CRE, or detection of an affinity tag). GzB prefers substrates containing P4 to P1 amino acids Ile/Val, Glu/Met/Gln, Pro/Xaa, with an aspartic acid N-terminal to the proteolytic cleavage. Non-charged amino acids are preferred at P1', and Ser, Ala, or Gly are preferred at P2'. Preferably, the GzB cleavage sequence used is one that is cleaved by GzB, but not by caspases, e.g., VGPD (SEQ ID NO:1; Choi and Mitchison, PNAS, 110(16): 6488-6493 (2013). In some embodiments, other GzB cleavage sequences are used, e.g., IETD (SEQ ID NO:6) as described in Casciola-Rosen et al., Journal of Biological Chemistry, 282(7):4545-4552(2007).

Generally, the reporter provides a detectable signal, such as a fluorescent signal, only after GzB-mediated cleavage of the reporter. This allows for the isolation of cells that have been recognized by a CTL and received GzB.

Figure 13:
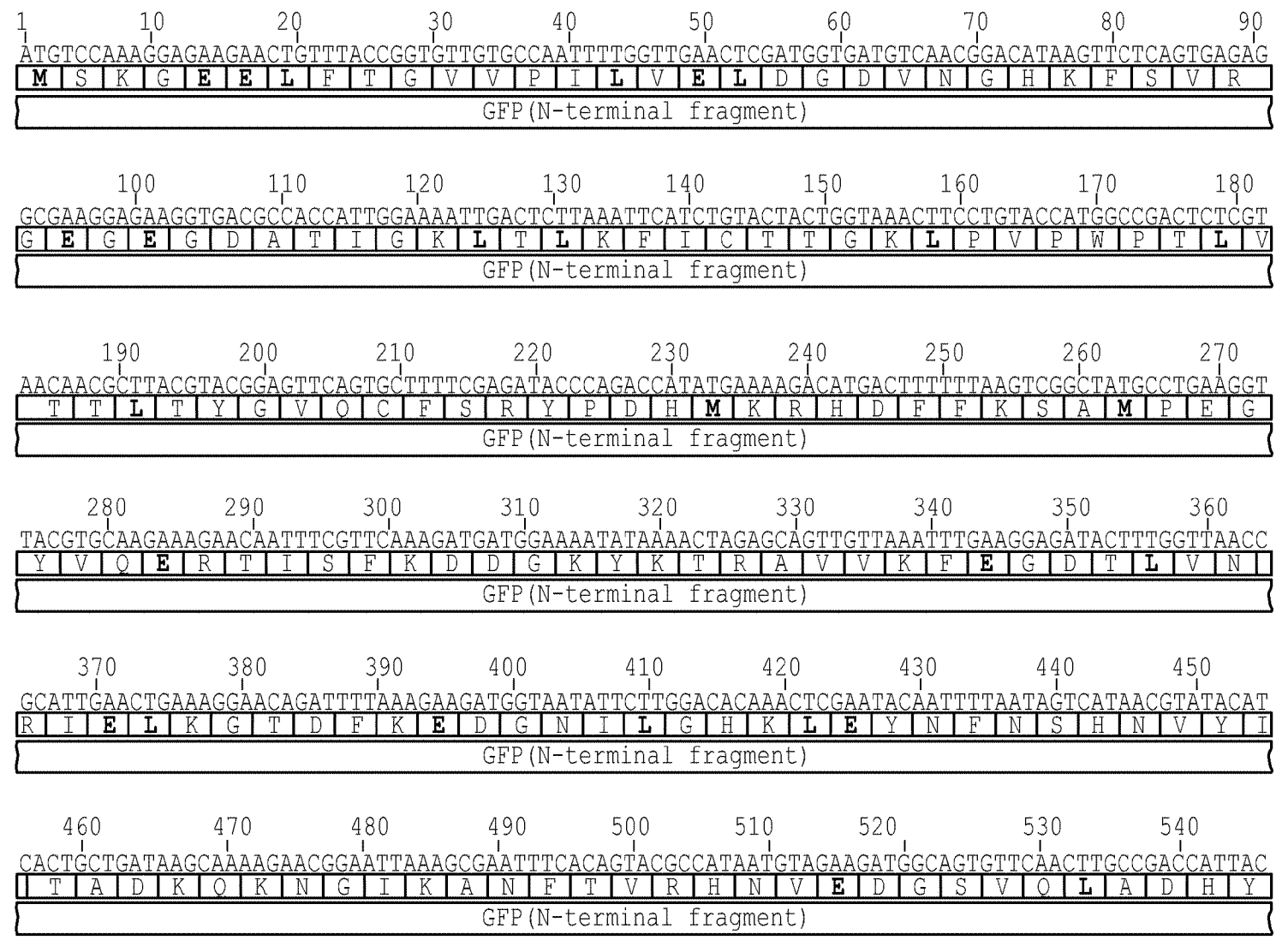

In some embodiments, the detection molecule is an Infrared Fluorescent Protein (IFP). In some embodiments, the IFP comprises a N-fragment (N-IFP) and a C-fragment (C-IFP), functionally separated by the GzB cleavage site, and is further flanked by an N-fragment of green fluorescent protein (N-GFP) located N-terminally to the C-IFP, and a C-fragment of a green fluorescent protein (C-GFP) located C-terminally to the N-IFP, such that the N-GFP and C-GFP form a constitutively active (fluorescent) molecule. One embodiment of this is illustrated in FIGS. 11-13. In particular, FIGS. 11 and 12 are diagrams that illustrate the reporter and mechanism by which it functions. FIG. 13 is the nucleic acid and encoded amino acid sequence of the reporter construct. The inactive IFP in our reporter is itself fused to a split-GFP (FIG. 11). The split-GFP is constitutively fluorescent and provides a marker of the presence of the reporter. It also acts to stabilize the IFP both before and after activating cleavage. However, the GFP itself is not cleaved and is not responsive to the presence of GzB. This inactive IFP was generated by splitting wild-type IFP, inverting the N- and C-terminal halves, and separating the N- and C-terminal halves with a linker, as described by To et al. PNAS 112(11): 3338-3343 (2015). The linker keeps the two halves of the protein from properly folding into an active, fluorescent IFP. However, upon cleavage of the linker region, the halves of IFP are able to come together and mature, resulting in a protein that is fluorescent.

In this GzB reporter, the linker between the halves of IFP is replaced with an amino acid sequence that is specifically cleaved by GzB and not other proteases. As a result, GzB activity can be detected by quantifying the mature IFP signal in each cell. GzB is the external protease that is delivered by CTLs and can activate the reporter by cleaving a linker separating parts of an inactive IFP protein. The GFP in the reporter is not cleaved and provides a constitutive fluorescent signal.

As the term "functionally separated" is used herein to refer to the GzB cleavage site, this refers to a separation of parts of a molecule with the cleavage site to thereby inactivate it, wherein cleavage promotes or restores the function (fluorescence). In general, the reporter does not include a pair of fluorochromes that form a FRET pair, or wherein one of the fluorophores is quenched.

A number of alternative GzB reporters are contemplated that serve the purpose of allowing for the detection of GzB activity in target cells that have been productively recognized by a CTL. These reporters can be used independently or in combination with the fluorogenic protease reporter described above to isolate target cells recognized by CTLs. For example, a small 16 aa peptide (GFP11) from GFP or mCHerry can be used to activate a GFP or mCHerry lacking the peptide. That peptide is fused to a protein where it was inactive, but activated when liberated by Granzyme cleavage. See, e.g., Kamiyama et al., Nat Commun. 2016; 7: 11046.

Figure 7A:
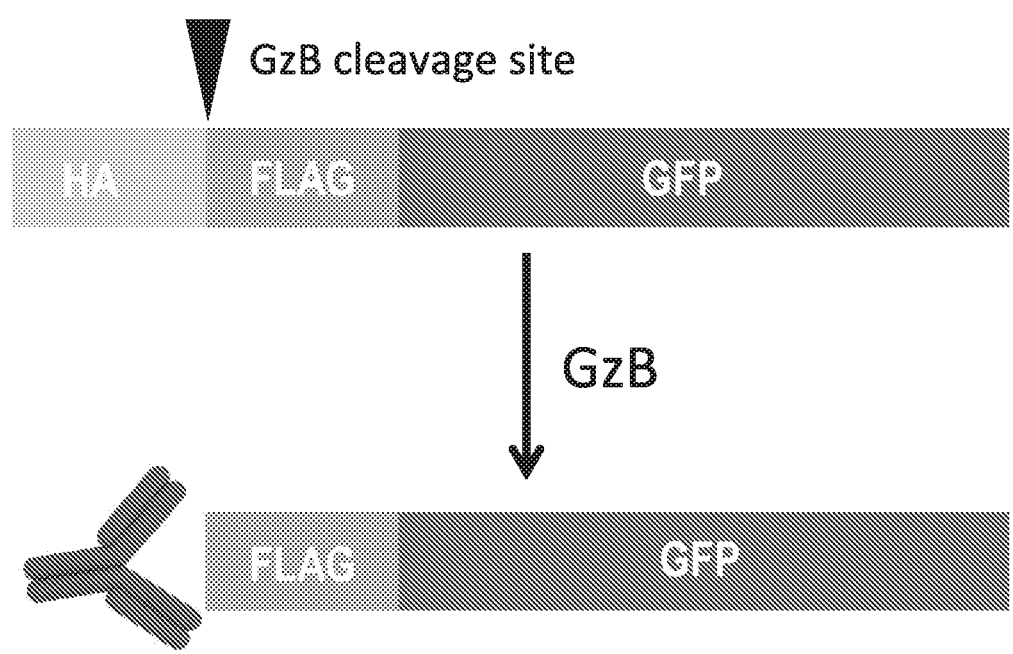
FIGS. 7A-7B depict development of an exemplary antibody-based reporter of GzB activity.

In some embodiments, the molecular reporter is an affinity tag (e.g., a flag epitope). Detection is based on staining for an antibody target that is only revealed following GzB cleavage of a reporter that serves as a substrate for GzB. The affinity tag can be located C-terminal to the GzB cleavage site such that the tag is only functional (e.g., Flag epitope recognized by an M1 flag antibody) upon cleavage of the GzB site. One embodiment is illustrated in FIG. 7A. Prior to cleavage, the internal tag (e.g., Flag epitope) is not recognized by the M1 Flag antibody, which only recognizes N-terminal Flag epitopes. However, following GzB cleavage, the tag is exposed at the N-terminus of the C-terminal cleavage fragment and can be stained using an appropriate binding partner (e.g., the M1 antibody). In some embodiments, the molecular reporter further has a GFP located proximally to the internal tag. In some embodiments, the GFP is located C-terminal to the tag.

In some embodiments, the molecular reporter is a plasma membrane protein linked to an endoplasmic reticulum (ER) retention sequence with a linker comprising a GzB cleavage site. When intact, the reporter is retained in the ER. Cleavage of the linker results in release of the ER retention sequence, and trafficking of the protein to the plasma membrane, where the protein can be recognized by an extracellularly applied antibody (or antigen-binding fragment thereof). This antibody can be used to isolate or purify the APCs that express a recognized epitope. This approach converted a proteolytic signal into the accessibility of an epitope, e.g., presence of a reporter protein on the cell surface. The antigen becomes accessible to an antibody or other binding moiety by virtue of granzyme cleavage either because it generates a unique binding site or changes its location (cellular, or in a protein). Any binding protein that becomes capable of binding can be used; for example an interacting pair of proteins can be used wherein one of them is fused to a protein that interferes with the association. Granzyme cleavage of the blocking segment would allow the protein to be detected by its binding partner. Nucleic acid aptamers can also be used in place of antibodies.

This enables the isolation of GzB-positive cells with affinity reagents such as fluorescent antibodies against the reporter protein (coupled with FACS) or by direct capture of GzB-positive cells in affinity columns (such as MACS cell separation columns). As a result, any reporter protein that is not endogenously present on the cell surface can be used, including CD4, CD19, CD20, CD40, or tagged versions of other proteins such as, but not limited to, a Myc tag, a Flag tag, an HA tag, and a histidine tag). See, e.g., Kimple, M. E., Brill, A. L., Pasker, R. L. (2013) Overview of Affinity Tags for Protein Purification. Curr Protoc Protein Sci. 73: Unit-9.9.

Figure 6A:
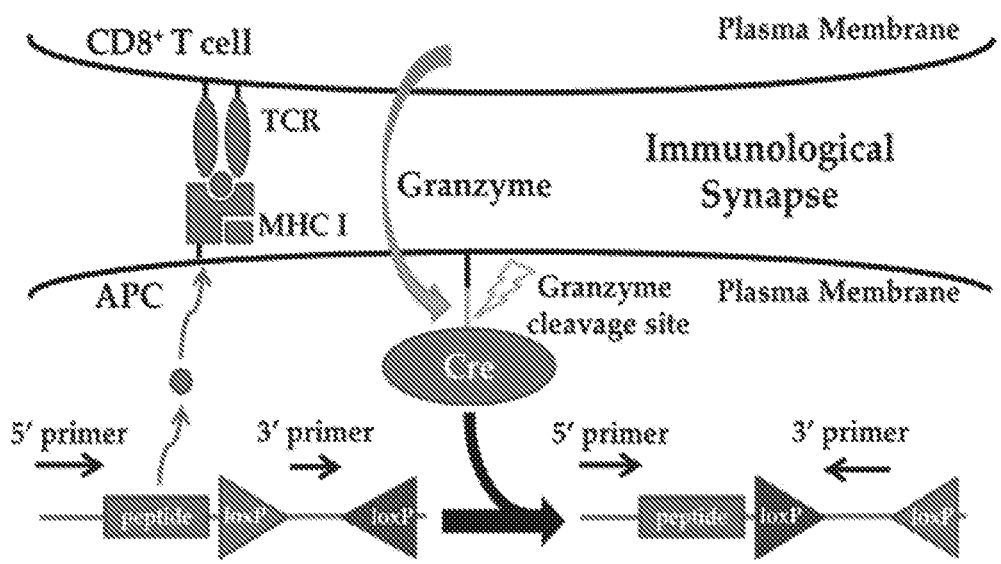
FIGS. 6A-6B depict development of an exemplary Cre reporter of GzB activity.

In some embodiments, the detection molecule is an enzyme. The fusion polypeptide comprises the enzyme (e.g., CRE recombinase) functionally linked to a plasma membrane attachment peptide (e.g., MGVKVLFALICIAVAE-ASSGSSGDYKDDDDKPVQPMALIVLG GVAGLLL-FIGLGIFFCVRCRHRRRQ (SEQ ID NO:7)) such that upon expression the fusion protein, the protein is found only at the plasma membrane of the expressing cell. The enzyme and the membrane attachment protein are separated by the GzB cleavage site such that upon cleavage, the enzyme is released from the plasma membrane. One example of this is the Cre recombinase protease reporter described in the Examples section herein. The Cre recombinase is inactive when tethered to the membrane by the membrane attachment peptide, but is activated by GzB cleavage which releases the Cre to enter the nucleus and activate a reporter of the Cre activity therein. In some embodiments, the reporter within the APC nucleus utilizes the Cre-mediated recombination of a LoxP reporter to indicate activity. In some embodiments, Cre activity is detected through the activation of a cellular reporter. In this approach, Cre activity in recognized target cells turns on a reporter gene (GFP, puromycin, etc.) that enables the isolation of cells, for example by FACS or with an antibiotic selection. Then the genomic DNA from just these cells can be isolated. The GFP/RFP inversion cassette is an example of a cellular reporter that creates a fluorescent signal in response to Cre activity. In some embodiments, the recombination of the Lox P reporter generates a primer configuration that allows for PCR amplification of the antigen cassette in the recognized cell. The antigens that are productively recognized can be identified by Illumina sequencing of the PCR product from target cells after treatment with cytotoxic cells. This approach is diagrammed in FIG. 6A. Other useful enzymes for use as detection molecules in the compositions and methods herein are TEV protease, and transcription factors. In some embodiments, the membrane attachment signal peptide is (SEQ ID NO: 8)
MALPVTALLLPLALLLHAARPSQ.

In addition, described herein are systems for detection of Granzyme B activity in an APC. Such systems can utilize two separate reporting constructs that interact to indicate Granzyme B activity. The systems preferably contain a fusion polypeptide comprising a CRE recombinase linked to a plasma membrane attachment peptide, described herein, where the CRE recombinase and membrane attachment peptide are separated by a GzB cleavage site. The systems can further contain a reporter of CRE activity as described herein. The reporter of CRE activity can be a nucleic acid sequence encoding GFP and RFP in head to head orientation flanked by LoxP sites. The system may alternatively or further contain a nucleic acid sequence encoding a candidate antigen in expressible form, located proximally to a CRE activated primer recognition sequence comprising an inactive primer flanked by LoxP sites, wherein CRE induced rearrangement of the LoxP sites produces a functional primer recognition sequence. This CRE-mediated inversion event can be directly detected in the genomic DNA by PCR and sequencing. For this approach, a Cre-mediated inversion event can create the proper primer orientation to enable PCR amplification of the antigen-presenting cassette. The genomic DNA from all of the target cells (without any sorting) can be extracted and PCR from this bulk gDNA will amplify the antigen-presentation cassettes only from the target cells that received GzB, activated Cre, and inverted the primer surrounding the antigen-presentation cassette. This approach was used with qPCR to quantify the frequency of the inversion event in the proof-of-concept experiment of FIG. 6. These two approaches can be used independently or in combination.

Labels

Suitable detection molecules which may be incorporated into the reporter molecules described herein include, without limitation, radioactive isotopes, fluorescers, chemiluminescers, chromophores, enzymes, enzyme substrates, enzyme cofactors, enzyme inhibitors, dyes, metal ions, metal sols.

Any fluorescent polypeptide (also referred to herein as a fluorescent label) may be suitable for use as a detectable label. A suitable fluorescent polypeptide will be one that will readily provide a detectable signal that can be assessed qualitatively (positive/negative) and quantitatively (comparative degree of fluorescence).

Exemplary fluorescent polypeptides include, but are not limited to, yellow fluorescent protein (YFP), cyan fluorescent protein (CFP), GFP, mRFP, RFP (tdimer2), HCRED, etc., or any mutant (e.g., fluorescent proteins modified to provide for enhanced fluorescence or a shifted emission spectrum), analog, or derivative thereof. Further suitable fluorescent polypeptides, as well as specific examples of those listed herein, are provided in the art and are well-known.

Biotin-based labels also find use in the methods disclosed herein. Biotinylation of target molecules is well known, for example, a large number of biotinylation agents are known, including amine-reactive and thiol-reactive agents, for the biotinylation of proteins, nucleic acids, carbohydrates, carboxylic acids; see, e.g., chapter 4, Molecular Probes Catalog, Haugland, 6th Ed. 1996, hereby incorporated by reference. A biotinylated substrate can be detected by binding of a detectably labeled biotin binding partner, such as avidin or streptavidin. Similarly, a large number of haptenylation reagents are also known.

Exemplary affinity tags suitable for use include, but are not limited to, a monocytic adaptor protein (MONA) binding peptide, a T7 binding peptide, a streptavidin binding peptide, a polyhistidine tract, protein A (Nilsson et al, EMBO J. 4: 1075 (1985); Nilsson et al, Methods Enzymol. 198:3 (1991)), glutathione S transferase (Smith and Johnson, Gene 67:31 (1988)), Glu-Glu affinity tag (Grussenmeyer et al, Proc. Natl. Acad. Sci. USA 82:7952 (1985)), substance P, FLAG peptide (Hopp et al, Biotechnology 6: 1204 (1988)), or other antigenic epitope or binding domain. See, in general, Ford et al, Protein Expression and Purification 2:95 (1991). DNA molecules encoding affinity tags are available from commercial suppliers (e.g., Pharmacia Biotech, Piscataway, N.J.).

Identifying Antigens in the Activated APC

Additionally, provided herein are systems for detection of recognized antigen presentation by an antigen presenting cell to a cytotoxic lymphocyte. The systems contain an antigen presenting cell, or a plurality of antigen presenting cells, containing an exogenous nucleic acid encoding a candidate antigen, wherein the candidate antigen is expressed and presented with MHC class I and/or MHC class II molecules to cytotoxic lymphocytes, as described herein. The systems further contain a molecular reporter of Granzyme B activity as described herein, or a system for detecting granzyme B activity, as described herein. In some embodiments, the systems further contain a cytotoxic lymphocyte, as described herein. In some embodiments, the antigen presenting cells of the systems further comprise an inhibitor of CAD-mediated DNA degradation, such as an ICAD gene in expressible form.

As described herein, productive antigen recognition presented on the recognized target APC by the cytotoxic lymphocyte results in recognizable changes within the APC. Detection of such changes is used in the identification of the APC and eventual determination of the antigen(s) it expressed. Identification of the recognized target cell and identification of the antigen therein, can be accomplished by use of high-throughput systems that detect the reporters therein to thereby isolate and/or sort the identified cells.

Isolating and/or sorting as described herein may be conducted using a variety of methods and/or devices known in the art, e.g., flow cytometry (e.g., fluorescence activated cell sorting (FACS) or Ramen flow cytometry), fluorescence microscopy, optical tweezers, micro-pipettes, affinity purification, and microfluidic magnetic separation devices and methods. In some embodiments, where the detectably labeled target cell is a fluorescently labeled target cell, FACS may be utilized to quantitatively sort the cells based on one or more fluorescence signals. In an exemplary embodiment, when target cells comprising the candidate antigens specifically bind their cognate T cells, the target cells will emit an infrared fluorescent signal (for example, from the activated IFP-GFP fusion protein encoded by the target cells). FACS may be used to sort the bound cells from the unbound cells based on the infrared fluorescent signal. One or more sort gates or threshold levels may be utilized in connection with one or more detection molecules to provide quantitative sorting over a wide range of target cell-T cell interactions. In addition, the screening stringency may be quantitatively controlled, e.g., by modulating the target concentration and setting the position of the sort gates.

Where, for example, the fluorescence signal is related to the binding affinity of the candidate antigen to the cytotoxic lymphocyte (such as a CTL), the sort gates and/or stringency conditions may be adjusted to select for antigens having a desired affinity or desired affinity range for the target. In some cases, it may be desirable to isolate the highest affinity antigens from a particular library of candidate antigens sequences. However, in other cases candidate antigens falling within a particular range of binding affinities may be isolated.

Cells identified as having recognized antigen can be processed to isolate the exogenous nucleic acid. In some embodiments, the exogenous nucleic acid is isolated by PCR amplification using known primer sequences (e.g., known from the transfection of the nucleic acid into the APC). Alternatively, RT-PCR can be used to amplify the transcribed form of the antigen cassette. If the antigen is expressed episomally (as part of a viral genome or plasmid), the episomal DNA can be captured as a way of isolating the antigen-presenting cassette. Determination of the specific recognized antigen therein can be accomplished by use of high-throughput systems such as DNA sequencing.

A number of DNA sequencing techniques are known in the art, including fluorescence-based sequencing methodologies (See, e.g., Birren et al., Genome Analysis: Analyzing DNA, 1, Cold Spring Harbor, N.Y.). In some embodiments, automated sequencing techniques understood in the art are utilized. In some embodiments, the high-throughput systems described herein use methods that provide parallel sequencing of partitioned amplicons (e.g., PCT Publ. No. WO 2006/084132). In some embodiments, DNA sequencing is achieved by parallel oligonucleotide extension (See, e.g., U.S. Pat. Nos. 5,750,341, and 6,306,597). Additional examples of sequencing techniques include the Church polony technology (Mitra et al., 2003, *Analytical Biochemistry* 320, 55-65; Shendure et al., 2005 *Science* 309, 1728-1732; U.S. Pat. Nos. 6,432,360, 6,485,944, 6,511,803), the 454 picotiter pyrosequencing technology (Margulies et al., 2005 *Nature* 437, 376-380; US 20050130173), the Solexa single base addition technology (Bennett et al., 2005, *Pharmacogenomics*, 6, 373-382; U.S. Pat. Nos. 6,787,308; 6,833, 246), the Lynx massively parallel signature sequencing technology (Brenner et al. (2000). *Nat. Biotechnol.* 18:630-

634; U.S. Pat. Nos. 5,695,934; 5,714,330), and the Adessi PCR colony technology (Adessi et al. (2000). Nucleic Acid Res. 28, E87; WO 00018957).

Next-generation sequencing (NGS) methods share the common feature of massively parallel, high-throughput strategies, with the goal of lower costs in comparison to older sequencing methods (see, e.g., Voelkerding et al., Clinical Chem., 55: 641-658, 2009; MacLean et al., Nature Rev. Microbiol., 7:287-296). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by ILLUMINA™, and the Supported Oligonucleotide Ligation and Detection™ (SOLiD) platform commercialized by APPLIED BIOSYSTEMS™. Non-amplification approaches, also known as single-molecule sequencing, are exemplified by the HELISCOPE™ platform commercialized by HELICOS BIOSYSTEMS™, and emerging platforms commercialized by VISIGEN™, OXFORD NANOPORE TECHNOLOGIES LTD., and PACIFIC BIOSCIENCES™, respectively.

In pyrosequencing (Voelkerding et al., Clinical Chem., 55: 641-658, 2009; MacLean et al., Nature Rev. Microbial., 7:287-296; U.S. Pat. Nos. 6,210,891; 6,258,568), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the SOLEXA/ILLUMINA platform (Voelkerding et al., Clinical Chem., 55. 641-658, 2009; MacLean et al., Nature Rev. Microbiol., 7:287-296; U.S. Pat. Nos. 6,833,246; 7,115,400; 6,969,488), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLID™ technology (Voelkerding et al., Clinical Chem., 55: 641-658, 2009; MacLean et al., Nature Rev. Microbial., 7:287-296; U.S. Pat. Nos. 5,912,148; 6,130,073) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLID™ system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing is employed (see, e.g., Astier et al., J. Am. Chem. Soc. 2006 Feb. 8; 128(5)1705-10). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, HELISCOPE™ by HELICOS BIOSCIENCES™ is employed (Voelkerding et al., Clinical Chem., 55. 641-658, 2009; MacLean et al., Nature Rev. Microbial, 7:287-296; U.S. Pat. Nos. 7,169,560; 7,282,337; 7,482,120; 7,501,245; 6,818,395; 6,911,345; 7,501,245). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is about 99.6% for 50 base reads, with ~100 Mb generated per run. The read-length is 100 base pairs. The accuracy for homopolymer repeats of 5 repeats in length is ~98%.

Another exemplary nucleic acid sequencing approach that can be adapted for use with the methods described herein was developed by STRATOS GENOMICS, Inc. and involves the use of XPANDOMERS™. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an XPANDOMER™ of a length longer than the plurality of the subunits of the daughter strand. The XPANDOMER™ typically includes the tethers and reporter elements for parsing genetic information in a sequence corresponding to the contiguous nucleotide sequence of all or a portion of the target nucleic acid. Reporter elements of the XPANDOMER™ are then detected. Additional details relating to XPANDOMER™-based approaches are described in, for example, U.S. Pat. Publ. No. 20090035777, entitled "HIGH THROUGHPUT NUCLEIC ACID SEQUENCING BY EXPANSION," filed Jun. 19, 2008, which is incorporated herein in its entirety.

Other emerging single molecule sequencing methods include real-time sequencing by synthesis using a VISIGEN™ platform (Voelkerding et al., *Clinical Chem.*, 55: 641-58, 2009; U.S. Pat. No. 7,329,492; U.S. patent application Ser. No. 11/671,956; U.S. patent application Ser. No. 11/781,166) in which immobilized, primed DNA template is subjected to strand extension using a fluorescently-modified polymerase and florescent acceptor molecules, resulting in detectible fluorescence resonance energy transfer (FRET) upon nucleotide addition.

Unless otherwise defined herein, scientific and technical terms used in connection with the present application shall have the meanings that are commonly understood by those of ordinary skill in the art. Allen et al., *Remington: The Science and Practice of Pharmacy* $22^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* $3^{rd}$ ed., revised ed., J. Wiley & Sons (New York, N.Y. 2006); Smith, *March's Advanced Organic Chemistry Reactions, Mechanisms and Structure* $7^{th}$ ed., J. Wiley & Sons (New York, N.Y. 2013); Singleton, *Dictionary of DNA and Genome Technology* $3^{rd}$ ed., Wiley-Blackwell (Nov. 28, 2012); and Green and Sambrook, *Molecular Cloning: A Laboratory Manual 4th ed.*, Cold Spring Harbor Laboratory Press (Cold Spring Harbor, NY 2012), provide one skilled in the art with a general guide to many of the terms used in the present application. For references on how to prepare antibodies, see Greenfield, *Antibodies A Laboratory Manual* $2^{nd}$ ed., Cold Spring Harbor Press (Cold Spring Harbor NY, 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7. Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used to described the present invention, in connection with percentages means ±5%.

In one respect, the herein described compositions, methods, and respective component(s) thereof, are essential, yet open to the inclusion of unspecified elements, essential or not ("comprising). In some embodiments, other elements to be included in the description of the composition, method or respective component thereof are limited to those that do not materially affect the basic and novel characteristic(s) thereof ("consisting essentially of"). This applies equally to steps within a described method as well as compositions and components therein. In some embodiments, the compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention is further illustrated by the following examples, which should not be construed as further limiting.

EXAMPLES

Materials and Methods

The following materials and methods were used in the Examples herein.

Preparation of T Cells

A clonal T cell recognizing the IV9 epitope (aa 309-317 of HIV Pol, ILKEPVHGV) was kindly provided by Bruce Walker. T cells were cultured in RPMI with 10% FBS (Gibco), 1% penicillin-streptomycin (Gibco), and 50 U/ml human recombinant IL-2 (Roche). T cells were expanded by culturing 1E6 T cells with 20E6 irradiated (50 Gy) allogeneic PMBCs in the presence of anti-CD3 (OKT3, 0.1 ug/ml).

For the revival of TCRs, primary CD8 T cells were purified from donor blood using the RosetteSep CD8 T cell purification kit (StemCell). 1E6 T cells were activated using anti-CD3/anti-CD28 magnetic beads (Invitrogen) and simultaneously transduced with a lentiviral vector encoding the TCR of interest and a Zesty Green (Zsg) fluorescent marker.

Transduced cells were sorted by FACS (BD FACSAria™ II) based on Zsg signal (FITC channel) after 5 days.

NK cells were purified from donor blood using the RosetteSep NK cell purification kit (StemCell) and activated for 24 h in 100 U/ml IL-2 in RPMI and 10% FBS.

Cytotoxicity Assays

Hmy2.CIR-HLA-A2 target cells were labeled with CFSE (Invitrogen) according to the manufacturer's protocol and pulsed with 10 ug/ml IV9 peptide (NeoBioLab) or a control peptide (NeoBioLab) for 1 hr. Cells were washed 3× with PBS. 5E4 target cells were plated per well in a 96-well plate and mixed with a 10-fold excess of IV9 T cells, spun down at 300 g for 2 min and incubated at 37 C for 4 h. Cells were resuspended by pipetting and incubated with 7-AAD (BD Biosciences) at a 1:20 dilution for 10 min. Target cells were identified by CFSE staining (FITC) and dead cells were detected in the PerCP-Cy5.5 channel (BD FACSAria™ II). For the LDH assay, the supernatant after 4 h incubation was collected and processed according to the manufacturer's protocol (Pierce).

Fluorogenic GzB Reporter

The fluorogenic GzB reporter was generated by replacing the TEV cleavage site in the iTEV-HO1 vector (To et al. PNAS 112(11): 3338-3343 (2015)) with the GzB cleavage sequence (VGPDFGR (SEQ ID NO:9), Choi, P. J. and Mitchison, T. J. (2013) *PNAS* 110(15): 6488-6493). The new reporter was cloned into the pHAGE TRex hygromycin lentiviral expression vector and transduced into HEK293T cells at an MOI of ~1. Cells were selected with 200 ug/ml hygromycin for 4 d. Target cells were distinguished from T cells based on GFP signal and activation of the reporter was detected by an increase in fluorescence in the APC-Cy7 channel (BD FACSAri™a II).

Cre Reporter of GzB Activity

Figure 14:
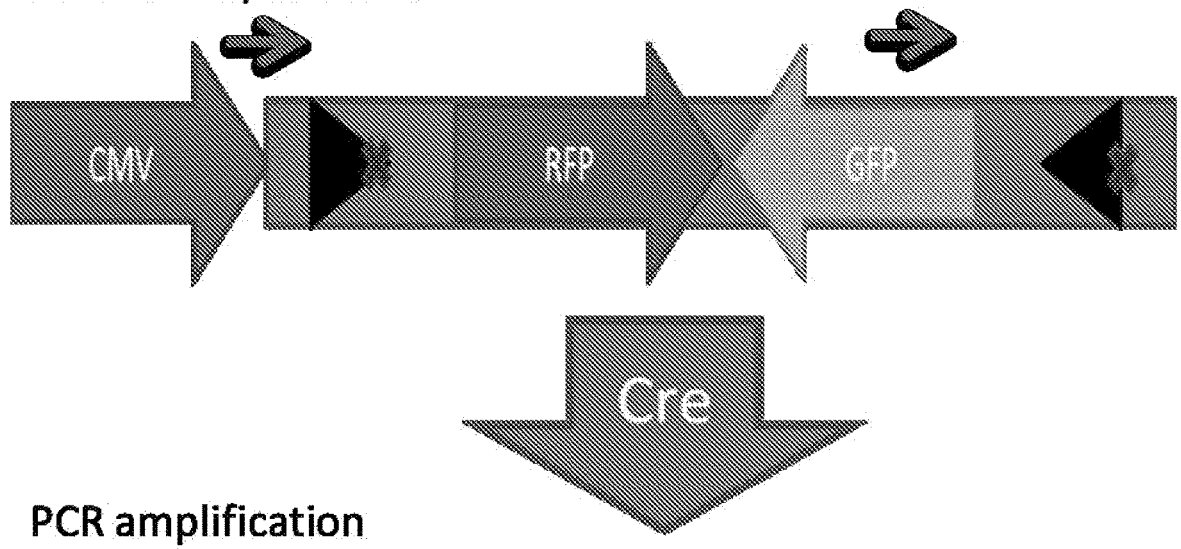
FIG. 14 shows qPCR primers designed to facilitate detection of the inversion event in a reporter cassette for the presence of Cre by qPCR rather than by fluorescent detection via the activation of GFP and loss of RFP.
Figure 14:
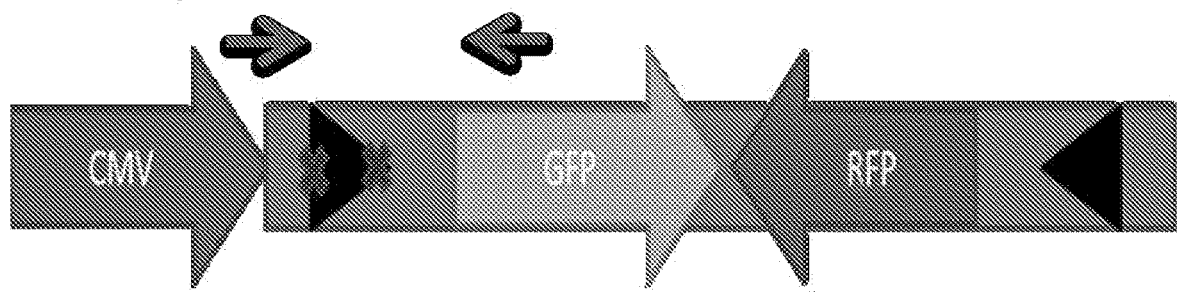
Figure 15:
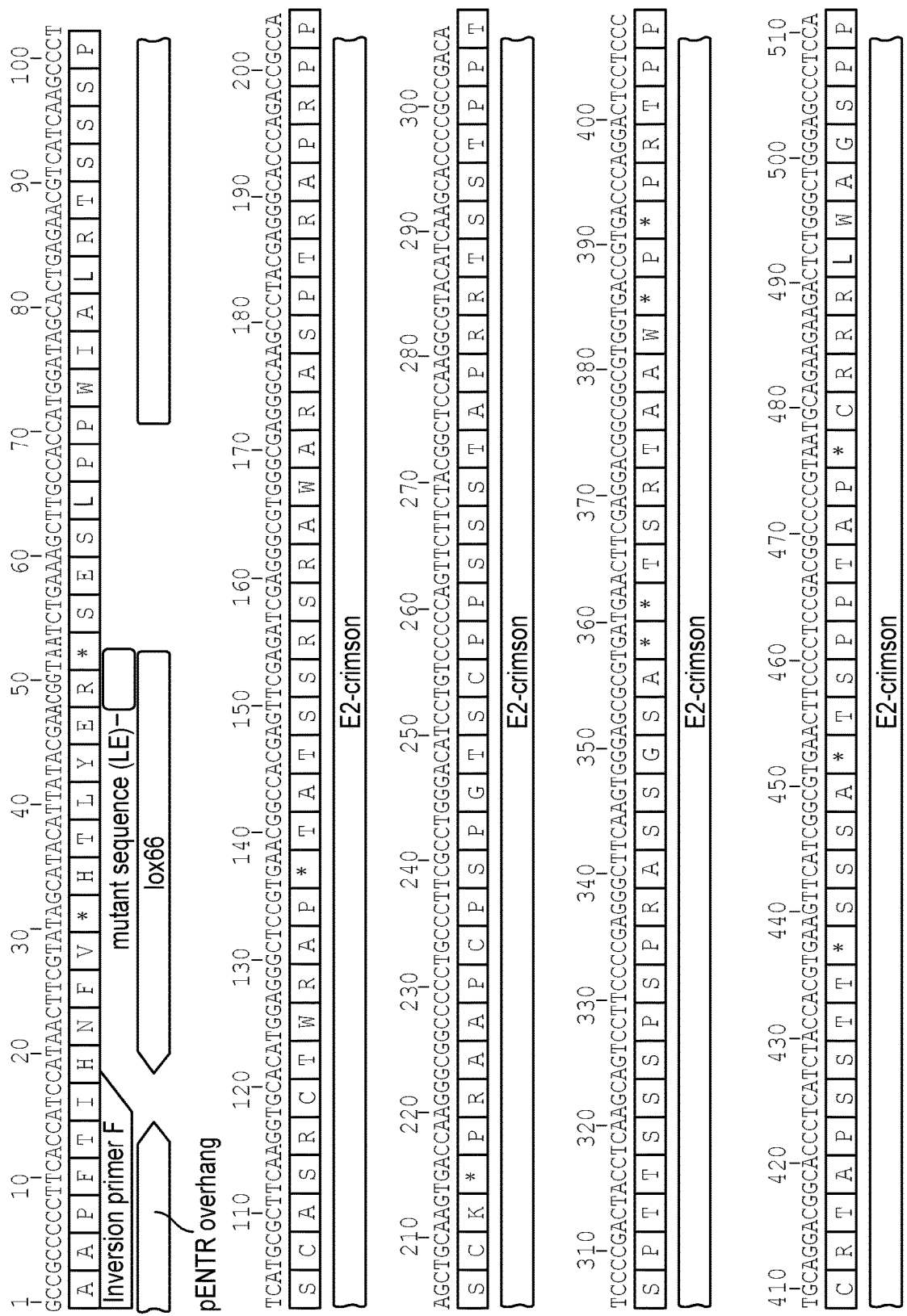
FIG. 15 shows the nucleotide (SEQ ID NO:3) and amino acid (SEQ ID NO:34) sequence of an exemplary reporter cassette for the presence of Cre that enables fluorescent detection of Cre activity via the activation of GFP and loss of RFP.

A construct was generated that encoded a membrane-tethered Cre fusion containing a signal peptide (MALPVTALLLPLALLLHAARPSQ (SEQ ID NO:8)), a flag tag (DYKDDDDK (SEQ ID NO:10)), the CD8 transmembrane domain, the GzB cleavage site (VGPDFGR (SEQ ID NO:9)), and Cre recombinase. This construct was synthesized (IDT) and cloned into the pENTR vector (ThermoFisher) and then into the lentiviral pHAGE CMV hygro destination vector and introduced into K562 target cells by lentiviral transduction. As a reporter of Cre activity, a vector was used that contained GFP and RFP in a head-to-head orientation flanked by loxP sites. This is a reporter cassette for the presence of Cre that enables fluorescent detection of Cre activity via the activation of GFP and loss of RFP. In addition, qPCR primers (diagrammed in FIG. 14, sequence shown in FIG. 15) were designed that allowed detection of this same inversion event by qPCR rather than by fluorescent detection. This reporter cassette was cloned into a pHAGE CMV lentiviral vector and introduced into reporter cells by lentiviral transduction (hygromycin selection 4 d at 200 ug/ml). Finally, the caspase-resistant D117E ICAD gene was introduced into the target cells by lentiviral transduction (blasticidin selection 5 d at 40 ug/ml). The target cells were mixed with a 2:1 excess of activated primary NK cells for 4 h. Genomic DNA was purified using the GeneJET™ purification kit and the inversion of the Cre reporter was quantified by quantitation of the PCR amplification product by qPCR using inversion-specific primers. The inversion cassette itself contained RFP and GFP for fluorescent detection of Cre activity in other contexts, but the fluorescent signals were not used at all in this experiment. The signal was normalized to a set of primers that quantified the reporter cassette regardless of orientation.

Antibody-Based GzB Reporter

A construct encoding a fusion of an HA tag (YPYDVPDYA (SEQ ID NO: 11)), GzB cleavage site (VGPD (SEQ ID NO:1)), Flag tag (DYKDDDDK (SEQ ID NO: 10)), and GFP was synthesized (IDT) and cloned into the pENTR vector (ThermoFisher) and then the pHAGE Trex neo expression vector by Gateway cloning. HEK293T cells were transfected with the expression vector or a control empty vector and then co-cultured with primary NK cells for 2 h. Cell lysates were harvested and run on a 4-12% Bis-Tris gel and blotted with the M1 anti-Flag antibody (Sigma Aldrich).

CD4 TCR Test

The alpha and beta chains of the OB1a.12 TCR (specific for the MBP peptide) separated by a P2A sequence were cloned into the pHAGE EF1a-PGK-Zsg vector. As a control, the alpha and beta chains of a TCR targeting the IV9 peptide (Kolowos, W. et al. (1999) Journal of Immunology, 162: 7525-7533) were cloned into the same vector. Primary CD8 T cells re-stimulated with anti-CD3/anti-CD28 magnetic beads (Invitrogen) were transduced with lentivirus expressing the OB1a.12 or control TCR. After 5 d, Zsg-positive T cells were sorted by FACS. OB1a.12 or control T cells were co-cultured with HEK293T cells expressing the fluorogenic GzB reporter alone or with a single-chain MHC II construct with the MBP peptide or mutants of the MBP peptide. Activation of the GzB reporter was detected after 4 h by FACS.

Mixing Experiment

A 56 aa fragment containing the IV9 epitope (GAKALT-DIVPLTREAELELAENKEILKEPVHGVYYDSAKELI-AEVQKQGLDQWTY Q; SEQ ID NO:12) was cloned into a pHAGE CMV puro lentiviral expression vector. HEK293T cells expressing the fluorogenic GzB reporter were transduced with lentivirus to express this IV9 epitope or with a control lentivirus (MOI~1) and selected with 1 ug/ml puromycin for 3 days. Cells expressing the IV9 construct were labeled with CellTrace™ Violet cell dye according to manufacturer's protocol (Invitrogen) and mixed with unlabeled control cells at various ratios and plated in 96-well plates. After 12 h of growth, a 10:1 ratio of IV9 T cells was added and the cells were co-cultured for 4 h. The cells were resuspended by pipetting and analyzed by flow cytometry (BD FACSAria™ II) for GFP, APC-Cy7, and DAPI (violet dye).

IV9 T Cell Screen

A library of 2494 oligos encoding 56aa fragments tiling across the complete proteomes of 10 HIV strains was synthesized (Agilent). The library was amplified using the following primers:

```
HIV_lib_F
                                            (SEQ ID NO: 13)
5' ggggacaagtttgtacaaaaaagcaggetcaAGAATTCTCCGTGGC HIV_lib_R
                                            (SEQ ID NO: 14)
5' ggggaccactttgtacaagaaagagggtcagetagttaCACTCGAGA
GCTCAC
``` and cloned into the pDONR221 vector. The capitalized section indicates the region that is directly complementary to our antigen cassette (the lower case is an overhang that is being added on by PCR). The library was then cloned into the pHAGE CMV N-FlagHA IRES puro destination vector using LR clonase. Two replicates of 30E6 target cells (HEK293T expressing GzB reporter and ICAD) were transduced with the HIV peptide library at an MOI~0.2 and selected for 3 d with 1 ug/ml puromycin. 3E6 target cells from each replicate were co-cultured with 10E6 activated IV9 T cells for 12 h. Cells were resuspended by pipetting and target cells activating the GzB reporter were sorted by FACS. Genomic DNA was purified from the sorted cells and 3E6 pre-sorted controls using the GeneJET™ kit (Thermo). The peptide cassette was amplified using the following primers:

T_cell_PCR1_F 5'CCAGTCAGGTGTGATGCTCGGG-GATCCAGGAATTCAGTTTGTACAAAAAAGCAG GCTCA (SEQ ID NO:15); T_cell_PCR1_R 5'CGAGCT-TATCGTCGTCATCCCCACTTTGTA-CAAGAAAGCTGGGTCA (SEQ ID NO:16) and 1 ul of PCR1 product was used as template for two rounds of library prep PCR as previously described (Xu, et al., (2015) Science, 348 (6239) aaa0698) and the products were pooled, gel extracted, and submitted for single-end 300 bp sequencing on the Illumina MiSeq. Reads were aligned using BWA and the abundance of each peptide in the sorted population relative to the input frequency was calculated.

CMV Sub-Library Screen

This screen was performed as the IV9 T cell screen described above with the following modifications. Briefly, the NLV2 TCR (Schub et al., J Immunol, 183:6819-6830 (2009)) was synthesized as a gBlock fragment (IDT), cloned into the pHAGE EF1a Zsg DEST lentiviral vector, packaged into lentivirus, and transduced into primary CD8 T cells. A library of 5,784 oligos encoding the complete proteome of the CMV Merlin strain in duplicate was synthesized on a releasable microarray (Twist Biosciences), cloned into the pHAGE CMV NFlagHA puro DEST lentiviral vector, packaged into lentivirus, and transduced into HLA-A2 target cells (MHC Null HEK293T/dmICAD-bsd/iGzB-hyg/HLA-A2) at an MOI of around 0.5 (selected with 1 ug/ml puromycin for 3 d).

Three replicates of 10E6 CMV target cells were co-cultured with 50E6 NLV2 T cells for 12 h, after which, IFP-positive target cells were sorted (FACSAria™ II). Sorted cells were spun down at 500 g for 5 min and gDNA was extracted using the GeneJET™ Genomic DNA purification kit (Thermo). Sequencing adaptors and multiplexing indexes were added in three rounds of PCR as described for the IV9 T cell screen above and the samples were submitted for high-throughput sequencing on the Illumina MiSeq. Reads were aligned using BWA and the abundance of each peptide in the sorted population relative to the input frequency was calculated.

Virome-Wide Screen

This screen was performed as the IV9 T cell screen described above with the following modifications. Briefly, pp65-specific primary T cells were kindly provided by Kim Lyerly. The VirScan library (Xu et al. Science, 348 (6239), aaa0698 (2015)) was cloned into the pHAGE CMV NFlagHA puro DEST lentiviral vector, packaged into lentivirus, and transduced into HLA-A2 target cells (MHC Null HEK293T/dmICAD-bsd/iGzB-hyg/HLA-A2) at an MOI of around 0.5 (selected with 1 ug/ml puromycin for 3 d).

Four replicates of 120E6 virome target cells were co-cultured with 120E6 T cells for 12 h, after which, IFP-positive target cells were sorted (FacsAria™ II). Sorted cells were spun down at 500 g for 5 min and gDNA was extracted using the GeneJET™ Genomic DNA purification kit (Thermo). Sequencing adaptors and multiplexing indexes were added in three rounds of PCR as described for the IV9 T cell screen above and the samples were submitted for high-throughput sequencing on the Illumina MiSeq. Reads were aligned using BWA and the abundance of each peptide in the sorted population relative to the input frequency was calculated.

CMV Library vs. Library Screen

This screen was performed as the CMV sublibrary screen described above with the following modifications. Memory T cells were purified from donor #224 PBMCs (76E6 starting cells, Astarte Biologicals) and expanded as described before.

Four replicates of 30E6 CMV target cells were co-cultured with around 25E6 T cells for 8 h after which IFP-positive target cells were sorted (FacsAria™ II) and processed as described above.

Tiling Mutagenesis Screen

This screen was performed as the IV9 T cell screen described before with the following modifications. Briefly, pp65-specific primary T cells were kindly provided by Kim Lyerly. A library of 3,376 oligos (CTL_mut library) encoding the complete set of single amino acid mutants of four T cell epitopes (including the pp65 epitope: NLVPMVATV) in duplicate was synthesized on a releasable microarray (Twist Biosciences), cloned into the pHAGE CMV NFlagHA puro DEST lentiviral vector, packaged into lentivirus, and transduced into HLA-A2 target cells (MHC Null HEK293T/dmICAD-bsd/iGzB-hyg/HLA-A2) at an MOI of around 0.2 (selected with 1 ug/ml puromycin for 3 d).

Three replicates of 25E6 CTL_mut target cells were co-cultured with 25E6 T cells for 12 h after which IFP-positive target cells were sorted (FacsAria™ II) and processed as described above.

Two Rounds of Selection Screen

This screen was performed as the IV9 T cell screen described above with the following modifications. Briefly, the IV9-specific "HA" TCR (Kolowos et al., J Immunol 162:7525-7533 1999) was synthesized as a gBlock fragment (IDT), cloned into the pHAGE EF1a Zsg DEST lentiviral vector, packaged into lentivirus, and transduced into primary CD8 T cells.

Three replicates of 5E6 target cells were co-cultured with 40E6 "HA" T cells for 10 h after which IFP-positive target cells were sorted (FacsAria™ II) and processed as described above.

To perform the second round of selection, the PCR1 product from each of the three screen replicates was cloned back into the pHAGE CMV NFlagHA puro DEST vector, packaged into lentivirus, and transduced into HLA-A2 target cells at an MOI of around 0.2. One replicate of 5E6 target cells expressing each of the three re-cloned libraries was co-cultured with 25E6 "HA" T cells for 10 h, after which IFP-positive target cells were sorted (FacsAria™ II) and processed as described above. Following sequencing and read alignment, the abundance of recovered peptides after one and two rounds of selection were compared to the pre-selected input library.

Details of Screening Optimization

To preserve genomic DNA after isolation of IFP-positive cells, sorted cells were maintained constantly on ice, spun down, and frozen within four hours of sorting.

To provide optimal signal-to-noise of target detection, an optimization experiment was performed immediately preceding each screen. Briefly, MHC-matched target cells (expressing iGzB reporter) in the presence or absence of the known T cell antigen (pulsed peptide, 10 ug/ml final) were co-cultured with serial dilutions of the T cells used for the screening for 4 h. Reporter activation was determined in each condition by flow cytometry and the ratio of the background activation (absence of pulsed antigen) and on-target activation (presence of pulsed antigen) was calculated. The optimal T cell:target cell ratio was selected for the library screen.

In order to reduce the number of cells displaying multiple antigens, target cells were transduced with lentiviral libraries at a Multiplicity of Infection (MOI) of 0.2-0.5.

To provide robust detection of antigen sequences, samples were sequenced to a depth of at least 2× the number of sorted cells (i.e., 200,000 reads for a sample where 100,000 cells were sorted by FACS).

To enable clearer separation of T cells and target cells by FACS, target cells are stained with CellTrace™ Violet dye (Invitrogen) prior to co-culture with T cells.

Example 1. Compositions and Methods for Identifying T Cell Antigens from a Complex Library by High Throughput Sequencing Disclosed herein are compositions and methods for comprehensive, genome-wide identification of the target antigens of T cells. The approach uses lentiviral delivery of candidate antigens for presentation on MHC Class I molecules in target cells. This library of target cells is then mixed with a sample of cytotoxic T lymphocytes (CTLs) of interest, and the CTLs are given time to recognize any target cells displaying their cognate antigen. Upon recognition, the CTLs release their cytotoxic granules, which contain the serine protease Granzyme B (GzB), in order to initiate the killing process. A reporter of intracellular GzB activity is used to isolate genomic DNA from the recognized target cells. Finally, PCR amplification and next generation sequencing (NGS) enable comprehensive identification of the antigens these cells had displayed. This provides a quantitative, sequencing readout of the antigens recognized by the input population of CTLs. This approach is illustrated in FIG. 1.

Figure 2B:
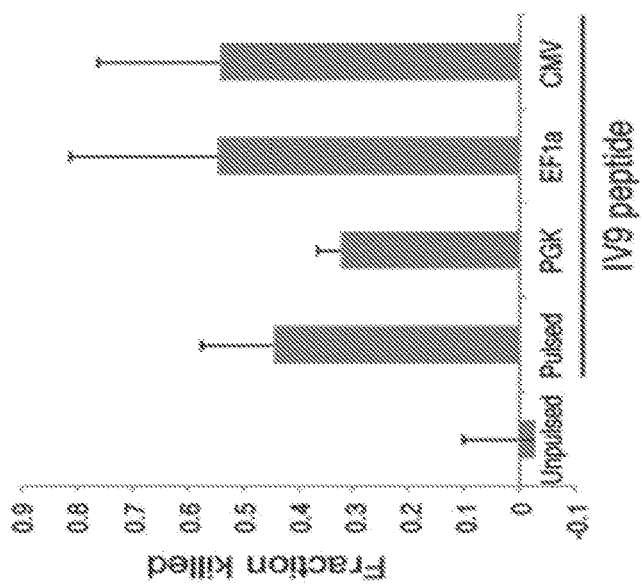
FIGS. 2A-2B depict exemplary positive controls for CTL-target interaction.
Figure 2A:
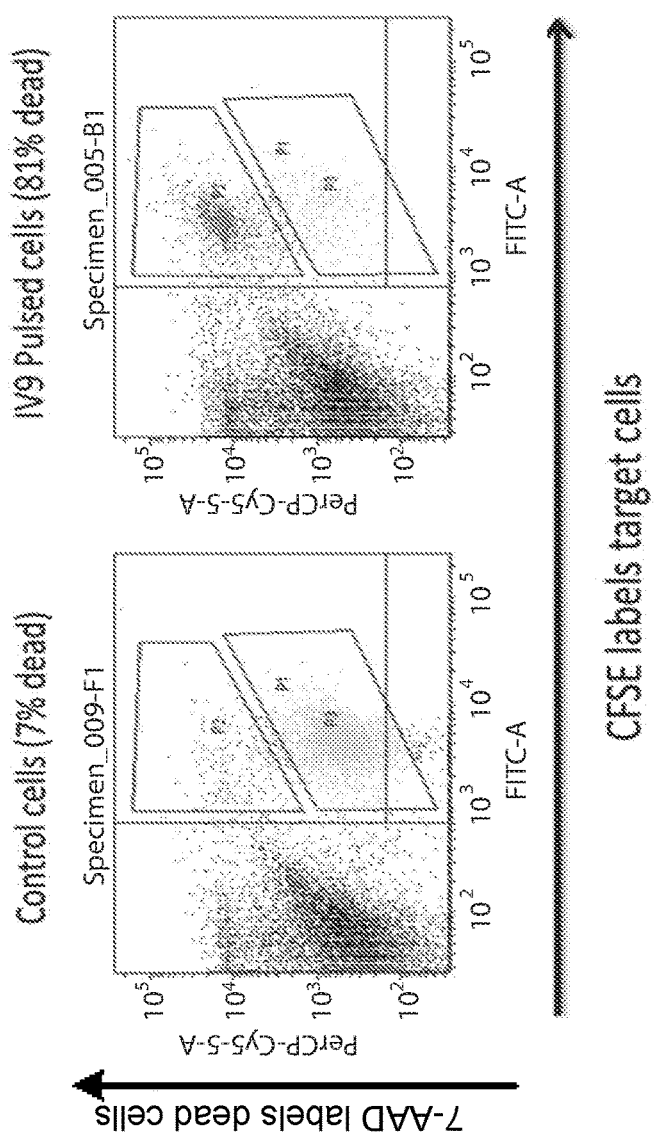

Proof of concept experiments were performed to demonstrate that methods for identifying candidate antigens specific to cytotoxic T cells can robustly enrich target cells displaying the cognate antigen of a CTL. For development and testing purposes, a well-characterized CTL clone specific to the HLA A*0201-restricted HIV pol peptide IV9 (Pol residues 476-484) was obtained. The CTL clone was able to induce apoptosis, as detected by 7-AAD staining for membrane permeability, in MHC-matched target cells pulsed with cognate but not control peptide (FIG. 2A).

Candidate antigens that are genetically encoded can be efficiently presented on MHC I molecules by target cells, which enables the generation of a target cell library. A test was performed to determine whether single copy lentiviral expression of a 56 amino acid fragment of HIV pol that contains the cognate IV9 sequence allows for efficient processing and presentation of the IV9 peptide. It was observed that expression of this fragment was sufficient to confer recognition of target cells by the IV9 CTLs, as determined by an LDH-release cytotoxicity assay (FIG. 2B). This demonstrated the feasibility of the generation of the target cell library.

In order to isolate DNA from target cells that have been productively recognized by a CTL, reporter assays for productive antigen recognition in a target cell were developed. GzB protease activity is used as a readout/marker of recognized target cells. GzB is a cytotoxic protease secreted by CTLs into recognized target cells that triggers caspase activation and apoptosis. Reporters of GzB are not activated by general apoptosis pathways, meaning that only target cells killed by CTLs are isolated. This reduces the antigen-independent background noise in the methods described herein. Previous work demonstrated that the GzB released into target cells during cytolytic killing leads to complete proteolysis of GzB targets, suggesting robust enzymatic activity to serve as the basis of a reporter.

Figure 3:
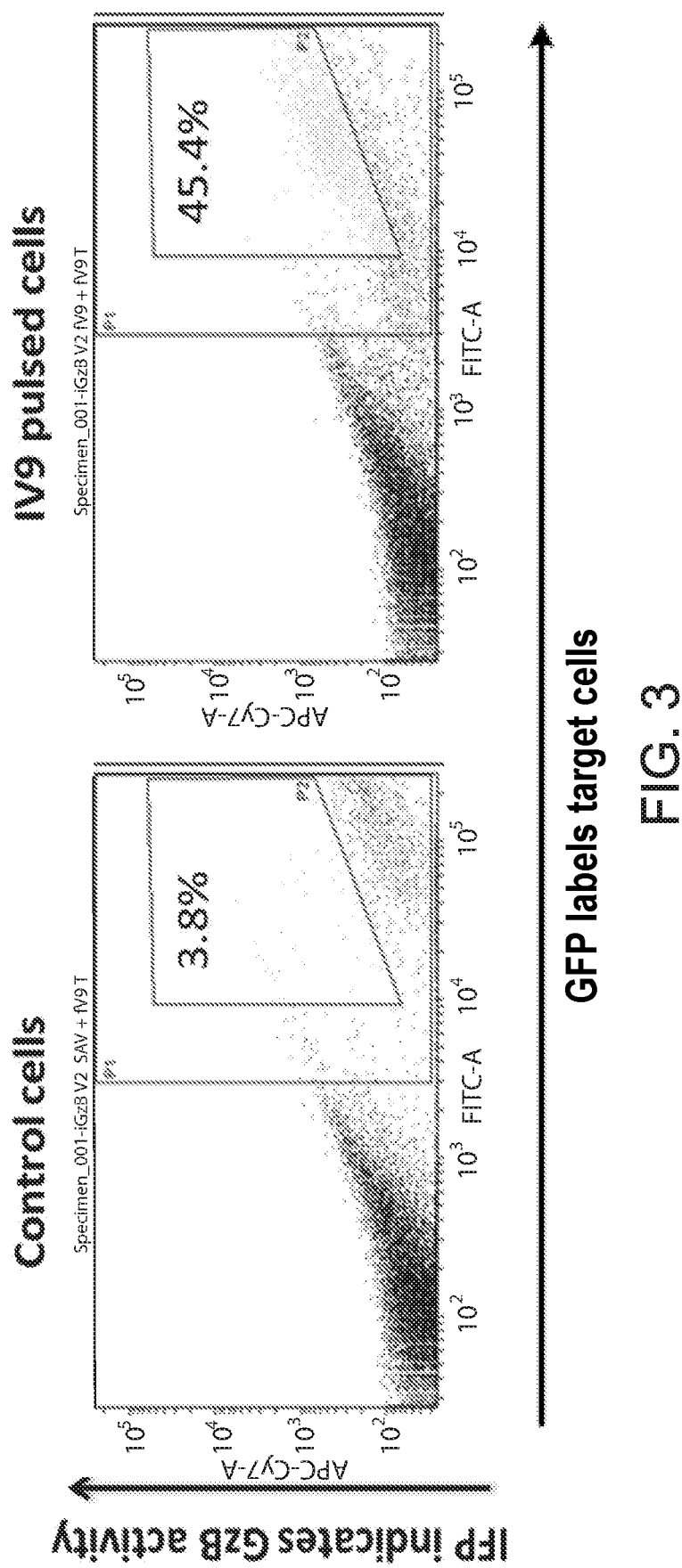
FIG. 3 depicts an exemplary fluorogenic reporter of GzB activity. GFP-labeled target cells expressing a fluorogenic GzB reporter were pulsed with a control peptide or the cognate IV9 peptide before co-culture with IV9 CTLs. GzB activity is detected by measuring infrared fluorescent protein signal in the target cells.

To detect GzB activity, a new fluorogenic GzB reporter protein was developed based on work described in To et al. PNAS 112(11): 3338-3343 (2015), generating a modified infrared fluorescent protein that is unable to mature due to a constraining peptide linker between two domains. Proteolytic cleavage of this linker allows the protein to fold properly and results in an up to 1000-fold increase in fluorescence. To et al. PNAS 112(11): 3338-3343 (2015) have successfully used this reporter to detect the activity of caspases and of the TEV protease. The reporter was modified as described herein to instead detect GzB cleavage. As a test of this reporter, target cells stably expressing the fluorogenic GzB reporter were generated. Co-culture with IV9 CTLs led to an increase in infrared fluorescent protein signal in IV9-pulsed but not control-pulsed target cells (FIG. 3), consistent with efficient detection of GzB activity.

Figure 4A:
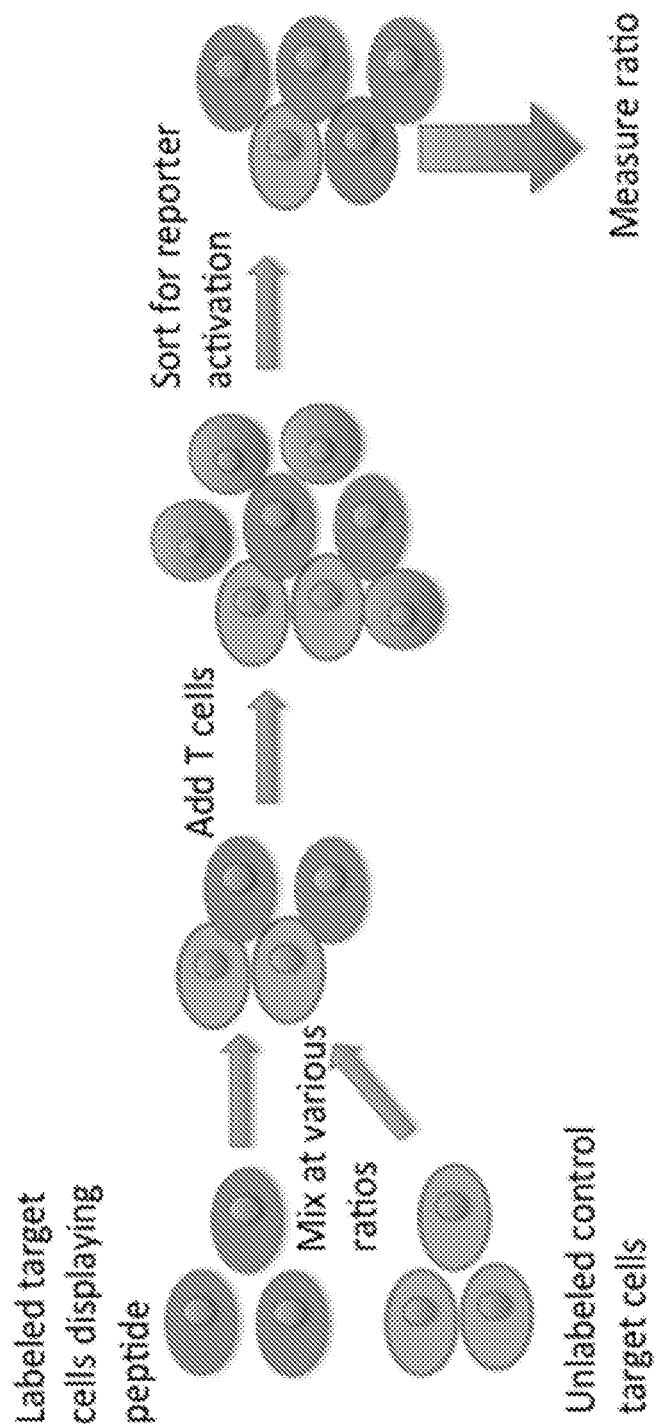
FIGS. 4A-4B depict a reconstruction experiment demonstrating enrichment of target cells displaying cognate antigen.

To verify that the platform described herein can enrich target cells displaying the cognate antigen of a CTL, a reconstruction experiment was performed. Target cells expressing the GzB reporter and displaying the IV9 peptide were labeled with a violet cell stain. These cells were then mixed with unstained target cells that also expressed the GzB reporter but displayed a control peptide. Various ratios of IV9-displaying to control cells were used to simulate antigen libraries of increasing complexity. The mixed cells were co-cultured with the IV9 CTLs and target cells that had activated the GzB reporter were isolated. The violet stain was used to calculate the enrichment of target cells displaying the IV9 peptide among all target cells that had activated the GzB reporter. This experiment is illustrated in FIG. 4A.

Figure 4B:
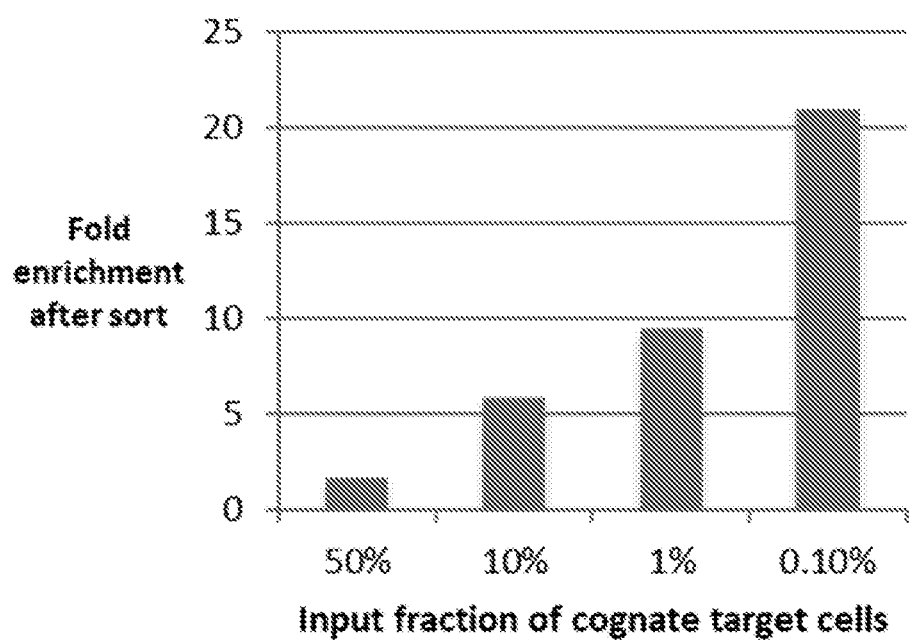

The results of the experiment are presented in FIG. 4B and demonstrate strong enrichment of target cells displaying the cognate IV9 antigen. A 21-fold enrichment of target cells displaying the cognate antigen was observed when using an initial dilution of 1:1000 (the lowest dilution we tested). This condition simulates a library of 1,000 different antigens and verifies that this platform can be used to identify target antigens from very complex libraries of candidates.

The final step towards applying this approach is to enable the recovery of intact antigen library from the genomic DNA of recognized target cells. However, GzB initiates caspase activation in target cells, which leads to internucleosomal degradation of genomic DNA by the caspase-activated deoxyribonuclease (CAD). CAD is normally inactivated by the protein inhibitor of CAD (ICAD), which is a caspase substrate, but overexpression of caspase-resistant (D117E) ICAD has been shown to block the degradation of DNA during apoptosis (Sakahira et al., Nature. 1:391(6662):96-9. 1998). Target cells that had been modified to express the caspase-resistant D117E ICAD gene by lentiviral transduction and selection were used. The results obtained demonstrate that this strategy allows for the recovery of intact genomic DNA from apoptotic cells.

Figure 5A:
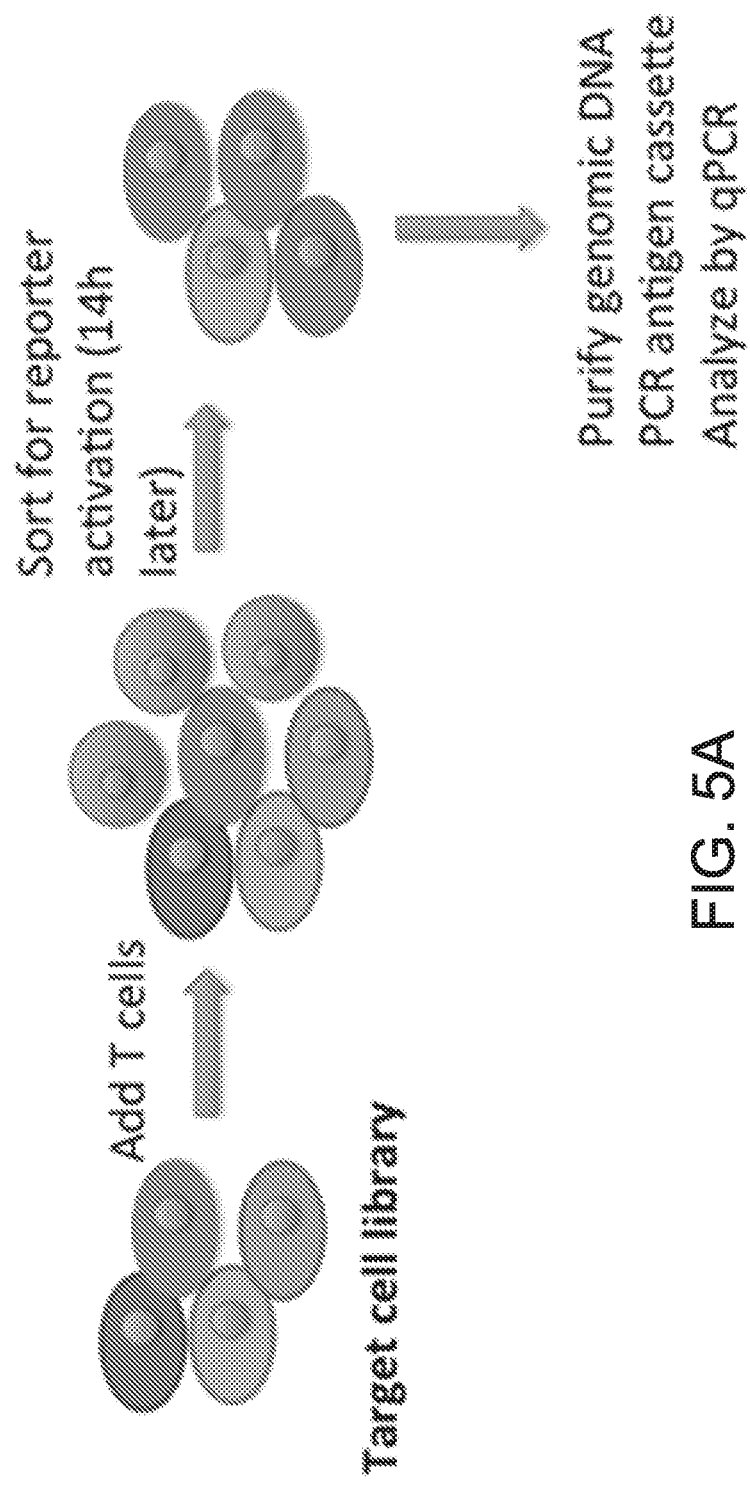
FIGS. 5A-B depict detection of CTL antigen in a screen.
Figure 5B:
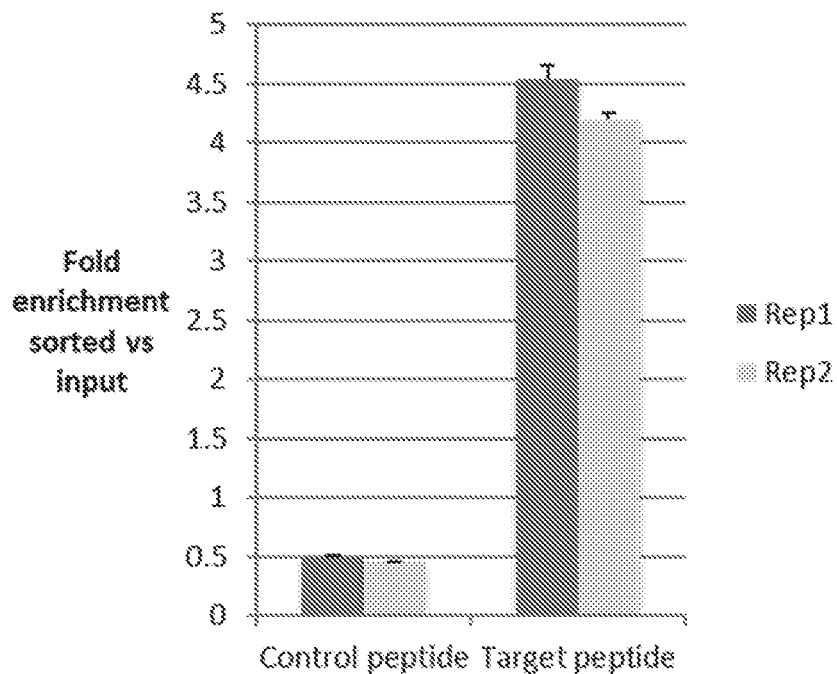

To verify that this platform can successfully enrich CTL targets from a complex antigen library, a screen for targets of the T cell clone was performed. A library of 2,494 peptide fragments tiling across the complete proteomes of ten HIV strains in 56 amino acid steps was generated. This library was cloned into a lentiviral vector and introduced into target cells expressing our GzB reporter and mutant ICAD with mutations D117E and D224E. The library of target cells was then co-cultured with the IV9 CTL clone overnight and target cells that activated the GzB reporter were isolated by FACS. PCR was performed to amplify the antigen cassette from the genomic DNA of the input and sorted cells and qPCR to quantify the enrichment of select peptides in the sorted cells. This experiment is illustrated in FIG. 5A and the results are shown in FIG. 5B. A significant and reproducible enrichment of the peptide encoding the IV9 CTL antigen was observed, while a control antigen was not enriched significantly. This demonstrates that the platform can be used to screen complex antigen libraries for the targets of CTLs and that these targets can be detected comprehensively by using next generation sequencing.

Example 2. Identification of a T Cell Antigen from a Complex Library by High Throughput Sequencing To demonstrate that the platform can be used to discover CTL targets from a complex antigen library, a reconstruction screen for targets of the T cell clone of interest was performed. A library encoding 2,494 peptide fragments tiling across the complete proteomes of ten HIV strains in 56 amino acid steps was generated. This library was cloned into a lentiviral vector and introduced into target cells expressing our GzB reporter and mutant ICAD with mutations D117E and D224E. The library of target cells was then co-cultured with the IV9 CTL clone overnight and target cells that activated the GzB reporter were isolated by fluorescence-activated cell sorting (FACS). PCR was used to amplify the antigen cassette from the genomic DNA of the input and sorted cells and Illumina sequencing to characterize the antigens enriched in the cells recognized by the T cell clone.

Figure 8:
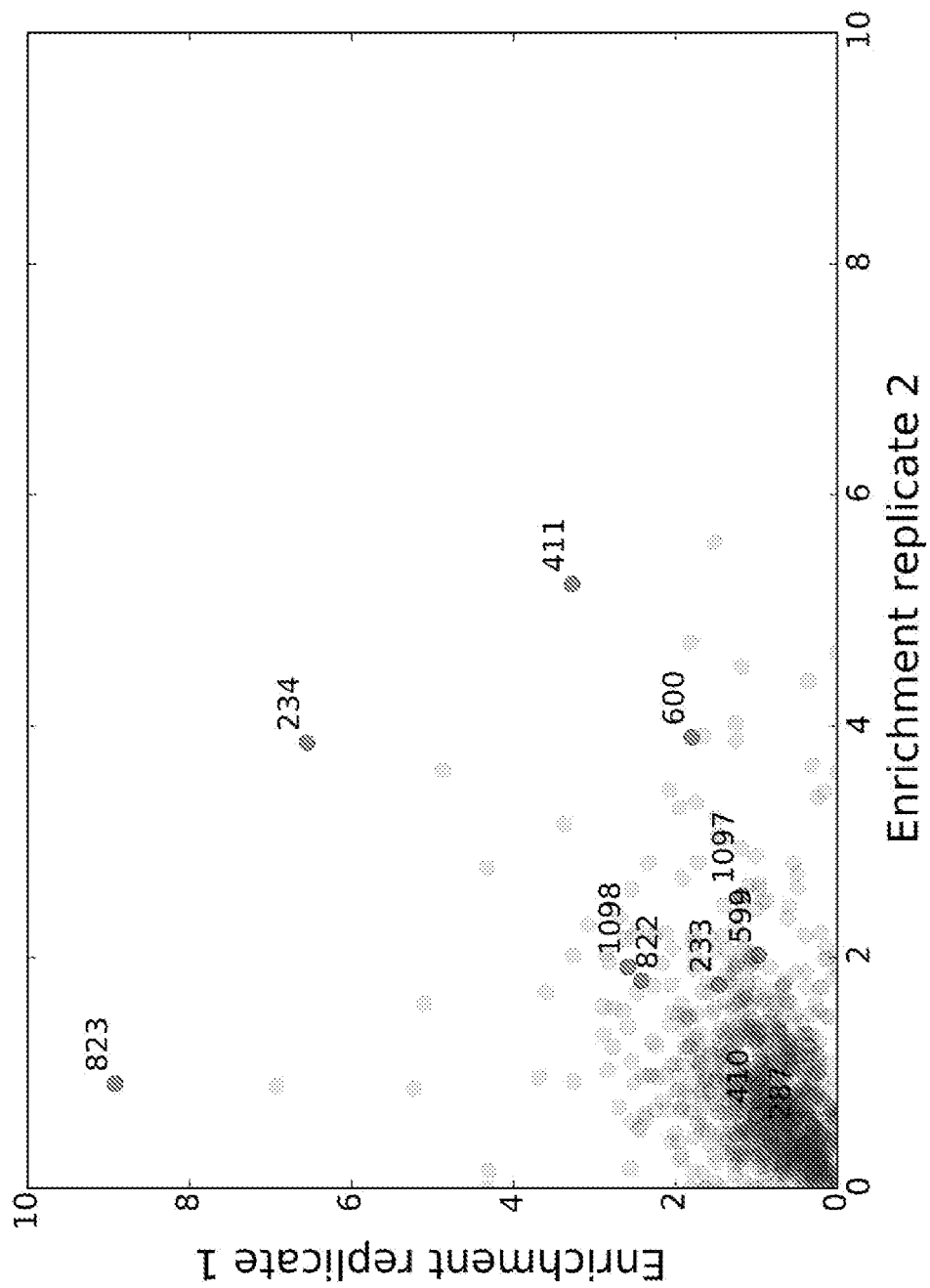
FIG. 8 is a graphical representation of results of the IV9 T cell screen. Each dot represents the fold-enrichment in each of two biological replicates for one peptide in the library. The dots identified by association with a numerical label are all of the peptides that contain the known target of the IV9 T cell.
Figure 9:
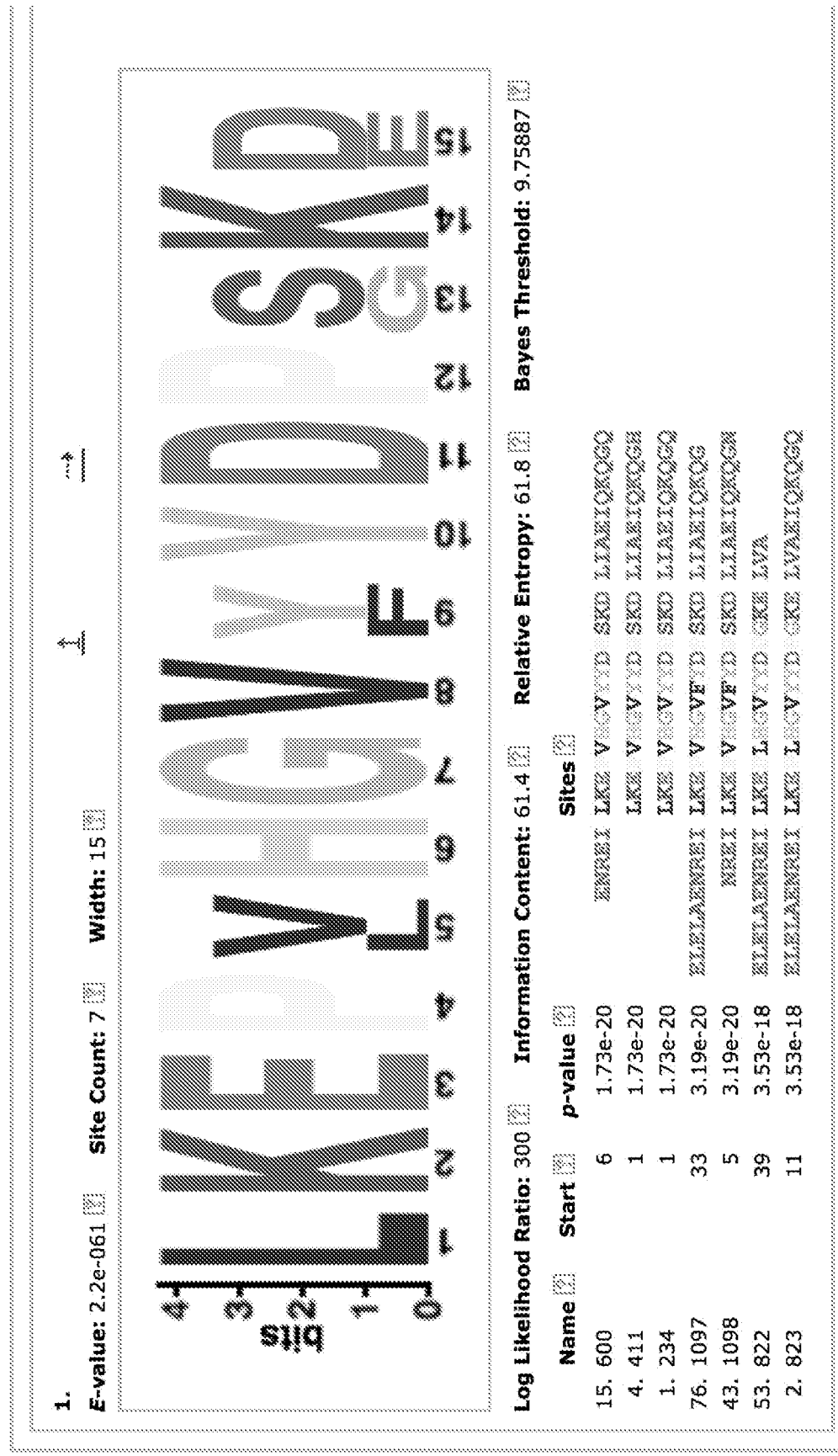
FIG. 9 is a chart that lists the motifs discovered by analysis. The IV9 epitope was identified by this motif analysis. The top enriched motif identified by MEME analysis on the 100 most enriched peptides from the IV9 screen contains the exact IV9 epitope (ILKEPVHGV).

FIG. 8 plots the fold-enrichment after sorting for each peptide in our library, across two biological replicates of this experiment. The peptides plotted with numerical annotation contain the known target epitope of the IV9 CTL clone that was used. The strongest and most reproducible enrichments are for peptides that contain the IV9 epitope, and there is at least moderate enrichment of almost every such peptide. Moreover, unbiased motif analysis of the most enriched peptides in the screen revealed the precise IV9 epitope as the top recurring motif (FIG. 9). Together, these data demonstrate that the compositions and methods can be used to accurately identify T cell targets from highly complex antigen pools.

Example 3. Application of GzB Reporter to CD4 T Cells

Steps have also been taken to demonstrate that the approach can be used to identify the targets of CD4 T cells or other T cells that do not themselves have cytotoxic activity. This can be achieved by introducing a T cell receptor (TCR) of interest into primary cytotoxic CD8 T cells. The cytotoxic T cells are then redirected to recognize and kill target cells of the introduced TCR. Target cells recognized by the TCR of interest can then be identified using a reporter of GzB as described herein.

An experiment was performed to demonstrate that this approach can be used to successfully generate CTLs that take on the specificity of CD4 TCRs. Lentiviral infection was used to introduce a CD4 TCR (Ob1A.12) that recognizes the MBP peptide in the context of an MHC Class II molecule into primary cytotoxic CD8 T cells. CD8 T cells modified with the Ob1A.12 TCR, but not a control TCR, were able to specifically activate the GzB reporter in target cells displaying the MBP peptide in the proper MHC II molecule (FIG. 10). This result demonstrates that the GzB reporter can identify the targets of CD4 T cells and enables the identification of targets of Th1, Th2, and Treg CD4 T cells in the context of infectious disease, cancer, and autoimmunity.

Example 4. Alternative Granzyme B Reporters

As described herein, many GzB-based reporters allowing for the detection of GzB activity in target cells that have been productively recognized by a CTL are contemplated. For example, several alternative reporters of GzB activity have been generated. These reporters can be used independently or in combination with the fluorogenic protease reporter described above to isolate target cells recognized by CTLs.

For example, one method for detection of GzB activity was developed that uses an inactive, membrane-tethered Cre recombinase that is activated by GzB cleavage of its tether. This releases the Cre to enter the nucleus and activate a reporter in response to T cell recognition. Cre-mediated recombination of a LoxP reporter generates a primer configuration that allows for PCR amplification of the antigen cassette in the recognized cell. The antigens that are productively recognized can be identified by Illumina sequencing of the PCR product from target cells after treatment with cytotoxic cells. This approach is diagrammed in FIG. 6A.

Figure 6B:
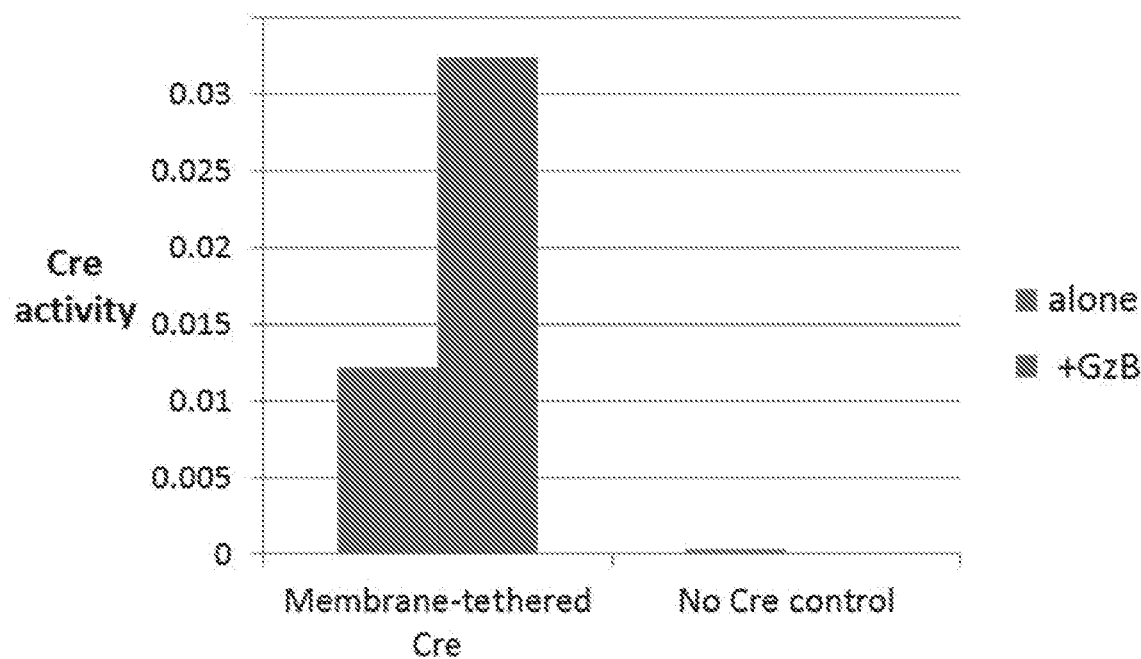

To demonstrate the feasibility of this approach, a test was performed. Target cells were modified to express: 1) membrane-tethered Cre recombinase with a GzB cleavage sequence on the tether, 2) a reporter cassette that contains two loxP sites that can be inverted by Cre recombinase, and 3) the D117E mutant form of ICAD to preserve genomic DNA during apoptosis. The introduction of GzB into these target cells by Natural Killer cells led to the cleavage of Cre recombinase and an approximately 3-fold increase in reporter inversion, as detected by qPCR (FIG. 6B). This reporter would similarly work for cytotoxic T cells, which use the same perforin- and granzyme-mediated mechanism of cytolysis as NK cells. This demonstrates the feasibility of using Cre recombination to detect GzB activity and highlights our ability to recover intact DNA from cells targeted for killing.

Another alternative would be to use a caspase reporter, rather than GzB. However, the granzyme reporter, unlike a caspase reporter, is not activated during caspase-mediated apoptosis, and has a lower level of background activation (an approximately 3-fold reduced background without affecting positive signal) in the context of our T cell killing assay.

Another approach developed for detecting GzB activity is based on staining (intracellular or extracellular, depending on whether the reporter is expressed in the cytoplasm or targeted to the membrane) for an antibody target that is only revealed following GzB cleavage of a reporter that serves as a substrate for GzB. The reporter contains a Flag epitope directly preceded by a GzB cleavage motif. Prior to cleavage, the internal Flag epitope is not recognized by the M1 Flag antibody, which only recognizes N-terminal Flag epitopes. However, following GzB cleavage, the Flag epitope is exposed at the N-terminus of the C-terminal cleavage fragment and can be stained using the M1 antibody. This approach is illustrated in FIG. 7A.

Figure 7B:
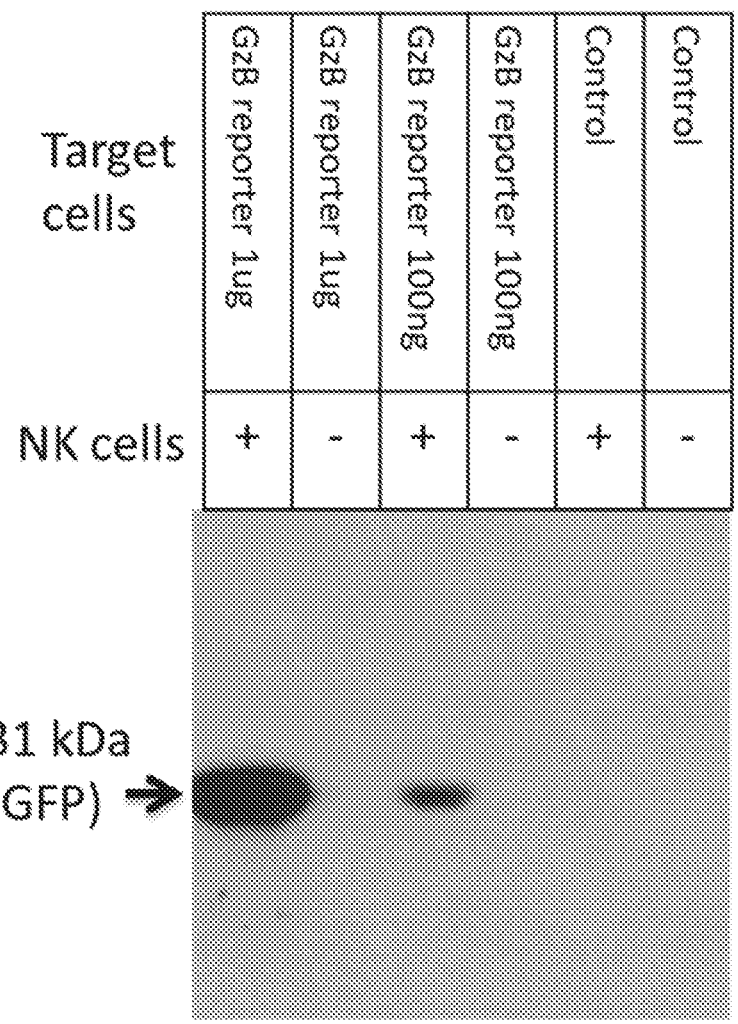

This method resulted in a profound increase in the abundance of M1 antibody target following exposure of the reporter to GzB delivered by NK cells as detected by Western blot analysis using an M1 Flag antibody on cell lysates from target cells expressing the GzB reporter with and without delivery of GzB by NK cells (serving as the cytotoxic lymphocytes in this proof of concept experiment) (FIG. 7B). The cleaved substrate can further be detected by antibody staining and flow cytometry to accommodate the herein described screening methods.

Figure 25:
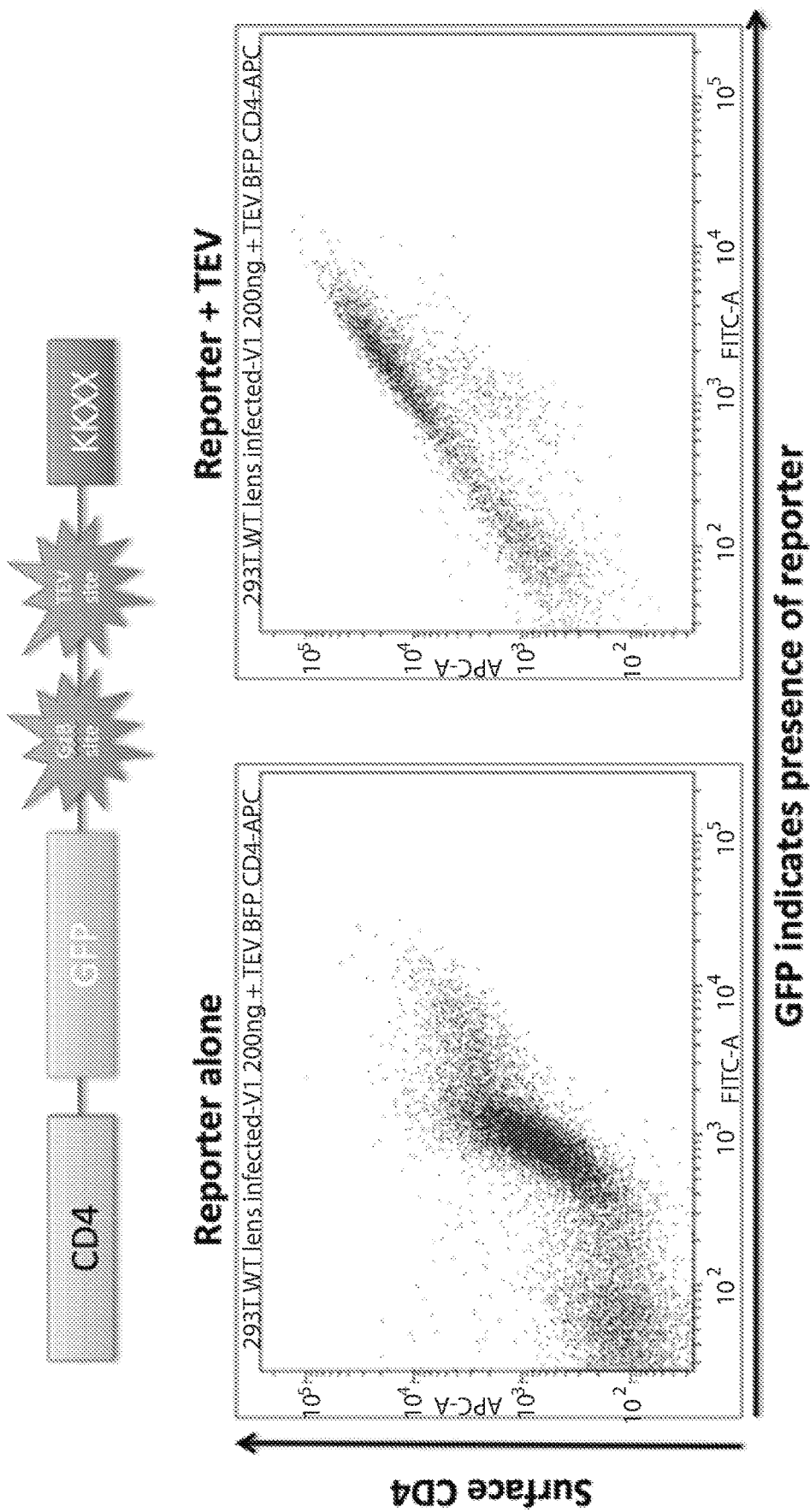
FIG. 25 shows the results of design and testing of an engineered protease reporter. A reporter protein (CD4) was fused to GFP and retained in the ER by addition of a C-terminal KKXX motif. The expression of TEV protease (right panel) results in increased surface expression of CD4 by cleaving the ER retention motif, as detected by staining with an anti-CD4 APC antibody.

Still another reporter of GzB activity in target cells is based on a a reporter protein that is sequestered inside the cell with an ER retention motif. Upon GzB cleavage of the ER retention motif, the reporter protein can be released and detected, such as by transit to the cell surface, where it can be used for isolation of target cells. To demonstrate that this approach successfully detects proteolysis, CD4 was used as the reporter protein, which included a TEV cleavage site before the ER retention motif. For ER retention, a C-terminal KKXX motif, wherein X is any amino acid, e.g., KKYL (SEQ ID NO:17), was used that has been previously reported to sequester proteins in the ER (see Nilsson et al., Cell, 58 (4): 707-718 (1989)). The reporter was fused to GFP in order to track the expression of the reporter. The entire construct and sequence is presented below. Co-expression of TEV with the construct resulted in a significant increase in CD4 on the cell surface (FIG. 25).

The sequence of the KKXX reporter sequence used is as follows:

(SEQ ID NO: 18)
GGGGACAAGTTTGTACAAAAAAGCAGGCTCAGGAATTCTCACCATGAACC

GGGGAGTCCCTTTTAGGCACTTGCTTCTGGTGCTGCAACTGGCGCTCCTC

CCAGCAGCCACTCAGGGAAAGAAAGTGGTGCTGGGCAAAAAAGGGGATAC

AGTGGAACTGACCTGTACAGCTTCCCAGAAGAAGAGCATACAATTCCACT

GGAAAAACTCCAACCAGATAAAGATTCTGGGAAATCAGGGCTCCTTCTTA

ACTAAAGGTCCATCCAAGCTGAATGATCGCGCTGACTCAAGAAGAAGCCT

TTGGGACCAAGGAAACTTCCCCCTGATCATCAAGAATCTTAAGATAGAAG

ACTCAGATACTTACATCTGTGAAGTGGAGGACCAGAAGGAGGAGGTGCAA

TTGCTAGTGTTCGGATTGACTGCCAACTCTGACACCCACCTGCTTCAGGG

GCAGAGCCTGACCCTGACCTTGGAGAGCCCCCCTGGTAGTAGCCCCTCAG

TGCAATGTAGGAGTCCAAGGGGTAAAAACATACAGGGGGGGAAGACCCTC

TCCGTGTCTCAGCTGGAGCTCCAGGATAGTGGCACCTGGACATGCACTGT

CTTGCAGAACCAGAAGAAGGTGGAGTTCAAAATAGACATCGTGGTGCTAG

CTTTCCAGAAGGCCTCCAGCATAGTCTATAAGAAAGAGGGGAACAGGTG

GAGTTCTCCTTCCCACTCGCCTTTACAGTTGAAAAGCTGACGGGCAGTGG

CGAGCTGTGGTGGCAGGCGGAGAGGGCTTCCTCCTCCAAGTCTTGGATCA

CCTTTGACCTGAAGAACAAGGAAGTGTCTGTAAAACGGGTTACCCAGGAC

CCTAAGCTCCAGATGGGCAAGAAGCTCCCGCTCCACCTCACCCTGCCCCA

GGCCTTGCCTCAGTATGCTGGCTCTGGAAACCTCACCCTGGCCCTTGAAG

CGAAAACAGGAAAGTTGCATCAGGAAGTGAACCTGGTGGTGATGAGAGCC

ACTCAGCTCCAGAAAAATTTGACCTGTGAGGTGTGGGACCCACCTCCCC

TAAGCTGATGCTGAGCTTGAAACTGGAGAACAAGGAGGCAAAGGTCTCGA

AGCGGGAGAAGGCGGTGTGGGTGCTGAACCCTGAGGCGGGGATGTGGCAG

TGTCTGCTGAGTGACTCGGGACAGGTCCTGCTGGAATCCAACATCAAGGT

TCTGCCCACATGGTCCACCCCGGTGCAGCCAATGGCCCTGATTGTGCTGG

GGGGCGTCGCCGGCCTCCTGCTTTTCATTGGGCTAGGCATCTTCTTCTGT

GTCAGGTGCCGGCACCGAAGGCGCCAAGCAGAGCGGATGTCTCAGATCAA

GAGACTCCTCAGTGAGAAGAAGACCTGCCAGTGCCCTCACCGGTTTCAGA

AGACATGTAGCCCCATTGGCGGCCGCATGGTGAGCAAGGGCGAGGAGCTG

TTCACCGGGGTGGTGCCCATCCTGGTCGAGCTGGACGGCGACGTAAACGG

CCACAAGTTCAGCGTGTCCGGCGAGGGCGAGGGCGATGCCACCTACGGCA

AGCTGACCCTGAAGTTCATCTGCACCACCGGCAAGCTGCCCGTGCCCTGG

CCCACCCTCGTGACCACCCTGACCTACGGCGTGCAGTGCTTCAGCCGCTA

CCCCGACCACATGAAGCAGCACGACTTCTTCAAGTCCGCCATGCCCGAAG

GCTACGTCCAGGAGCGCACCATCTTCTTCAAGGACGACGGCAACTACAAG

ACCCGCGCCGAGGTGAAGTTCGAGGGCGACACCCTGGTGAACCGCATCGA

GCTGAAGGGCATCGACTTCAAGGAGGACGGCAACATCCTGGGGCACAAGC

TGGAGTACAACTACAACAGCCACAACGTCTATATCATGGCCGACAAGCAG

AAGAACGGCATCAAGGTGAACTTCAAGATCCGCCACAACATCGAGGACGG

CAGCGTGCAGCTCGCCGACCACTACCAGCAGAACACCCCCATCGGCGACG

GCCCCGTGCTGCTGCCCGACAACCACTACCTGAGCACCCAGTCCGCCCTG

AGCAAAGACCCCAACGAGAAGCGCGATCACATGGTCCTGCTGGAGTTCGT

GACCGCCGCCGGGATCACTCTCGGCATGGACGAGCTGTACAAGCTTGTAG

GACCAGACTTCGGGCGCGAGAACCTGTACTTCCAGTCTAGAACTCTGGCC

AGCTCCCTGACTTTCAAGAAGTATCTGTAACTAGCTGACCCAGCTTTCTT

GTACAAAGTGGTCCCC

Example 5. Genome-Wide Screens Identify Known and Novel T Cell Targets

A set of screens applying the compositions and methods described to various T cell populations was performed. These screens demonstrated that the compositions and methods identify the correct target antigens of previously characterized TCRs, and, importantly, discovers novel, biologically meaningful antigens of T cell populations at genome-wide scale.

Figure 16:
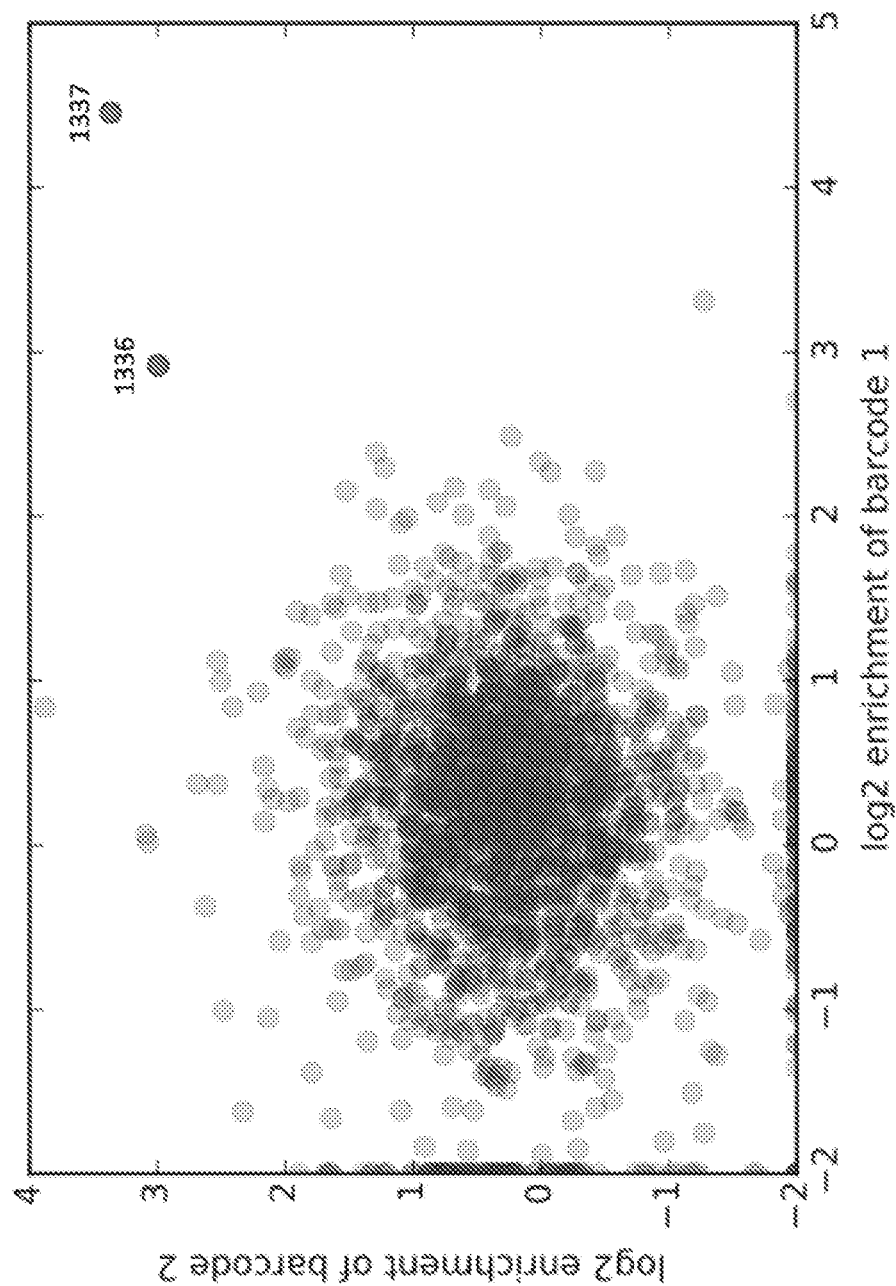
FIG. 16 shows the results of a CMV genome-wide screen with NLV2 TCR. Two thousand eight hundred and eight two 56 amino acid long peptides tiled every 28 amino acids across the CMV genome were encoded with two distinct DNA barcodes. Each dot on the scatter plot shows the performance of the two barcodes corresponding to one peptide sequence. The two dots in the upper right-hand corner identified by association with a numerical label are the only two epitopes in the library that contain the known target of the NLV2 TCR (NLVPMVATV (SEQ ID NO:4)).

To demonstrate that the target of a known TCR can be correctly identified, a TCR that recognizes the NLV epitope of CMV PP65 was synthesized. This TCR was introduced into primary donor CD8 T cells by lentiviral transduction, and these cells were used to screen a library of 2882 candidate 56-mers tiling across the CMV genome. The only two 56 amino acid peptides in the library that contain the NLV epitope were the top two scoring peptides in the library, enriching 7- to 20-fold (FIG. 16 and Table 1). Notably, no other peptides reproducibly enriched over 4-fold. This experiment demonstrated that the platform successfully identified the targets of "revived" TCRs introduced into donor CD8 T cells.

TABLE 1

| Name | Gene | Peptide | Start aa | End aa | Enrichment barcode 1 | Enrichment barcode 2 |
|---|---|---|---|---|---|---|
| 1337 | ORFL205C_ (UL83) | HNPAVFTWPPWQAGILARNLVPM VATVQGQNLKYQEFFWDANDIYRI FAELEGVWQ (SEQ ID NO: 19) | 477 | 532 | 21.7 | 10.1 |
| 1336 | ORFL205C_ (UL83) | GVMTRGRLKAESTVAPEEDTDEDS DNEIHNPAVFTWPPWQAGILARNL VPMVATVQ (SEQ ID NO: 20) | 449 | 504 | 7.3 | 7.7 |

Figure 17:
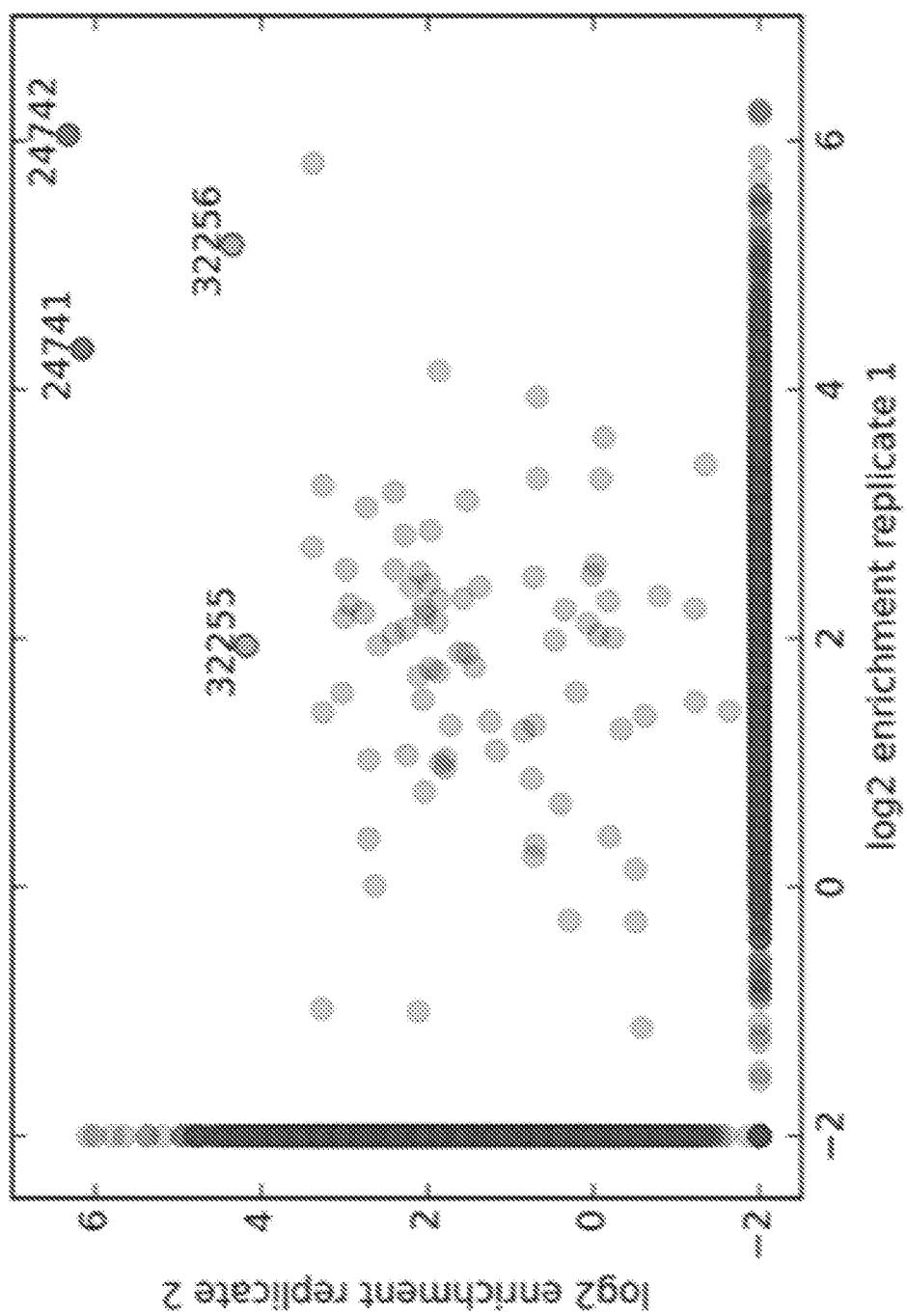
FIG. 17 shows the results of a virome-wide screen with patient T cells. Ninety three thousand nine hundred and four 56 amino acid long peptides tiled every 28 amino acids across the genomes of 206 viral species were screened with patient T cells that had been expanded in the presence of the NLV peptide. Each dot on the scatter plot shows the performance of one peptide in each of two biological replicates of the screen. The two dots identified by association with the numerical labels, "24741" and "24742," are the only two epitopes in the library that contain the NLV epitope (NLVPMVATV (SEQ ID NO:4)). The two dots identified by association with the numerical labels, "32255" and "32256," encode overlapping 56-mers from the UL123 (IE1) protein that were targeted by 2% of the sample T cells shown in FIG. 18.
Figure 18:
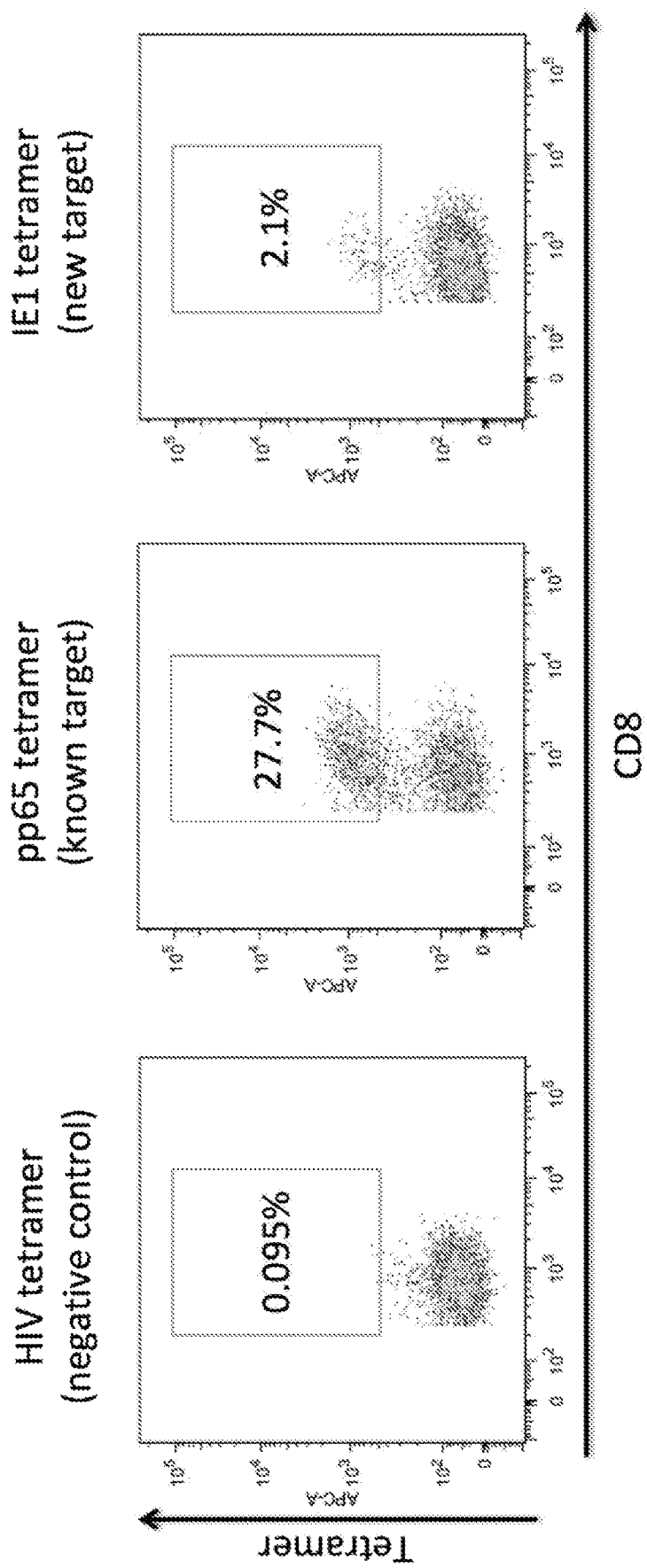
FIG. 18 shows validation of a novel epitope discovered in virome-wide screen. HLA-A2 tetramers loaded with a negative control peptide, known pp65 NLV peptide, or newly discovered IE1 (UL123) peptide were used to stain the population of T cells used in the virome-wide screen. 27.7% of the CD8-positive T cells in the input population recognized the NLV peptide, while 2.1% recognized the IE1 epitope.

To demonstrate that the platform can screen even more complex sets of tens to hundreds of thousands of antigens, a virome-wide screen was performed. In this screen, primary T cells was used from an HLA-A2 positive, CMV-positive donor that had been expanded in the presence of the NLV peptide. These cells were screened against a library of over 93,000 candidate antigens tiling across the whole genomes of 206 viral species in 56 aa steps with 28 aa overlap. The only two 56-mers in the library that contained the NLV epitope were the top two enriching peptides, enriching 25- to 100-fold (FIG. 17 and Table 2). Two additional overlapping 56-mers enriched 15- to 40-fold, and an epitope in the 28 aa region shared by these two 56 mers was validated as being recognized by approximately 2% of the input CD8 T cells (FIG. 18). This experiment demonstrated that the platform identified novel T cell targets at genome-wide scale. Notably, the 93,000 candidate antigen library screened is more complex than the entire human ORFeome collection (around 20,000 full length ORFs). Furthermore, this experiment showed that multiple T cell populations can be characterized at once, since a novel target that was only recognized by a 2% subset of the T cells was identified and validated.

TABLE 2

| Name | Gene | Peptide | Start aa | End aa | Enrichment barcode 1 | Enrichment barcode 2 |
|---|---|---|---|---|---|---|
| 1336 | ORFL205C_ (UL83) | GVMTRGRLKAESTVAPEEDTDEDSDN EIHNPAVFTWPPWQAGILARNLVPMV ATVQ (SEQ ID NO: 19) | 449 | 504 | 99.4 | 90.9 |
| 1337 | ORFL205C_ (UL83) | HNPAVFTWPPWQAGILARNLVPMVA TVQGQNLKYQEFFWDANDIYRIFAELE GVWQ (SEQ ID NO: 20) | 477 | 532 | 85.3 | 84.4 |
| 1823 | ORFL264C_ (UL123) | ETMCNEYKVTSDACMMTMYGGISLLS EFCRVLCCYVLEETSVMLAKRPLITKPE VI (SEQ ID NO: 21) | 281 | 336 | 26.4 | 71.4 |
| 1824 | ORFL264C_ (UL123) | CRVLCCYVLEETSVMLAKRPLITKPEVIS VMKRRIEEICMKVFAQYILGADPLRVC (SEQ ID NO: 22) | 309 | 364 | 123.6 | 48.9 |

Figure 20:
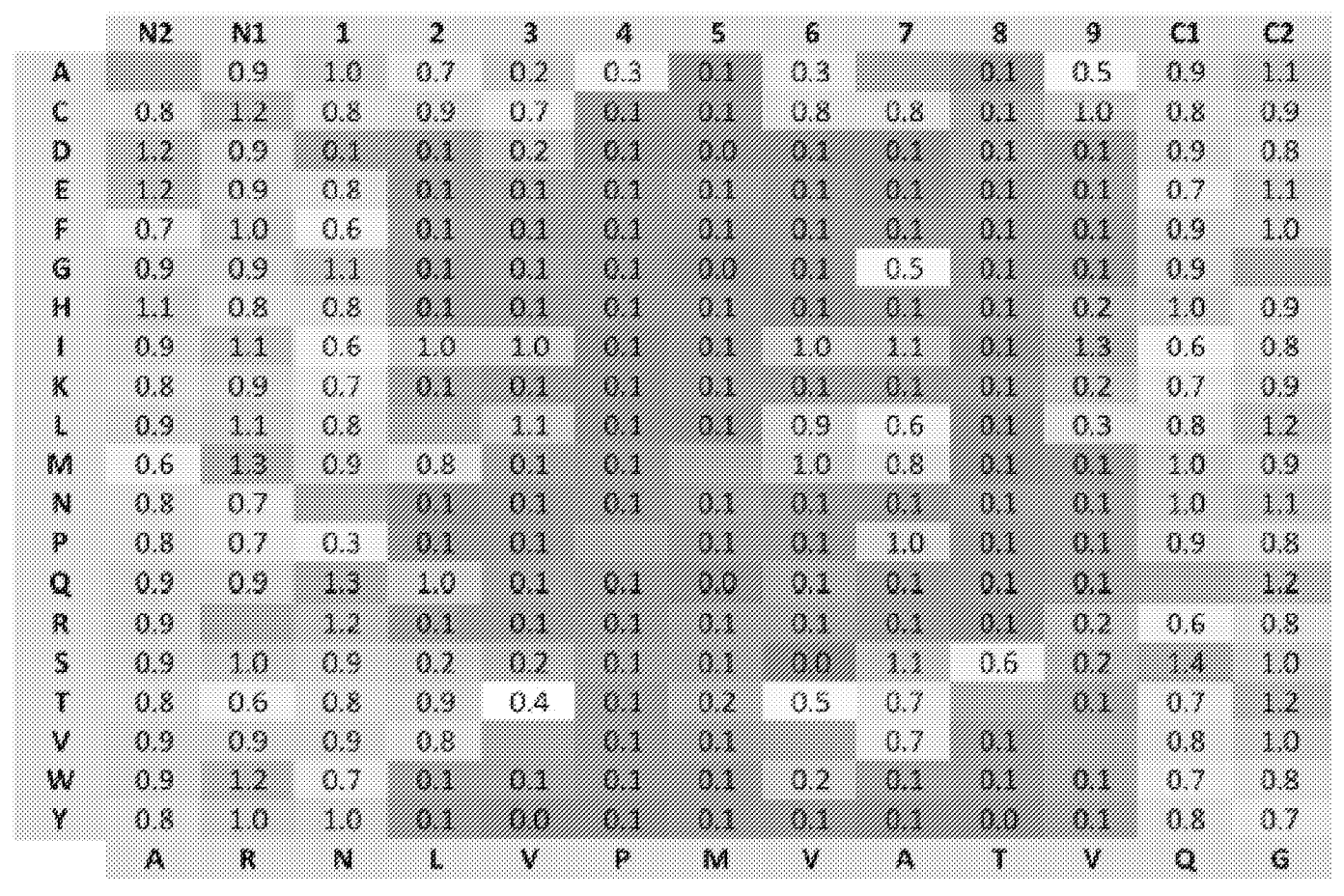

Next, a genome-wide library vs. library screen was performed to demonstrate that novel immunodominant targets of polyclonal T cells can be identified at whole-genome scale. Bulk memory T cells were purified from an HLA-A2 positive, CMV-positive donor. These T cells were screened against the CMV-wide library of 2,882 epitopes. Six sets of overlapping 56-mers that enriched reproducibly were identified (Table 3). All six of these candidate antigens contain predicted high-affinity HLA-A2 binders in the 28 aa overlap region (FIG. 20). By contrast, only 10% of 28 aa stretches are predicted to contain a high-affinity HLA-A2 binder. One of the enriched epitopes was the known immunodominant PP65 epitope, which was validated was recognized by 0.3% of the T cells. The remaining five identified epitopes had not been previously reported. This experiment demonstrated that novel T cell targets of polyclonal T cells can be identified at genome scale in a library vs. library setting.

TABLE 3

Immunodominant epitopes discovered in CMV library vs. library screen.

| ID | Gene | 56mer sequence |
|---|---|---|
| 1336 | ORFL205C_ (UL83) (pp65) | GVMTRGRLKAESTVAPEEDTDEDSDNEIHNPA VFTWPPWQAGILARNLVPMVATVQ (SEQ ID NO: 20) |

TABLE 3-continued

Immunodominant epitopes discovered in CMV library vs. library screen.

| ID | Gene | 56mer sequence |
|---|---|---|
| 1337 | ORFL205C_(UL83) (pp65) | HNPAVFTWPPWQAGILARNLVPMVATVQGQN LKYQEFFWDANDIYRIFAELEGVWQ (SEQ ID NO: 19) |
| 2140 | ORFS333C_(U58) | DYYYYREDEPRQHGEPNYVAPPARQFRFPPLNN VSSYQASCVVKDGVLDAVWRVQG (SEQ ID NO: 23) |
| 2141 | ORFS333C (U58) | PPLNNVSSYQASCVVKDGVLDAVWRVQGTFYP EKGIVARVGWSGRRGRKWGRLHAP (SEQ ID NO: 24) |
| 1560 | ORFL232C_(UL100) | VSMVTQYRSYKRSLFFFSRLHPKLKGTVQFRTL IVNLVEVALGFNTTVVAMALCYG (SEQ ID NO: 25) |
| 1561 | ORFL232C_(UL100) | QFRTLIVNLVEVALGFNTTVVAMALCYGFG NNFFVRTGHMVLAVFVVYAIISIIYF (SEQ ID NO: 26) |
| 2058 | ORFL321W | STDSDGKSIIAGVQVVDHDEDIIAPQSLWCTAF KEALWDVALLEVPRWAWQGWKRW (SEQ ID NO: 27) |
| 2059 | ORFL321W | WCTAFKEALWDVALLEVPRWAWQGWKR WRNSESGRRWSAGSASASSLSDLAGEAVG (SEQ ID NO: 28) |
| 670 | ORFL117C_(UL46) | VEFEAQPGALLIRMETGCDSPRHLYISLYLLGI RASNVSASTRCLLESVYTASAAR (SEQ ID NO: 29) |
| 671 | ORFL117C_(UL46) | YLLGIRASNVSASTRCLLESVYTASAARAALQ WLDLGPHLLHRRLETLGCVKTVSL (SEQ ID NO: 30) |
| 405 | ORFL92C_(UL32) | LARIQERCKLLVKELRMCLSFDSNYCRNILKH AVENGDSADTLLELLIEDFDIYVD (SEQ ID NO: 31) |
| 406 | ORFL92C_(UL32) | ILKHAVENGDSADTLLELLIEDFDIYVDSFPQ SAHTFLGARSPSLEFDDDANLLSL (SEQ ID NO: 32) |

Figure 19:
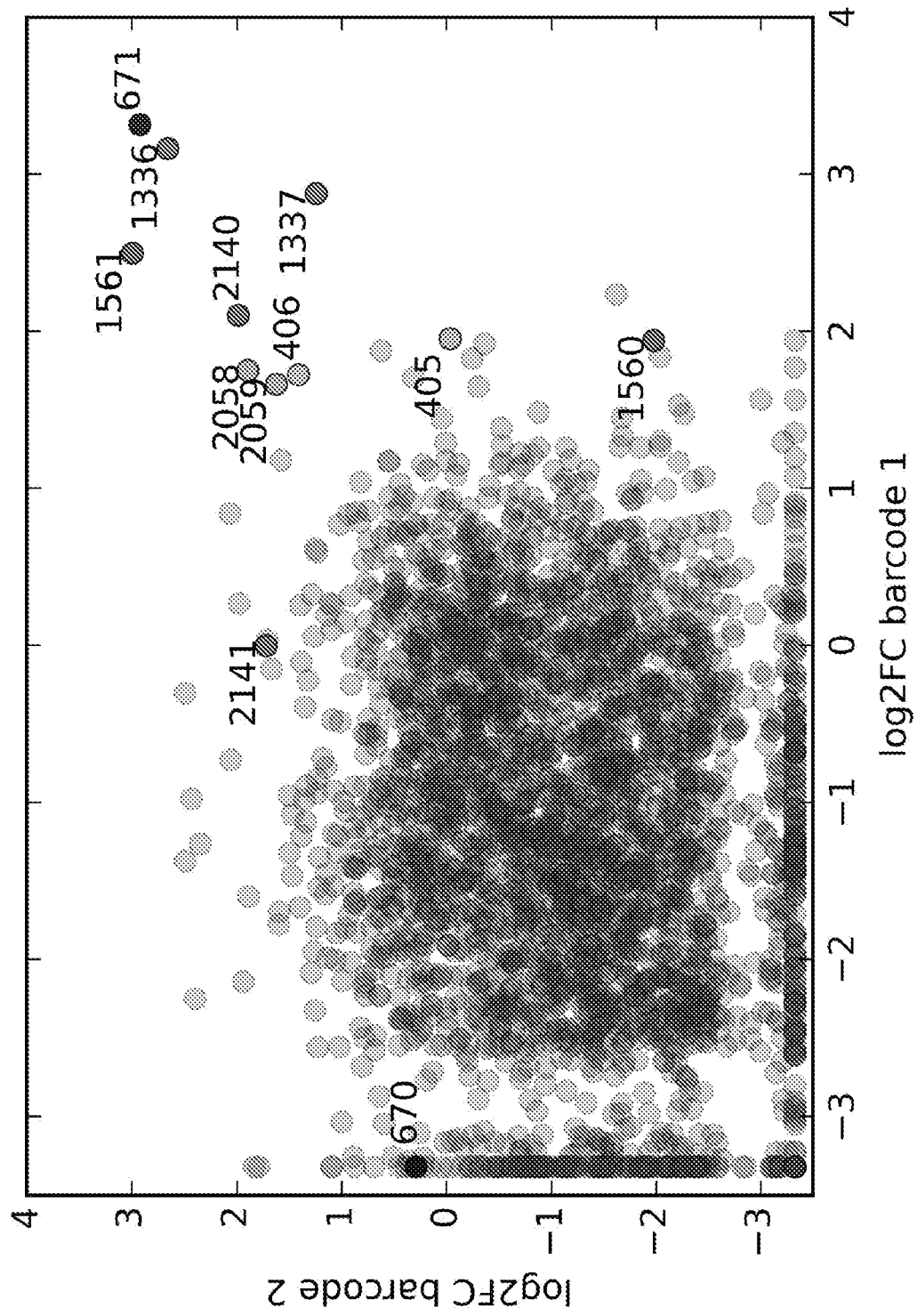
FIG. 19 shows the results of a CMV genome-wide library vs. library screen using polyclonal memory T cells. Memory T cells from a CMV-positive, HLA-A2 positive donor were used to screen a library of 2,882 56 amino acid long peptides tiled every 28 amino acids across the genome of CMV. Each dot represents the performance of two independent DNA barcodes encoding a particular 56 amino acid peptides. Peptides with two overlapping 56 amino acid peptides that enriched are identified by association with a numerical label.

Table 3 shows six sets of overlapping 56-mers that reproducibly enriched in the screen described in FIG. 19. In 6/6 cases, there is a high-affinity predicted HLA-A2 binding epitope found in the 28 aa overlap region (bold). By contrast, only 10% of 28 mers are expected to have a high-affinity HLA-A2 binding epitope. Epitope 1336-1337 is a well-established immunodominant epitope, while the remaining five epitopes have not been previously reported.

To demonstrate that the platform can map the landscape of a TCR-epitope interaction, a comprehensive mutagenesis screen was performed. The NLV-expanded primary T cells described above was used. A library of all of the single amino acid mutants of the known target epitope, in addition to the two upstream and downstream residues, were screened. Mutation of the upstream or downstream amino acids did not abrogate T cell recognition, whereas most mutations in the epitope itself reduced epitope recognition (FIG. 6). This approach accurately maps the exact recognized epitope of a T cell in the context of a larger recognized antigen. Moreover, this approach can be used to identify potential off-targets for a T cell by mapping the critical and permitted TCR-interacting residues, which can be used to search for related off-target peptide sequences.

Figure 21:
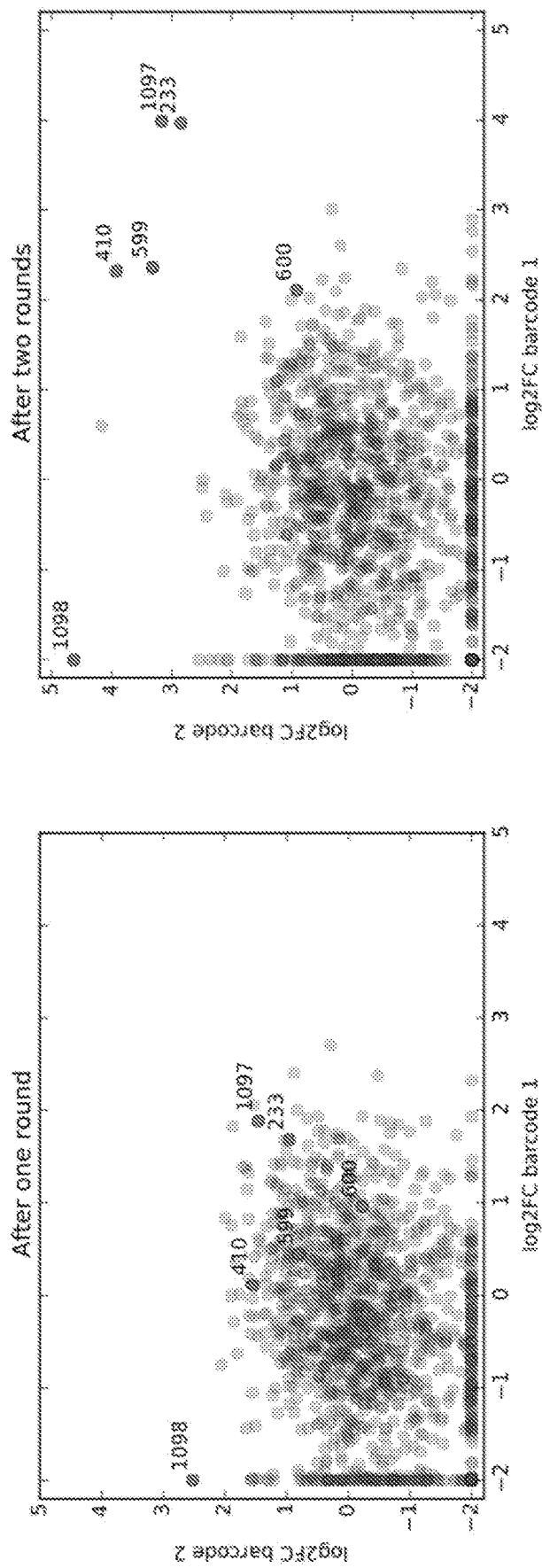
FIG. 21 shows that detection of TCR targets is improved with multiple rounds of screening. Each dot represents the performance of two DNA barcodes for a given peptide after one round (left panel) or two rounds (right panel) of a screen with an IV9-specific TCR. The six dots identified by association with a numerical label show the six peptides in the antigen library that were known targets of the TCR.

The platform allows for the successive enrichment of target epitopes through multiple rounds of screening. A gene encoding a TCR that recognizes the IV9 epitope of HIV polymerase was synthesized and was introduced into primary donor CD8 T cells by lentiviral transduction. The resulting cells were used to screen a library of 1,247 candidate 56-mers tiling across the genome of ten strains of HIV. To perform a second round of selection, the isolated antigens were amplified and re-cloned into the lentivirus expression vector. They were then introduced into target cells by viral transduction. The screen was repeated with the same IV9 T cells. Increased enrichment of the known targets of the IV9 TCR was observed with the second round of selection (FIG. 21). Therefore, the platform can be used in multiple rounds of selection to improve the performance of antigen identification.

Example 6. Application of Platform to Tumor-Derived TCRs

Figure 22:
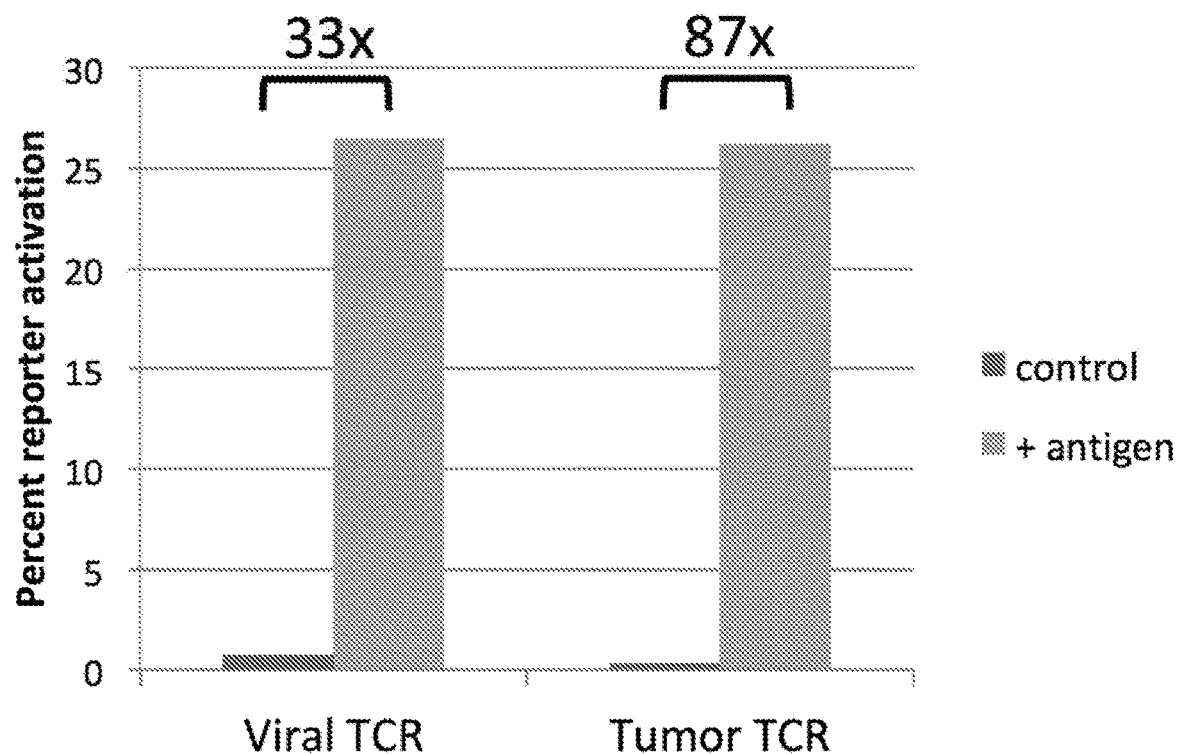
FIG. 22 shows signal to noise analysis results of tumor-specific TCR. The NLV-specific CMV TCR (Viral TCR) and a MAGE-A3 tumor-specific TCR (not affinity enhanced, Tumor TCR) were introduced into donor CD8 T cells. The recognition of MHC-matched cells in the absence (control) or presence (+antigen) of cognate antigen was measured, and demonstrated comparable performance of the TCRs.

To demonstrate that the platform can identify the targets of tumor-derived TCRs, signal-to-noise analyses were conducted. The signal-to-noise analysis of the T cell activity quantifies how efficiently the T cell activates the reporter in the presence versus absence of its known antigen. For all of the viral screens, this signal-to-noise measure was very predictive of the target enrichment observed in the actual screen. The T cells we are working with that recognize tumor antigens give comparable signal-to-noise as the antiviral T cells we previously used, which provides further confidence that the screens work well (FIG. 22). This allows for a variety of genome-wide human screens to identify known and novel targets of TCRs, such as tumor-derived TCRs.

Example 7. Inhibiting CAD-Mediated DNA Degradation

Figure 23:
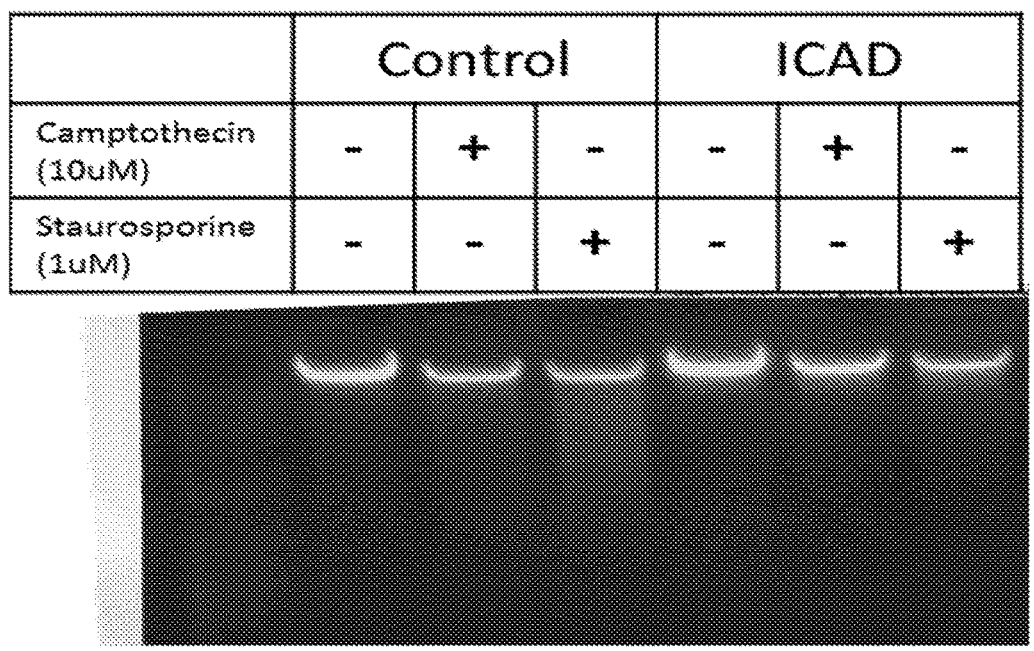
FIG. 23 shows that overexpression of mutant ICAD prevents DNA degradation during apoptosis. Target cells without (Control) or with (ICAD) overexpression of mutant ICAD were treated with apoptosis-inducing agents, camptothecin and staurosporine. Genomic DNA was purified and showed the hallmark DNA smear and laddering when apoptosis was induced in control cells, but not in the presence of mutant ICAD.

A key challenge in granzyme-based detection of T cell activity is that granzyme initiates apoptosis upon entry into target cells, including the hallmark intranucleosomal degradation of genomic DNA by the nuclease CAD. Prior to apoptosis, CAD is kept inactive by its inhibitor protein ICAD. ICAD is a direct caspase substrate that is degraded during apoptosis, freeing CAD to degrade DNA. The platform allows for the recovery of intact antigen cassette DNA from cells that have received granzyme. Thus, the DNA degradation that occurs during early apoptosis limits the ability to identify the antigens that had driven T cell recognition. It has been determined herein that this challenge can be overcome by inhibiting CAD-mediated DNA degradation. For example, it has been determining that over-expressing a mutant, caspase-resistant version of the ICAD protein in target cells prevents CAD nuclease activity after granzyme delivery. It was verified that overexpression of this mutant ICAD prevents genomic DNA laddering following the induction of apoptosis (FIG. 23).

Figure 24:
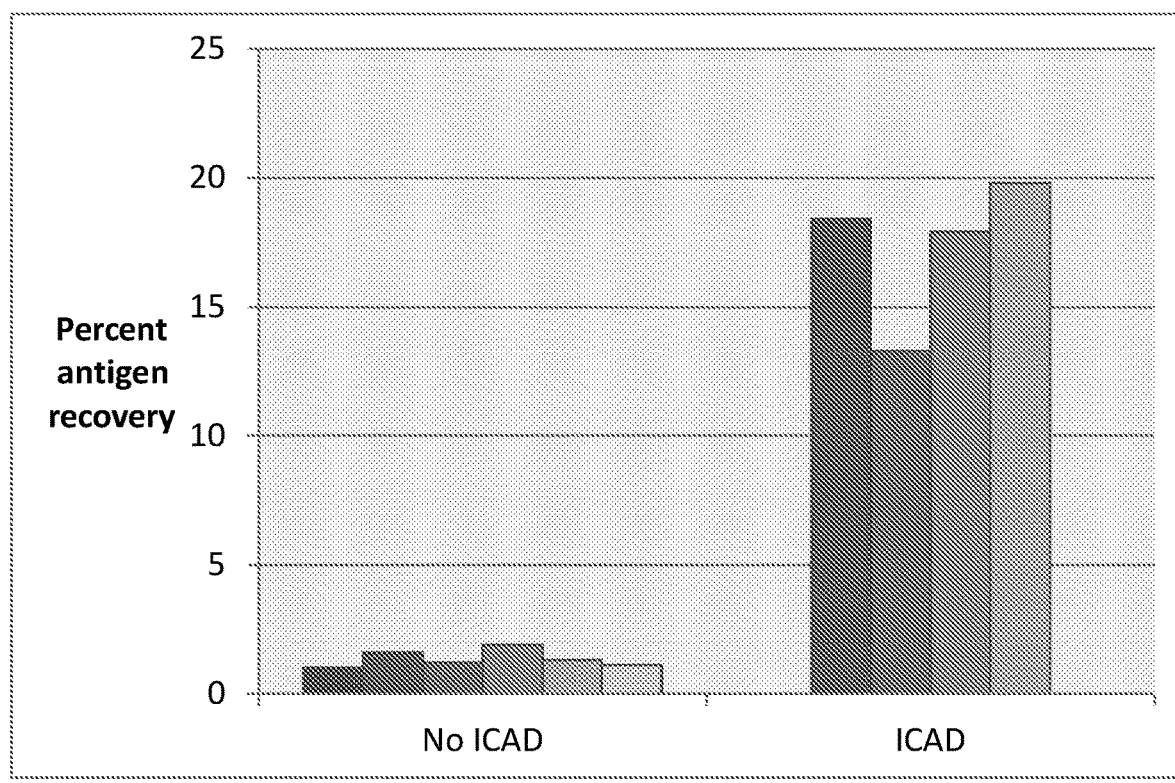
FIG. 24 shows that expression of mutant ICAD enhances antigen cassette recovery in the screen setting. The number of antigen cassettes recovered by sequencing was compared with the number of sorted cells to calculate the efficiency of antigen recovery. Each bar shows the percent antigen recovery in one screen replicate performed in the absence (No ICAD) or presence (ICAD) of over-expressed mutant ICAD.

Inhibiting CAD-mediated DNA degradation to recover antigen information was determined to be important in the screen setting. The efficiency of antigen recovery in the context of separate screens that had been performed with or without ICAD overexpression was calculated. Briefly, the observed distribution of reads per antigen to the expected Poisson distribution of cell number counts was mapped, and the fit was used to estimate the total number of cells characterized in each screen replicate. This number of cells recovered by sequencing was then compared to the known number of cells isolated by FACS to determine the net efficiency of antigen recovery. Across six replicates of screens conducted in the absence of ICAD, antigen information was recovered from only 1-2% of the sorted cells (FIG. 24). By contrast, screens performed with mutant ICAD overexpression resulted in approximately ten-fold higher efficiency of antigen recovery (FIG. 24). Notably, there were no differences in the genomic DNA preparation, PCR, and sequencing steps between the screens. These results indicate that inhibition of DNA degradation, e.g., by the overexpression of mutant ICAD, enables an approximately ten-fold improvement in assay performance and enables the screening of significantly more complex antigen libraries.

REFERENCES

Cameron, B J et al. Identification of a Titin-Derived HLA-A1-Presented Peptide as a Cross-Reactive Target for Engineered MAGE A3-Directed T Cells. Sci Trans Med 197ra103 (2013).

Sakahira, H., Enari, M. & Nagata, S. Cleavage of CAD inhibitor in CAD activation and DNA degradation during apoptosis. Nature 391, 96-99 (1998).

Sekaly, R. The failed HIV Merck vaccine study: a step back or a launching point for future vaccine development? *JEM* 205 (1): 7, (2008).

To, T L et al. Rationally designed fluorogenic protease reporter visualizes spatiotemporal dynamics of apoptosis in vivo. PNAS 112(11): 3338-3343 (2015).

Kolowos, W., Schmitt, M., Herrman, M., Harrer, E., Low, P., Kalden, J. R., Harrer, T. (1999) Biased TCR Repertoire in HIV-1-Infected Patients Due to Clonal Expansion of HIV-1-Reverse Transcriptase-Specific CTL Clones. J Immunol 162:7525-7533.

Schub, A., Schuster, I. G., Hammerschmidt, W., Moosmann, A. (2009) CMV-Specific TCR-Transgenic T Cells for Immunotherapy. J Immunol, 183:6819-6830.

Xu, G. J.,* Kula, T.,* Xu, Q., Li, M. Z., Vernon, S. D., Ndung'u, T., Ruxrungtham, K., Sanchez, J., Brander, C., Chung, R. T., O'Connor, K. C., Walker, B., Larman, H. B., Elledge, S. J. (2015) Comprehensive serological profiling of human populations using a synthetic human virome. Science, 348 (6239), aaa0698

OTHER EMBODIMENTS

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. An antigen presenting cell (APC) comprising:
   a) an exogenous nucleic acid encoding one or more candidate antigens, wherein the one or more candidate antigens are expressed and presented with WIC class I or WIC class II molecules;
   b) a molecular reporter of Granzyme B (GzB) activity; and
   c) an exogenous nucleic acid encoding inhibitor of caspase-activated deoxyribonuclease (ICAD) in expressible form, an exogenous inhibitory nucleic acid targeting caspase-activated deoxyribonuclease (CAD), a CAD knockout, or a caspase knockout.

2. The APC of claim 1, wherein the exogenous nucleic acid is stably introduced into the genome of the APC.

3. The APC of claim 2, wherein the exogenous nucleic acid is stably introduced into the genome of the APC via a lentiviral vector, a retroviral vector, or a transposon.

4. The APC of claim 1, wherein the exogenous nucleic acid is flanked on each side by predetermined primer recognition sequences.

5. The APC of claim 1, wherein the molecular reporter of GzB activity comprises a fusion polypeptide comprising a GzB cleavage site (VGPD, SEQ ID NO:1) linked to a detection molecule.

6. The APC of claim 1, wherein the molecular reporter of GzB activity comprises a modified infrared fluorescent protein, a membrane tethered CRE recombinase, an antibody-based reporter of GzB activity, an ER retention-based reporter of GzB activity, a cell surface detectable-based reporter of GzB activity, or combinations thereof.

7. The APC of claim 1, wherein the molecular reporter of GzB activity comprises a membrane tethered CRE recombinase, and the APC further comprises an inverted CRE reporter flanked by LoxP sites, optionally wherein the exogenous nucleic acid is located proximal to a CRE activated primer recognition sequence.

8. The APC of claim 1, wherein the caspase knockout is a caspase 3 knockout.

9. The APC of claim 1, wherein the APC i) does not express an endogenous MHC molecule and is engineered to express an exogenous MHC molecule and/or ii) is selected from the group consisting of a K 562 cell, a HEK 293 cell, a HEK 293 T cell, a U2OS cell, a MelJuso cell, a MDA-MB231 cell, a MCF7 cell, a NTERA2 cell, a LN229 cell, a dendritic cell, and a primary autologous B cell.

10. The APC of claim 1, wherein the candidate antigen is less than or equal to 8, 9, 10, 11, 20, 30, 50, 100, 200, or 300 amino acids in length.

11. The APC of claim 1, wherein the candidate antigen is greater than 300 amino acids in length.

12. The APC of claim 1, wherein the exogenous nucleic acid encoding a candidate antigen is derived from an infectious organism or human DNA.

13. The APC of claim 12, wherein the human DNA is obtained from a cancer cell.

14. The APC of claim 12, wherein the infectious organism is selected from the group consisting of a virus, a bacteria, a fungi, a protozoa, and a multicellular parasitic organism.

15. A library of APCs of claim 1, wherein the respective APCs comprise different exogenous nucleic acids that encode a candidate antigen to thereby represent a library of candidate antigens expressed and presented with WIC Class I and/or WIC Class II molecules.

16. The library of claim 15, wherein the exogenous nucleic acids are derived from an infectious agent or human DNA.

17. The library of claim 15, wherein the exogenous nucleic acids encode from about $10^2$ to about $10^{14}$ individual candidate antigens.

18. The APC of claim 1, wherein the exogenous nucleic acid encoding inhibitor of caspase-activated deoxyribonuclease (ICAD) in expressible form, exogenous inhibitory nucleic acid targeting CAD in expressible form, CAD knockout, or caspase knockout is an exogenous nucleic acid encoding inhibitor of caspase-activated deoxyribonuclease (ICAD) gene in expressible form.

19. The APC of claim 1, wherein the exogenous nucleic acid encoding inhibitor of caspase-activated deoxyribonuclease (ICAD) in expressible form, exogenous inhibitory nucleic acid targeting CAD in expressible form, CAD knockout, or caspase knockout is an exogenous inhibitory nucleic acid targeting CAD in expressible form.

20. The APC of claim 1, wherein the exogenous nucleic acid encoding inhibitor of caspase-activated deoxyribonuclease (ICAD) in expressible form, exogenous inhibitory nucleic acid targeting CAD in expressible form, CAD knockout, or caspase knockout is a CAD knockout.

21. The APC of claim 1, wherein the exogenous nucleic acid encoding inhibitor of caspase-activated deoxyribonuclease (ICAD) in expressible form, exogenous inhibitory nucleic acid targeting CAD in expressible form, CAD knockout, or caspase knockout is a caspase knockout.

22. The library of APCs of claim 15, wherein the exogenous nucleic acid encoding inhibitor of caspase-activated deoxyribonuclease (ICAD) gene in expressible form, exogenous inhibitory nucleic acid targeting CAD in expressible form, CAD knockout, or caspase knockout inhibits APC DNA degradation for recovery of candidate antigen from at least 5% of the APCs to about 50% of the APCs, from at least 5% of the APCs to about 10% of the APCS, from at least 10% of the APCs to about 20% of the APCs, or from 10-20% of the APCs.

* * * * *

UNITED STATES PATENT AND TRADEMARK OFFICE
CERTIFICATE OF CORRECTION

PATENT NO. : 11,834,653 B2
APPLICATION NO. : 16/619859
DATED : December 5, 2023
INVENTOR(S) : Stephen J. Elledge, Tomasz Kula and Mohammad Haj Dezfulian It is certified that error appears in the above-identified patent and that said Letters Patent is hereby corrected as shown below:

On the Title Page

Column 2 Item (57) (Abstract), Line 5, delete "MC class" and insert -- MHC class --

Column 2 Item (57) (Abstract), Line 6, after "and" delete "c)"

In the Claims

In Column 72, Line 49, Claim 22, delete "APCS," and insert -- APCs, --

Signed and Sealed this
Twenty-seventh Day of February, 2024

Katherine Kelly Vidal
Director of the United States Patent and Trademark Office